US007910522B2

(12) United States Patent
Nalin et al.

(10) Patent No.: US 7,910,522 B2
(45) Date of Patent: Mar. 22, 2011

(54) METHOD FOR THE EXPRESSION OF UNKNOWN ENVIRONMENTAL DNA INTO ADAPTED HOST CELLS

(75) Inventors: Renaud Nalin, Auzielle (FR); Petar Pujic, Serezin du Rhone (FR); Karine Tuphile, Morsang sur Orge (FR); Benjamin Gillet, Lyons (FR)

(73) Assignee: Libragen, Toulouse (FR)

( * ) Notice: Subject to any disclaimer, the term of this patent is extended or adjusted under 35 U.S.C. 154(b) by 432 days.

(21) Appl. No.: 10/522,037

(22) PCT Filed: Jul. 17, 2003

(86) PCT No.: PCT/EP03/07765
§ 371 (c)(1),
(2), (4) Date: Apr. 18, 2005

(87) PCT Pub. No.: WO2004/013327
PCT Pub. Date: Feb. 12, 2004

(65) Prior Publication Data
US 2005/0282166 A1 Dec. 22, 2005

(30) Foreign Application Priority Data
Jul. 24, 2002 (EP) .................................... 02291871

(51) Int. Cl.
C40B 50/06 (2006.01)
C12Q 1/68 (2006.01)
(52) U.S. Cl. .............................................. 506/26; 435/6
(58) Field of Classification Search .................. 506/26; 435/6
See application file for complete search history.

(56) References Cited

U.S. PATENT DOCUMENTS 5,614,398 A * 3/1997 O'Brochta et al. ........... 435/462
5,728,551 A * 3/1998 Devine et al. ..................... 435/6
2003/0143745 A1 * 7/2003 Martinez et al. ............... 435/486

FOREIGN PATENT DOCUMENTS

| EP | 0 176 321 | 4/1986 |
| WO | 98/17811 | 4/1998 |
| WO | 00/78977 | 6/2000 |
| WO | 01/40497 A2 | 6/2001 |

OTHER PUBLICATIONS

Chain et al., Journal of Bacteriology. vol. 182: 5486-5494; Oct. 2000.*
Groth et al., PNAS. vol. 97: 5995-6100; 2000.*
Berg et al., PNAS. vol. 79: 2632-2635; 1982.*
Rondon et al., PNAS. vol. 96: 6451-6455; 1999.*
Haldimann et al., Journal of Bacteriology. vol. 183(21): 6384-6393; Nov. 2001.*
Hoang et al. Plasmid. vol. 43: 59-72; 2000.*
J. Media et al., "Retrofitting Vectors for *Escherichia coli*-Based Artificial Chromosomes (PACS and BACS) with Markers for Transfection Studies", Genome Research, Cold Spring Harbor Laboratory Press, US, vol. 7, No. 2, Feb. 1997, pp. 179-186.
S. Kim et al., "Modification of Bacterial Artificial Chromosome Clones using Cre Recombinase: Introduction of Selectable Markers for Expression in Eukaryotic Cells", Genome Research, vol. 8, No. 4, Apr. 1998, pp. 404-412.
Database EMBL "Online!, Nov. 23, 2000, "*Arabidopsis thalania* chromosom 1*" retrieved from EBI, Database accession No. AC084820, XP002232359.
M. Rondon et al., "Cloning the Soil Metagenome: A Strategy for Accessing the Genetic and Functional Diversity of Unclutured Microorganisms", Applied and Enviromental Microbiology, Washington, DC, US, vol. 66, No. 6, Jun. 2000, pp. 2541-2547.
International Search Report dated Jan. 23, 2004 issued in PCT/EP03/07756.
Dennis et al, Applied and Environmental Microbiology, 1998, vol. 64, No. 7, pp. 2710-2715.
MacNeil, I. A. et al. "Expression and Isolation of Antimicrobial Small Molecules from Soil DNA Libraries" *BNS*, Apr. 2001, pp. 301-308, XP-001050545.
Sosio, M. et al. "Artificial chromosomes for antibiotic-producing actinomycetes" *Nature Biotechnology*, Mar. 2000, pp. 343-345, vol. 18, XP-001180029.
Yang, X. W. et al. "Homologous recombination based modification in *Esherichia coli* and germline transmission in transgenic mice of a bacterial artificial chromsome" *Nature Biotechnology*, Sep. 1997, pp. 859-865, vol. 15, XP-000770319.
European Office Action, Application No. 03 766 202.0, Jun. 22, 2009, pp. 1-6.

* cited by examiner

*Primary Examiner* — Sue Liu
(74) *Attorney, Agent, or Firm* — Saliwanchik, Lloyd & Eisenschenk

(57) ABSTRACT

The present invention relates to methods for the identification or cloning of polynucleotides encoding a selected phenotype, particularly from environmental DNA. In a specific embodiment, the method comprises (i) cloning environmental DNA fragments into *E. coli* cloning vectors to produce a metagenomic library, (ii) identifying or selecting cloning vectors in the library which contain DNA fragments having a particular characteristic of interest, (iii) modifying the identified or selected cloning vectors into shuttle or expression vectors for transfer and integration in a selected host cell, (iv) transferring the modified cloning vectors into the selected host-cell and (v) identifying or cloning the DNA fragments contained in the modified cloning vectors which encode the selected phenotype in the selected host cell.

21 Claims, 14 Drawing Sheets

SEQUENCE LISTING

```
<160> NUMBER OF SEQ ID NOS: 16

<210> SEQ ID NO 1
<211> LENGTH: 37500
<212> TYPE: DNA
<213> ORGANISM: Artificial sequence
<220> FEATURE:
<223> OTHER INFORMATION: DNA sequence of clone FS3-124.

<400> SEQUENCE: 1
gatcggtgcg ggcctcttcg ctattacgcc agctggcgaa aggggatgt gctgcaaggc      60 gattaagttg ggtaacgcca gggttttccc agtcacgacg ttgtaaaacg acggccagtg     120
aattgtaata cgactcacta tagggcgaat tcgagctcgg tacccgggga tcccacgtac     180
cacgagctca tctggaagag cccgctccag acacccgagg aatggaagcg cggcgtcgtg     240
agaccgtaca cgcagaagcg tctcgtcgcc ttcgttgact ggcttgcgac gacgatgaag     300
ctggatctca ccaggatgtt cgccgcaggc agctcgatgg gcggatcggg cgcgatcatg     360
ctcgcgattc gctatcccgc acgattcgcg tggaccgtgt cgtgggtcgg cgtccacgtg     420
```

```
cccgccgact ctccgcaatt cacatcgtcg tacgagctgg tgtacggccg gcccgacttg    480
aaggtgccgt tcgagaacgg cacgccggtc tgggatcatt ttagtgacgt ctggtacctg    540
cggcagcatc cggagcagga catcgggttc atcacgttct cgaacggcaa gaacgactcg    600
gcgatcggct ggcgccaggc cgtcgaattc ctgaagacgc tgcaggagac caggcaaccg    660
cacctgttcg tctggggcca ggagggacac ggccagcgcg cgaagatgcc ggaaggtggc    720
ggcgaacggg agatgccgct cgacctcaga acgaaccaga gcctgccggc gttcagccgt    780
tgcacgctcg acgacgatcc gggagacggg tcggattcga gcggcgtccc ggccgggcag    840
atcaactcct acgtcacctg gcagcctgac tcgatcgtcg acgaacccgg ccgatggagc    900
gtcgtcatca agctggcgaa tcgaccgccg cggtcgcccg ccgcagtcga cgtcacgccg    960
cggcggctgc agcagttcaa gctcaagccc ggcgatcagg tgacatggac gaactccgcg   1020
ggcaacaccg tcgtgcagcg cggcgaagcg gtcgcggacc ggtggggtct cgtcacgctc   1080
ccgcagatgc aggtctcaac gggtggaaac aggatcctgg tgagcaggaa ctaggcgggc   1140
ggcgtcctcg acgagccggc gcatcggcgc cagttgatgt gcccacgaaa gctggctgag   1200
gtccgcgcgc gcggcgatgt cccgtcgcgc ctgcggcggc tttgccagca aatccagcac   1260
agccgcccgg aacgcctcga ctgattccgc cacggagcac gccggccgtg cgatggtggg   1320
aagtccccct gcgacggccg gggtcacgac gttcgggagc cccgcggcaa tcgcttcgag   1380
cactttgttc tgcacgcctc tcgcgatcgc aatcggcgcg accgcgatcg ccgatcgcca   1440
gagatactcg cgtacctccg ggaccgcgcc ggtcacttca atcgtgggat cggccgcgag   1500
tgcccgcacc gcggcggtcg ggtccatgcc cacgagcatc agccgcgcgt ccgggcgggc   1560
gcgaaccacg gacggccaga cctctcgcgc gaaccagagc gccgcgcgct cgttgggctc   1620
gtagccgaac acgccgcaga agacgacccg cgcttcggcg gccggtggtc ctttcggcgc   1680
aaacatctcg acgtcgatgc cgttcggcac gaccgacgcc gtgaggccgc ccgtgacttc   1740
ttcgagcagc aggcgctcgc gctcgctcac gaccgtggtc gccgccgcgc gccgcatcgc   1800
gactttctcg aagcggagca agcggccggc ctcgcggcgg aacagccagc ctttcggcca   1860
cgccgccgtc gacgccagcg cgcgccattt ctcggagtcg acgtccacca tgtccaggac   1920 gaagggatc ccgcccagga tcggctcgca ggcgtagcgg gccatcccgc tgcagtacgc   1980
gagcaccgcg tcgggccgcg tcgcggcaat ccgtcgttcg agcacctggt agatctccgg   2040
cgaatgcagc aggacgtgcg tgaggggtcg atcgcccggc agcgccagac cgctcgcgat   2100
gagattccgg ccgcggcgga cgcgcacgac gtcggtcgac gccgtcacgc cggcgagatc   2160
cgctcgatgc gaccactcct cgtcgtcgtg cgcgagcgag acgaggtgca cgtcggcgga   2220
tcgtgcgagc gtgtgaatga gatgaaacgc gcgaatgcga tcgccccggt tcggggcgta   2280
gggcagccgg tgtgtgagca gaaggactct caccgtgcgg catccgatcg ctctcggatg   2340
acgcgggccg gtacgcccgc ggcgatcacg cgggcgggaa tcggcgcggt cacgaccgac   2400
cccgccgcaa tcacggaatc cggaccgacg tcagccatga ccacggcggc gctgccgatc   2460
caggtgccgg cgccgatccg caccatccgc ggtgtgcctg gctgctcacg gatcggccgc   2520
gtgaggtcgc tcgtgccgtg cgtgtccggt ccgctgggga tgtggacgcc ggcgccgacc   2580
aggacatcgc gctccaggtg gacccagccg agatggcatc cgggtcccac gtacacatgc   2640
tcgtcgagct tcgcgccggt ctgcgaaaag atggtgccga aggcgaccgt gaccgacggg   2700
tcgcagtgtg caagcacgcg gccgaggaaa gccgcgcgaa ggtattgtcc gatgacgccg   2760
gggatgagcg agagccactg cgtcgaccct tcgagggccc ggtcggcgcc gaggaagggc   2820
```

```
cgccgcacgg agtaggagag caaggcgggc aggacgagca ccagcgcgat gccacgggcc    2880
agtcccttgc cggcgtcctt gaggctcacg cccactgcag cgcgcgcccc cgtcggacc     2940 gggctccgta tcgtgtgacg agcgagtcgt agagcgcttc cactttgcgc atccgccgct    3000
cgaacgataa ctcttcttcg atccggcgtc gcgccgcaat cgcacgggtg cgtccggccg    3060
cgggattggc catcgcctgc tcgatcgcgt ccgcgaggcc tgacgcccgg ccgggctgaa    3120
tgaccagggc gtgcgtgccg ttcgacacga gctcggccgt gccccggcc gcggtcgcga     3180 cgatgggtgt ctcgaacgcc atggcttcga gcacggcgtt gggcgtccct tcgtagtccg    3240
acgactgcac gagcaggtcc agcccgtgat ggacggccga gacgtcggac gtgtggccga    3300
ggaaacgcca ggttccgggc ccgagctcgc gggcggcctg ttcctcgagc ggacgccgga    3360
ggctgccgtc gccggcgatg acgagacgga ggcgcggcca cttcgcctga agggcggcac    3420
aggcttcgat gagcaagtcg aatcgtttct gcggctcgag acggccaacc gcgccgatga    3480
cgaagtcgct ggcctcgaat cccagtcctt cacgcgccgc ggcctcagat cgtggatcgc    3540
gtcggaaagc atggtggtcg atgccattcg ggatcgtgac gacccgatcc ggccgtccgc    3600
ctttggccag gagctcccgc cgaatctgtt cggacacggc aatgacggca gggaagcggg    3660
cgagaatccg gcgatcgagc gggtagtaga cggtgcgttc gcgaaacgaa tggccggtcc    3720
atccatgggc cgtggccagc ggaatacgcg gctcggcgcg tcccaggagc agggcgagga    3780
gatcggtctt gtactcgtgc gcgtgcacga tgtcgatgcg cagatctttc acgagcgcgc    3840
ggagcttcga ccagattccg gtgtcgaacg aatgcttctc ccggacctcg acgtagtcga    3900
tgccggccgc tttcgcccgt tcgtccatgc cgaacaccgg atcgcgctgg tcgcggatgt    3960
agcagacggt gatcgcgtac ttggagcgat cggcctgcgc cgttccgagc agaatcgtct    4020
tctccggtcc gccgcccgtg ccccgcacgc tgcggagctc gagcacgcgc acgggacgcg    4080
cgattcccgg cctaggcgcg cgtctggca gcatggcccc ccggccgac gagcgcgatg      4140 gcccgggcga tatcgtacgt gccggccacg acgagcgact gtgcgatctc gacgagtccc    4200
actgcgccgc gccggcgccg gatcatcgcg gctgcgcgca agccggcgaa accggcaagc    4260
agcaggagcg cggtaccgac aatccaccac ccgccgcgct gccacagcgc gaggcccagc    4320
ggaatcgaga cgagcgccag cagatcgagg accgggatga tcacgctggg cagatcccgc    4380
atggcgagcc ggtgacggaa gctcacgcgc aggttgtcgc ggccgcgcca cagctcgccg    4440
aaaaacacgg cgcgaagcga tcggggatcg ccctggtgca cgctgcggag ccgcgggtcc    4500
gacaggatgc ggccgccgcc ccggcgcagc cgctggcaga tatccacgtc ttcacaggtc    4560
tcgaggctgg tatcgaagcc accggcgcgg tcgaaggcct cgcgcttcac ggcaagattg    4620
ccgctcggga gccagtccac gtcttcggtg ctctgcccac gacggcgaaa cgagtcgtac    4680
gcgcgctgca cccagttgcc gtcaccggga gcttcgtact gcgcgccggc agcgacgacc    4740
cccggggtct ggagcagatc gacggcgacc accggccagc gcgggtcgat ctcatgatcg    4800
gcgtcaacga acgccagcac gtcgccctcc gccgaccggg ccgcgcggtt gcgaagcgtc    4860
gccacgttca cgtcgggcag cgacagcact cgcgcggatc cgcgctctgc cacggcacgc    4920
gagtcgtcgg tcgacccgtt gtccgccacg acgatctcgt accagccagc cggcgcctcg    4980
gtgcgatgaa tcgacgccag gcaacggctg aggtgcgccg cgccgttctt gacggggatg    5040
acgaacgaca cgcgcggcgc cacggcaatt ttcgcggtca tcgatttcgt agcgcggccg    5100
gctttcgtag cgcggcccgg gttggggggcc gcgagaactc gaacgcgccc agatccggcg    5160 ccccctgctct cggccgccga tcgaaatcga gcggcgcctg cggaatctcg atgccggcgt    5220
```

```
cgatcgcctc cctggcggct gccgacaggt gcagatcgca cgaggccgcg tttgcgaacc    5280
actctgcggc ggcgttcgtg acgttgttcg tcgcctccgc ctcaccgccg ttacggcgca    5340
ggatctgccg gctcgtcagg ttgttgcgga tgagcccgtt cgtcacggga accggacgc    5400 cgatcgtcca cggcgtcgcc gtgccgagcg tgaagacgct gttgtgctcg atccggaagt    5460
cggtggacgc gttggcttcg atcgcttcgt cggcccattc gttcaggttg cagatcacgt    5520
tgttccgcac gatgccgcgc tggtgatcga tctgcttctc gccgtcgcgt gcgtaggccg    5580
tgatccccgc ggccaggccg atggcgatgc ccctgaacga atcgacgatg acgttccgtt    5640
cgatgagcgt gtcctgcgag ttcgcccagg cgaggatcgc cgggccggat cgccagccgc    5700
ccgattgcgg gccgcgaatc cgcaggaaga cgttgtcgcg gatgacccac ccccgggccg    5760
ccaggatgtc cacgccgtcg gtgtaatcgg acggcgcgct cgtcgtgtac tcgaagcgcg    5820
agcacgccac gaggccatcg tccgcgaagc gtccgtcagt gccgacgctg cctttgagca    5880
attgctgtcc cgcatcgatg agctggacgt tgtgcaccgt ggctcgggac gcgccaagct    5940
cgccgcgcac ctgaatcgcg tggtacccga cgtggccgac cgtcagatcc gcaatcgtca    6000
cgtcagtggc gccaaccgag agcgccacgc cgatcgcgtc gccggtcatg ccgccgccgc    6060
gaatgacgac gcggtcccga tcgccggagc ggctccggag cacggtgccg gggacgttga    6120
tgctggccat ccggtcgagc cggtactcgc cgttctcgag cagaatcgtg gtgcgcggct    6180
tgacgcgttc gagcgcctgc agcagctcgg acgtccgccg cacggtgacg acctgtttcg    6240 tcgccgcgc cgcccatccg cagaagtgcg gcaccggcgc ggcggcctgg ccggacggca    6300
gaagcgccac gagtgcgccg gccacgatga ggcgagtcat gccgccaccg tgtcgacgtc    6360
gtgttcgcgc aaccgagct cgaggatgag caggatttga aggaggtagc cgcgcgactg    6420
tctcccgtga cgcgtgtcgt cgatgatggc gcgcaacgtc tcggggcgca ggaacatccg    6480
cgtgcgcgcc tccggggcga acagctcgcg ctcgacggct tcgagcagtc gcgtctgcag    6540
ccagcgatcg aagtcgtgat agtgacggta cccaggcgcg ttcaggcgct tcagcagggt    6600
gttgaccttg tcgaacacct tctccgccag cggaccggcg tcgccgcgcg cgccggtgtt    6660
cgagttccgc accttgagca cgccgggtt ccggcctgc gtgatcgcgc gatgaagcgc    6720
cgtgtcgtcg cgccatgccg gatcgccgct cagcaggacc tgcaggaact cgcgatccat    6780
gaacggcagc cgcacgtcca cgacggtgcg gaagagatcg agcgagggaa tcgtgaagcg    6840
ccgatgatgc tcacgaagat agagatagct gctgagctcc gcgggtgaga gctccacggt    6900
gtcgaggagc gcgtgcagcg agtcggccgc gccccgtccg gagaggcgcg cagcgtctgc    6960
tgtgaagagc gtgtccagcg gcaggccgct gctgatgtag ttggcgcgcg acgtcatgta    7020
gtcgatgaac tcgccgcggc ccgtcatcgc gaacacgtgg ccgtcggtgt ggagcggcca    7080
cgccaggctc gtcttggcga gctctccgcc gtggccgcgc agcaggacct cgataccgga    7140
gtcccgcagg aaatcgatcg ccagcatctc ggtcagtccg tggctcagat acatgccatc    7200
ggtgagcgag accatgcgcg cctggttcgg cagaaagtcc ttgaggtacc ggtcgtcgag    7260
ctcgaagaag cggtggtcgg taccggtgag cttcgacagc tgttgcgcga tcacctgatc    7320
ggcgcagccg gcgacgccca gcgtgtacgt gatgagcccg ccaacaccgt tcaccgcact    7380
cagcacggcg cggctgtcga ggccgccgga gagcgacagc ccgaagcgat gcctgcccga    7440
gagcgacttc tcgaccgcgc gcctgaacgt cgtgtgcacc gcgtggacgt acgcgtcctt    7500
cgtcgtacgc ggtccgcggt agagatcggc cggctcgaaa taccgggaca cgctcgcggc    7560
gcctgacggc cagtcgtacg cgagcacggc gccggggtcg aggagcgtga cgcccgccgc    7620
```

-continued

```
cagggtcttg tcgcccagga cgaagcccag cgtgacgtaa tcggcggccg cccggaggct    7680
gagagccggt ttgcgcgccg aggtcctgag cacggaagcc agatccgatc cgaacgacag    7740
tccggccgcg tcgacccgcc agtagatcgg atacgagccg aacggatccg ttgcaagcag    7800
cactcgctct cgccgcggat cgatcacggc gagcgaaaac gcgccgtcga gccgggcggc    7860
catggcaggc cccagccgtt cgtacaccaa agccaggaga tcggcgcgcg tcccgttcgc    7920
cgaaccaaac tcgctccgga gcgccgcttc gttgtagaga tcgccgcgaa agatcaccag    7980
cggccggctg acgtcgcgcc cggccgccac ctcgtcgagg aagccgagcg tgccgagccc    8040
gaccgcccat cggtccgacg gatctcgata gacgaccgtg cggcgcggcc tgcccgactt    8100
cgccgctgac gcggcgtcgg cgcggctgaa ggcggtagat gccggctcat cgcggcaaac    8160
gacgccgagg aggccgttca tcagacgacc ccgcgggcag acacgcgcga cggaacaaga    8220
ggtgtcgtct gagcggccgg aaccggccgc gcggcgtgcg ccgccaccat ccggttgagc    8280
gcaatcgaca agccgaggaa gtgccagagg atctcggtgt actgaaagat gacgaacgtt    8340
ccgcccacgc agaatgcaat gagggcggtc tggacggcca gcgcgtacgg cgccagctcg    8400
gccagggccg gatcccgctt cgagacccgg cggaccctgc ggcaggcgat gagcgccagg    8460
aggagagtga gcaggaacgc cgcgaggccc acgaacccaa gctcagccac gagaccgaac    8520
cacgcgctgt gaaccgagcg ccccttgccc caggcgccgt ccgacgtgtc gtagtcgttg    8580
taggcggccg tgaaggcatt gtgaccgacg ccgtaaatcg gccggtcatc ggccatgcgg    8640
agcgcgaccc tccagaagtg cagccggctc tgggccgatc gctgatcgcc aaccgccgtg    8700
tcgctcgcgt cgatgctcga gtcggacgag ctgatcgagc tcatgcgatc ccagaactct    8760
tccgtcatca cgagcgacat cgcgacgaag accgccgccc cggccacgag gacgagcatc    8820
ttgcgcttcg agtacaggaa atagacgagg ccaagcacgg cgagcgtgag gaagccgccc    8880
cgggagtacg tgctgatgcc gcgatagagc accccgatga gcagcacgcc cagcgcccac    8940
ttggcccatt tcctcgcttc cgtctgcatc agcgtgacga tgagcggcac gagcatgaac    9000
atgccgacgg cgacgccgtt gttgtcaccg agcgagtaga cgtcgttgaa gttcttgatg    9060
ccgggaatga acaggagctg accccagccc tgcttggcgg cctcgaaccc gagggagagc    9120
gagatcacga ggaagacgag ccgcaaccgc ttgacgtccg tcgtgaggac tgcgagcagg    9180
tacgtcatca cggtggactt catgaagtcg atcatgtagc cccacgcgaa gtcctggtag    9240
ggcgacgcca gcgtcgacga caggctgtgg agcccgaaga aggcgaggag cgccagccgc    9300
gcgtcgatcc gcagcgcctg cccggacagg aacgcgatcg cgagcgtgta catgcccgcc    9360
aggagcgaga tgttcatgtg gatgagaaag tcgctccaca cccagagctc cggccggaag    9420
tacgcgatga acaggtagaa cagaatcgcg tagaacggcc cgcgcagcgc gtggaaggcg    9480
ccgaaggcga ggagggcgag gacgaaagcg gctcgaagca ttgccgtgtg ttacctgtta    9540
tcggtcccga tggtccagag cggctgcgtc cgggtctcct ctacattgaa caccttgtag    9600
agggccggaa tcgaggtgaa catgagcacc acgaaaagaa tcgccgacac caccatgtag    9660
gcgaagaacc cccgctgctt gtagagcttc tccggattct gcacggggct gttcggcagc    9720
atcccgatgt gcaggtagta ggcgaacatg cccgccgcca ccggcgcgaa caggatcagc    9780
tcgaggtgat agcggacgat gaagatgccg ccgaagaggg cgcagcaggt ggcgtagaac    9840
accatgctca cgagcagccg ctcctcgttg tagaaggcaa acgacttccg gtacgaggcc    9900
gcgaccgacg cgttgccgat gtgccggaac tccgcgtacc gcttcgtcgc catgaagaac    9960
gcgcccacca tccagtacga gatcacgagc gacatcggcg gcacgcgatc ctgaatcagc   10020
```

```
gggaaccagc cgaggaggag ccggacggcg ttgttcgccg actcgctcag cacgtcgagg    10080
tacggccact ccttcgtgcg aatgggcggc acgttgtacg tgacgccgag cacccagagc    10140
gccagggccg acagcgcgaa gtatctgttc acgagcagcg cgagcacgaa tccggccacg    10200
cccacgagga tccactcggt gtagcccgcc gccggcttga tcttcccgga gggcaccggc    10260
cggtgccgtt tctccggatg cagcagatct ctcgggccgt ccaggagctc gttcagcacg    10320
tagttgctcg aggcgatgag gcaggtgcgc gcgagcgcga gcgcgagcgg cgggacggcg    10380
gtccagccga agagctgcgg ttcgtagaag aacgccagca gcacgccgag cagcatgaac    10440
gcgttcttga accagtgatc gatccgcgcg atctggacgt acggccaaat ccgcgaaccg    10500
gagctagcgg ctgacgacat cgttgagctc ctcgagccgc cggatcgcga accatccgcg    10560
gccggctgtg acgccgtggc ggccggcgat gagggcgcag gagagtcctg cggccatcgc    10620
tccttctccg tccacgtccg gtcgatcccc gacatacagg acctcccgag gtccgagtga    10680
ccacatctca cacgccacat ggaagccgcg cgggtgcggc ttcagggcgt tcacgttgct    10740
ggcggtcgtg cagagcgcca gcgaaaaatg ctgcgacgtg ccgagcgcgg cgagcttgct    10800
ctcgggcgcg tagtccgaca gcacgccgag cctgagcccc gccgcgcgaa gcgagtcgag    10860
cgcgccgagc aaccccgggc gccggcacca ccgcagatac ttgagcggcc ggcgcaccat    10920
ccattcgttc accgtcgccg ccacgacctc gttgtccagc ccgagcgcct gcgcggtgcg    10980
cgcgatctgg cgcgccgcga gcggctcgtc ggccgcgccc aggcgccgga tcctcatg    11040 cgcccggcgg tactcccgca cgatgcgcgc cgtgtccact ccgcgccgcc accggaacgt    11100
cacgagcggc gtggcggcga gctccgctgc catggcggcg cgcaacggac cctgccggta    11160
cagcgtgccg tccacgtcga acagcacggc cttgaccccg cgcaacggct tcactctgcg    11220
aggcccagca tccgcagaat cgccgacacc tttgacgcgt cgcgaaggaa cacgtcacga    11280
acccacacgg cagccagccc cgccaacagc accgccgctg ccgcgcccgc tgccgtccgc    11340
cagctcccgc gccaggcgcg cgtgtcgatc gcggcggcgc cgtagcagag cagaatcggg    11400
acgagcggca ggtgataccg gggatgtccg aagacgatcg cgtgaatgcc gctcatgaac    11460
acgatcaggc tcaggagcag caggtgcgcg cgccagttga ccggccgcgc gaacgagatg    11520
ccgatgacgc cgagcaccat gaccgccgcg tacgatccca tgatggacac cgccccggcg    11580
aagaacagcc accgcggcgg acggtagaac ccatttccga cgccggcgat gaagtcgcgc    11640
tccagccccc agaagtctgc gaacttcagc accgaacggc gaagcgtcgt tcccggatgg    11700
gccttcatgt agtcgagcgc ctggcgctgc gcccacttct ctttcgtgcc ctccgtccag    11760
cggctgccgt ccggcgcgcg aggcggcatc gtgcgcgacc attccttgtc gcccgtgagc    11820
gagatcgcgt cccacatgcg atcctcgggc gtgtacgcgt agttgcccat catcaggttc    11880
agcccgccga gcgtgtccac gaccgtgaac gagcgttgca ggagcgtgtt gcgcacgctc    11940
cacgggccga cgatcgcggc gtatccggcg aagagaagca cggccacgcg cagacgcgcg    12000
cgaagcggga tgcccagacc gacgagcgcc gcggccatga ggatcgcgac gtacggccac    12060
atgatcgagc gaacgagcgc ggacgcgccg agcgcgacgc ccgtcgcgag cgcgatccac    12120
gccgagtgcc gccctgatgg gcgatcgatg agcgtcagac atcccaagag caacaaaaga    12180
aggagtgtga tgaagagcgt ctcggacagc accagcacgc cggagaacag cagcgaggga    12240
tagaacgcga acgccgccgc ggcaatgagg ccggcgcgtg cgctgaacaa cctgcgcccg    12300
atgagataca cgaccagac accgagcagg ctcaacggaa cctgcgccag ccggaccgcc    12360
gtcagcgatt ccgagcccgt gaccgcccag acgcccgcga cgaacgcggg aaagagcggc    12420
```

```
gcccggatgg acgtcggttc ccccggcccc cacgcgaacc cgttcccggc gacgacgttt   12480
ctggcaagcg tcgcgtagtg ctgctcgtcg cgaatctcga gcgcgacgtc cttgaacccc   12540
caaatcaggc cgagccggag gaccagggcc agcgtgagga tgacgagaat tgcccggcgc   12600
tcccaatggg tgcgctcggc ctcgtcgcgc cggggggcga cgattggcca gggggccgac   12660
gatgggagtg ggggagcctg catcattcgc taaaacaagc agttacggtc aaacctgtgc   12720
caccggggaa tcagcaaaga ctctgccaac gggtccgccg gcggcgacgc ccggcgcgcg   12780 tttccggcc ggaagtcggc ccccaaggcg acccggctgg gcacagccca gtagaaatct   12840
cattctggga tgacttttgt ccatgatcca tgaccatttc gaggggcctt cgtgacgccc   12900
tggggatggc ataagcttgg cacctgcgat ggcgacgtgt cgatgatcag cggccgtgag   12960
gagctccaga aggcctatcg gacgaccgg gtcgcccgtg aatacgtggc gcggcggttc   13020
cagtcaccgc tgggggcgct cctccattcg cgtcagatcg gggtcgtgcg agagctcgtc   13080
cgcgcgcagg gcatccggcg cgcggcggag atcgcacccg gtccagcgcg gctgaccgtg   13140
gacatcgcgc cgctcctcga ccgcgtgacg ctcgtcgacg cgagcgccca gatgcttcac   13200
gaagcgcgcg agcggctgcg cgaccggacg ctcgccgcgc gggccaatct cgtgcaggcc   13260
gacgcgtttc gtctgccgct cagcgggccg ttcgatctcg tctacacctt caggctcgtg   13320
cgccatttcg agcgcgccga tcggctgcga ctctaccgcc agattgcgac gattctcgga   13380
cccggcggct ggctcgtctt cgatgcggtg aatgagattg tgtctgcgcc gcttcgcgcc   13440
aacgcgaagc ccggcgagta cgagcactac gatgcgctgc tcacaccggc cgggctacgc   13500
gacgagctgg ccgaggccgg gttcacgatg gtgtcgctca ccggtgcgca tcgccggttc   13560
cccacgctca tgaagtgcca gatgtatctc gcgccgaggt caacggtgct cgcgcgcgcg   13620
gcgatggagg tgatcgatcg gctcggcggc gaaccgctcg agtggatcgt cgtatgccgc   13680
cgcgggtgac ctactggacg ggtacctggg atccgatcaa agaagcgatt tcgaaggaag   13740
tgaacgccct ccgcaccggg tcgcgggcga acgcgacggt cgtgtcgttc tcgccggccc   13800
agcgcagccg tctcgtgccg aaagatcgcg tgctcgtgtt gtccggccgc gcctggatcg   13860
cccttcgggc cgcggccgcc gtgctcgagc gcgcggcga cgtgacgcac gtcttcggcg   13920
gcgggttctc ctggcatctc ctgagggcgc tggggcggcg gccggttctg ctcaccgccg   13980
tcaaggaaga tggcgctgcc gatctgcccg gggcgatcgc gcacgtggcc gtcgaagtcg   14040
gccgcgctcg cgacacgtgg atcgcggccg gtatgtctcc cggccgcgtg cacctcattc   14100 atccggcgt ggacctcgac tggtatcggc cggtgccggt ctcgtcggag agattcacgc   14160
tgctcttcgc cagcacgccg tccgatccgg ctgagatcga gccgcgcggc attccgctcg   14220
tcgtcgagct ggcgcggctc cgtccggaga tcgacgtgct ggtgccgtgg cgccggtggg   14280
gcgacgtcga cgcctccagg cgcgcgctcg acgccctccg tccgccaccg aacttcatcg   14340
tctcgtacga ggacgcaccc gacatgcgcg cctgttacgc gcgggcgcac gccaccgtcg   14400
tgtgcttcgc gggcggcacc ggcaaggcct gtccgaattt cgtgctcgag ggattggcca   14460
tgggacggcc gtgtctctcg acgcgcgaga acggcatcgc ggagatcctc gatcgatcgg   14520
gcgccggcat catcgccgcg cgcgatgccg cgtcgctcgc cgcgagcctg acacgctcc   14580 gcgccggctg ggccggctgc gccgagcgcg cgcgccggct cgcagaggag acgttcgacc   14640
tcggccgctt ccgccgccgc tacgacgcgc tgtacgtgga ggtggcatcc gccgccgctg   14700
gcgagcacgc gaggcgcgcc tcttgacgaa gggactcgcc ggacggctgc tcgggtgggc   14760
tcagaaggcg aacgatttcg ccgactacgt ccgccatcga tcgcagatga agcgcgacgc   14820
```

```
gcgggcgaat cgccgcaggc tccatcgggc gctcggcggc cgcgtgaacc ggatcctcat    14880
cgtgcggctg ccagcatcg gcgacgtcgc gcgcgcgacg ggcgtcctcg gggccctgcg    14940
cgcgcagtac ccgcaggcga cgatcgactt cctgacgtcg gacgcgaccg tggccgtcat    15000
ccggcaccac cccgcgatca acaccgtcta cacgctccag gatctgtcgc gcctgtccga    15060
gtacgactgg atcatcaacc tccagaacct cgtgccgccg gcgagctttc tcagaacgtc    15120
cgggctctcg tacccgcaga ttctcgagca gctctcgagc cgcagccgtt ccaggatcat    15180
caccggccgt cacctcgaga acggctcgga gtccacgccg acgaacatcc tctactgcat    15240
ctgtgagatc gaggagcatt tcctcacggc gctcgtcccg tacgacacgg cccgctaccc    15300
ggtgaccgcg attcacgtgg acgcacaggc acgagcggcg gcacgatcga agttcgcgtt    15360
cccggagaac cgccaggtgc tggcgatctt cctcgggtcc aactcggtcg ggtgcggcgc    15420
cgatgagggc tttcgcacgt actccatcga ctacgtgaag cgcctcgtgc gtcacttcga    15480
agatcggttt gcgatcgcca tcatcgggca gtcccaggtg cgcaacccgg ccgaacgcgc    15540
acagtaccgc gagatgctcg gccgccatcc ggacgtgatc gatctcgtgg acaagacgtc    15600
gctcgacgag ctcgtggccc tcatggactc gttttccctg ctcatcagtt gcgactcgag    15660
ccccgtccat ctggcgatgg cccgcggagt gccggtcatc gggctgtacg tcaacgacgg    15720
gacgttcagg atgcacccga cgctcggcga cgagcgcttc gtggccatca acagcacgcc    15780
gccgtgcttc acctactcgt ggcgatggaa gttcttctgc tcgacgtgcc gcgacccggc    15840
gaccagatcg cattactgtc acaacgaggc gttcgtgttt ggcgtggacc gcattccgct    15900
ggccgcaatc gaccgcgcgg cggcgcggtt gctcaagggg agctccgatg caggacctca    15960
ttcgcgcgca gtttgaagag tcgatcgaga cgaagcgcaa agcgctctcg ctcgtcgatg    16020
cggtggccga gtcggcgcgc ctcctcatcg aggcgctcga ggccggacac aagatcctcg    16080
tgtgcggcaa cggcggctcg gccgccgact cgcagcattt cgccgccgag ctcgtgggcc    16140
gcttcgagaa ggagcgccgc gcgttgcctg ccgtggcgct cacgaccgac acgtcgatcc    16200
tcaccgcgtg gccgaacgac tacgcgtacg agaccgtgtc agccggcagg tgagtgcctc    16260
ggagcgccgg gcgacgtgct catcggcatc acgacgtccg gcaactcgcc caacatcctc    16320
gccgccatgg acgaggcgga aaagaaacgc atgaaacgaa tcgcgctcac cggacgcggc    16380
ggcggcaaga tgaagagtct cgccggcgtc tgccaggtca tcgtcccgtc agatcagacg    16440
tcgaggatcc aggaagtaca cattaccgtc atccacatct gggcgaagtt gatcgagaaa    16500
gcgctcagct gagctggcgg tagacgtcga acgtgcgatc ttcgaacgtc gaccaggagt    16560
gctcgcgggc gatgaggtcg gcggcggcgt cggtgaggcg gcggcggagg tgctgatcct    16620
cgaacaacag ttgcagtcga ttcgcgtagc cctcggcgtc gtccgcctgg acgagaaagc    16680
cggtcttccc gtcttccacg acttcacgca cgcccgggat ggtggagccg atcacgggca    16740
cgcgggccga ctgggcttcg agcaccgaga gcggcagccc ctcgtgcgtt gacggcagca    16800
ggaaggcgtc ggcggcctgg agcagcaccg gcgcgtcctg gcggaagccg agaaagcgca    16860
cgcgatcctc gagcgcgagc tcggcagaga ggcgcctcag cgcctgctcg tgttccttgc    16920
cctcggtccg gtcgctcccg accagccagc actcgaccgg caggccgcgc gacatcagca    16980
gcctggtcgc ccggattgcc gtagcctgcc ctttgtgtgg cgcaagattc gcgagcatga    17040
ggacgacgaa gcggtcggtc tcgaggccgg cggccgtacg cgcggcttgc cggtcgccgg    17100
ccacgaactt ctcccgatcg accgcgttcg gaatcgcggt gaccggcacc ttgtcccggc    17160
gtccctgctg cgccgcgtcg atcatcacgg cgatgtagcg cgcacacgtg acgatgtgct    17220
```

```
gcggcgggct cttcaggacc caggcgatct cctcgggatc cggttcgatg tgaaagtgca    17280
cggccacgcg cgccgcgcgcg gcctgcagcg cgggtctcat gaatccgtac acgacaggat   17340
tgtgcacgtg gaccaggggc cgcccgacga gacccaatcc ggaagcatg cgcgcacacg     17400 cggcgagctg ttgcaggccg ccggcccgca gcgcgttcag gtcatacatc cgccgccgga    17460
cgccctccgc gtcgagcgcg gcgcccgcag gaccctcgcc tgtaatccat gccgtgcacg    17520
ggacgccgcg gcgtttggcg gcggccgaca accggatcgc cagcaccgcc gcgccgccga    17580
ccagatgtga gacgaggatc tcgtgcaggc gggggactg attcatggtg gcgcgcgatg     17640
cggccgggcc gccagcctac gttactcgcg tcgcaggtcc gcccgcgcgg tagagcgagc    17700
gcagcaggct gcgaagtccc gacgggagga agcacacggc gtaccgcgtg agatcggtgc    17760
gccgcatcgg caggcccgcc tgaccgaacc gtttccgcgc cgcgtgaaac tcgccgcggt    17820
cgtactcgag gtggccgagc gcgagcagga gacgatggcg atgatcgctg gcggcgcgat    17880
gcgccgactg atcgctcccc cgcgccagga accgctccag cgtcctgacc atgccttcga    17940
gcatcacgat ggacgacttc gacatgttgg tgtcgtgcag cctgtaatgc gtcaggggtt    18000
ccgggatgaa accgaccggg cccttcgccg agaggcgcag ccagaggtcc cagtcctcga    18060
cgccgtggat gccggtcgcg aacatctcct gccggagcac ggcggctttg accatgaccg    18120
acgaagcggt cacggcgttt cgcaggacga ggtcggggag acagcgcccc tcgagcggcg    18180
gaagatcgag cgtgcgcagg acctcgccgg cctcgtcgat gacggcgcgg cccgtatgaa    18240
tgaagctcca gtcggcgtgc tgtcggaaga gatcgacctg ccggcgaatc ttggccggat    18300
cccacgagtc gtcggcgtcg agcagcgcca cgaattcccc tcgcgccgcg gcgatggcgc    18360
gattgcgggc gccggcaagg ccccggttgg cctgagagat caccgtgatg gcgccgccga    18420
atctcgccag gatgtctgcc gtgccgtcgg tcgatccgtc gtcgacgacg atcacttcga    18480
cgggctgata ggtctgggag agcgcggact gcacggccct ggcgatgtag cgctcgccat    18540
tgaacaccgg gacgatcacc gacacgaggc cggggatatc ggtctgggcg gccggcgagg    18600
gctctcgagc ggcttcagcg gccatggccc tctgcactgg cgtcgcgagc gaacagcatg    18660
acgtttctcg aaagccacgg agacaacggc gcgctcttca tccgctcccg cagcgtctgc    18720
gatgccgggc cgaggtagct gaacccgcgt gccgcgaaga tcttctgcca gtactcgagc    18780
ggctgttcgt tgatgtggcc cattccgccc tggcccggct gcgcggcgct gaagagcacc    18840
agcggcgccg tgttcgtgag cacggcgacg agcttctcgc caagcggcgg cggaaggtgt    18900
tcggcgacct cgaggctcat ggagaggtcc gttgcgtccg cggccgtgga caccgccgtg    18960
agatcgaatg agttcagcgc gacgccgagc ttttccgcgg cgtaccgtcg cgcgtactcg    19020
gatcgctcgt agccggccgc cttcacgcct cgtgcgagga acgcgtgcac gaagtgaccg    19080
gtgccgcagc cgaagtcgtt catcgatcgg atgccgggtc gcaacgccag gaccccatca    19140
acgagcacgg gcgccgcctc ggcggcgacg tgcccgaaca gatccatgac ggccgcgttg    19200
tacgtccatc gctcgaagcc cagccgttcg ccgatccggg acatcttcag tccggcctgg    19260
caacgccccg accagtagag ccgcttgagc tgggtcacga tcatgggttc gtcccgggcg    19320
cgacgcgaac gcgcggcggc gcatgcagcg acgccgagaa ctccacatcg gccacgccgg    19380
cccacgatcg atgttccttg accgccagcg tcgcaagctg ccgcgacggc acgaggaacg    19440
tctgggtcgg gttgtgaaac acgtgcaccg acaggtagta gtggccgcga acgagatgcg    19500
cgcggaaatg gaggtcgagc gagaactcgc ccatgaacgc ggacgcgtcc ccgagatccc    19560
gccggtggat gttgccgtcg tagacgacga gctgatcggt ggagcgttgc accatgaagc    19620
```

-continued

```
cgaacgtgac gtcgtccagc ggctcggtac ttctcgcggt gacctggagg ttcagctgct    19680
tccccggcgt cacttcgctg tgcgtgcccg acgactcgtc gccgacgaag agcgagccgc    19740
acacgatctc gacggggctc ccgacactcg gctgttccga tttcctggac gcgcggacgt    19800
acgcgtcgag gacttcgatg gccgtgccgg cggccttcac cgagccggcc agatacaccg    19860
catgctcgca gagggtcgcg accgcctgca ggttgtgcga gacgaggacg atcgcgatgc    19920
cctggcgctt gaactcctgc atgcgatcga agcacttctg ctggaacgtc atgtcgccga    19980
cgctcaacac ctcgtcgatg atcagcacgt cgggccgcag gtgcgcggcg atcgagaagc    20040
cgagccgcgc gttcatgccc gacgagtagc gcttgacggg cgtgtccacg aagtcggtga    20100
cgccggcaaa ctcgacgatc tcgtcgaacc gctcggcgat ctcgaccgt ttcatcccca    20160 tgatcgcacc ctggaggaac acgttctcgc gcccggtgag gtcgggatgg aaccccgcgg    20220
cgacttcgat gagcgcgccg gcgcgccccc ggacgatcga gcggccggtc gtcggcttca    20280
ggatcttcgt cagcaccttg agggtggtcg acttgcccgc cccgtttgcg ccgatgatgc    20340
cgagcgcctc gccgcggtgg acttcgaacg agacgtttct gaccgcccag aactcctgtt    20400
cgtccagcgc gtcggcggga cgcggttgaa acagcccgcg cacgagcgcc ggcacgaggt    20460
cccgcaggct gtcatgacgc tcgccccgcc ggaacttctt ggagacgttg tcgaagacga    20520
cgggggccgt cacgtcagac gttctccgcg aattcgaact cggagcgatg gaagaacagc    20580
cagccgaaga cgagcgtcac gaccgagacg atcgccgtga cgcccagcat cacggacggc    20640
ggctggttca ggagcagcac ggcgcggaag ccgtcgatga tcggcgtcat cgggttgagc    20700
tgcagggccc actggagctt gccgcccacc atttcgaccg ggtagaccgt cgacgacgcg    20760
aacatccaga cggcgatgac gacctcgaag aggtatttca cgtcgcggta gaagaggttc    20820
gccatcgaca ggatcagggc gatggccgtg gtgaatatca cgagcacggc gagcacggcc    20880
ggcagccaga ggatgttcgg tccgaccggc acgtggtagt agatcatgag cgcgacgagc    20940
accacggagc cgatcgcgaa gtccacggcg ctcacgatca cggcggagaa cgggaagatc    21000
tccctgggaa agtacacctt cgagacgaga ttcgtgttcc cggtcaggga ggtcacggag    21060
aagcggagcg ccgaggagaa gaagttccag acccacaggc cgcagaacgc gaacaccgga    21120
tacgcgaccg gcgtgtcgat ggccgcgacg cgcatgaaga tcacggagaa gacagccgtg    21180
ttgatgagcg gcatgaacac ggcccacccg aagcccatca ccgactgctt gtagcgcagc    21240
agcaggtcgc gccgcgtcat ctgcatcagc agctcgcgat actcgaactg ctcggcgagc    21300
atctcacggc aatcgccag gaaggcgcgc atcgtcagcg gtgtcagtcg cggcgtcgtg    21360
ccgggcggat catgagggca ggtagcgctc gagctgcccg aagagcaact gcacgaactc    21420
ggtcgcgcgc cgctcggcgg cgacgtcgcc gttttcgctc gacggcacgg ggctcgtcac    21480
gcggacgagc gcggcgtccg atcggttcag ccgcatcgcg tcgtacacca tgtagatctt    21540
gctccagtac tcgctggcga tcacgcgcc gtggctctgg taccagtaca gcacgatttg    21600
ccgctcgatc cccttctgga tgacgtatcg gttgatctcg atgggctcgg tgcggcccgg    21660
caccttgacc agcgcgcggc cggtggatac gggctcccag ccggcgcccg gcaggcagtt    21720
catcggcgag tggatcgtgt cgccttcgcg ctggctctgg tagtagccga tgtagagcga    21780
cacgtagggc tcgcgcggcg ccaggtagat ccggttgatg tactcgtcca cgccgagcac    21840
cgccatgacg tccttggtga agggcgcgct gtcgcgtccg gtccaccgct ccatctggaa    21900
cgggacgttc gcgagcggct ggcgaagcgg gacctgctcg gcgcgcatcg agcgcgcggc    21960
aaacgccgcc gtgccgagga aacacacgct gagaatgatc agtcgtctgg tcatgaatct    22020
```

```
ggactcacac cgtggccggc gcggtcaccg ctcggggcgg aggcgtgaag cgccgcagga    22080
cccagaccac gacgaacaac atgacgaacg cggcaagaaa gacgagccag cccgagaacg    22140
tgtggaagaa cccctgcgcc gcggcctcgc cgtagtagtg cgccgccacg cccgtgccgg    22200
ccacacgcgc gccgttcgcg ataatcgcga tcgggatcgt cgagagcgca atcgccaggc    22260
gcatgccgac gcgcggatcc gtgaagtagc cgtacacgat gcccagcgtg agcagcgaga    22320
tgagcgaccg gatcccgctg cacgcctcgg ccacttcgag cgtcgtgtgc gcgagcacga    22380
tcacgttgcc ttcgcgcagc accgggatgc tgagcgcgga cagcacgccc tcgcccacgc    22440
gagacgccag gagctgcagc ggaaatgcga tctgattgaa gatgatcgac gggatcggga    22500
tcatcagcac caggaacgcg agcggaaacg cgagcaccca gagcttgcgc cagccgagca    22560
ggaacacgat cgcgccggta agcgaggcta gtatcgacac gcgcgtcaga aagagctcgg    22620
cgccgagcaa ccccgcgacg agcagcgcga gcccggcgag cacgatgacg agaccgagcg    22680
cgctcggcgt gtccggcagc gccgagagac gcgcccggcg ctcccaggca aagtaggccg    22740
cgagcggtac gatcagaatc ccgtgggagt agttgtcgtc gttgatccag tcctgcgcca    22800
accgcacgat cacctgccca taaaggagca ggaaactcac ggcggcgata ccgagcggaa    22860
ccagtctggc ctgaagcaca ctcatagcga tcgggacgaa tatagcaaag ggctctcccg    22920
ggcagaactt gggcgccgaa acacgtaacc atcacgctca caggaagtta gcggctaaat    22980
gacgggattg gccggctgga ggggcctcgt gaatctaccc aatggatgac aaatatccct    23040
atcaactcct cctttttgact gcgtagcacg gaagatcatc ggcctcttca gatgcaggac    23100
aaatgtcatc tgtcaggaag agtaatgtct ctggccacag cgccggtcaa gtgaaatccc    23160
ccgacagaat cgcgtaccac cgcgactggc atccggcgag aaaagtcgcc tcgtcggccc    23220
gaaaactgca ttacaggaac gccaggtcgg cagccggttc gttttccgtc agtattttg    23280 ggcattgcag gcgctttcgt ctgccggggg gcggaaccgt gcgaccgggc cgatcacgcg    23340
tggagcaggg cagggacagg catggatggt tccgtgagac agccgcgttc gggagacggc    23400
cgggctcggc gggagctcgt ccacctggcc gtggaccgcg cggcgcgcca atttcctgac    23460
gcgccggccg taagttttga cggcgtctcg ctctcgtatc gcggcctgac tcgccgcgcc    23520
aacgcgctcg cgcaccgcct gcagcgtcat ggcgtcgatc ctgacgtggt ggtcggcatc    23580
tccctcgacc ggtccatcga gctcatcgtc gggatcctcg ccgtgctcaa ggccggcggc    23640
gcctacgcgc cgctcgatcc tgcgtatccg aaggaccgcc tcgagtacat ggtcagggac    23700
gccggggcgc ggatcgtgct cacctcgcga cgcgtgagcg gtctgatccg cgtcgatggg    23760
gtcgagctca tctgcctcga tgcggacgag cccggggcgt tggcggaaga gggccatgcg    23820
ccggacgccg gcgtcgatct cgaccacctc gcgtacgtca tctacacctc gggatcgacc    23880
gggcgcccga agggcgtcgc gatgccgcat cgtccgttgg cgaatctcat cggctggcag    23940
gtcgacgcat cggccgtcgg cgccggcgcg cgcacgctcc agttcacttc gccgagcttc    24000
gacgtctcgt tccaggaaat ctttgcgacg ctcgcgaccg gcggcgagct cgtgctcgtg    24060
tccgaggaca cgcgccggga tccgcgcgcg ctgctgcggg tgctgcgcga tcgatccgtc    24120
gcccggctgt atctcccgtt cgtcgcgttg cagcagcttg ccgtcaccgg caccgacgat    24180
ccggatctgc cggcgttgcg tgaggtcatc acggccggcg agcagctccg ctcgacgccc    24240
gcgctcgtcc agtggttcgc gcggcatccg cagtgcacgc tccacaacca ctacggcccg    24300
gccgaagcgc atgtcgtcac tgcgcacacg ctgactagcc ccccgcggga atggccggcc    24360
ctgccgccga ttggcgtgcc gctgcccggc gtcgagattc tgatcgtcga cgagcatcgc    24420
```

-continued

```
cagcccgtcg cgcacggcaa cgtgggcgag atcctcattg gcggcgtgtg cctcgctcgc   24480
ggctacttga atcagccgca gcgcacggcc gaacggtttc tctcgcatcc gcttcgcccc   24540
gatgctcgcg tgtatcgcac cggcgatctc ggccgtgtgc gcgacgatgg cgcgatcgag   24600
ttcgtcgggc ggacggacga ccaggtgaag attcgaggct ccgtgtggag gccgggcgaa   24660
atcgagaccg tcctccttca gcatcccggt gttcgggaga ccgccgtcgt cgcgcacgac   24720
gacgcgtcgg gcagcaagag gctggtcgcg tatgtgattc cgtcagccga tcaggcggcc   24780
accggagccg aggcttcggc acaggtctcc ggatggcaga ccgtgtggga ggacacctac   24840
cgcgcggcgc cggactcgac ggatccggcg cttgccgcga ccggctggcg gagcagctac   24900
acggggatgc cctacaccgc ggcggagatg cgggagtggg ccgatgagac cgtcgcgcgc   24960
atccggtcga atgcgccacg cgaggtgctc gagatcggct gcggcacggg catggtgctc   25020
ttccgtctcg cgccccactg cgctgtctat agcgcgacgg atgtctctcg cgccgcgctc   25080
gaccacgtcc gggcccacgc gacggcctgc ggcgccagcc acgtcgagct cctctcgcgc   25140
gaggcggcgg actttaccgg cgttccggcg gccgcgttcg atgccgttgt gatgaactcg   25200
gtcgcgcagc acttgcctgg cgtggactat ctgacgcgcg tcctcgccgg cgccgcccgc   25260
accgtgcgtc cgggcggatt catcttcgtc ggcgacgtgc cgaacctgcg cctgctcgag   25320
atgtttcacg cgtcggtcga gctcacgaaa gcgccggcgg atcttccgat tgccctcgtg   25380
cgcgagcgcg tgcagcgtca gatggcgctc gagcgcgagc tcgtgatcga tccgatgttc   25440
ttcgacgccg tcatggaccg catccccggc atctcgggag cccaggtcca gatccggcag   25500
ggtgccttcg acacggagat gaaccggttc aggtacgacg tcgtgctcac ggtgggcgga   25560
cggccggccg ggcgccgtcc gtccgtcgcg ctcgactggc gtacggagcc ggtcgccgag   25620
cgtcagctcg ggcaactgct cagcgccgat gcgccggacg cgatcgagat caggaacgtg   25680
accaacgcgc ggctcgtcga gccggccgcg tgcttcgatc tcgtcaagcg tgccgactgg   25740
accggcacgg ccggcgagac gcttgagagg gccgccgcgg acacgcgcga cgcgatcgac   25800
ccggaatcgt ggcggcgtct cgcgaacgcc gccggctacg acgccgagtt cacctggtcg   25860
gccgagatcg gcgccatcgg cttcgatgcg cggttcgagc gccggggcac cgcgtcgctc   25920
gccgctcccg tgactcgtca cgcggttccc gccgcggagc cgcgggccat tcagcagtac   25980
gcgacgaatc cgctccgcga tgcggtggcg cggcgcctca cgcccgagct tcggcgattc   26040
ctgcaggagc gcgtgccgga tcacctggtg ccgtcggcct tcgtcgtact cgatgcgatg   26100
ccgctcacgc caagcgggaa gatcgatcgg cgcgcccttc cggcgcccga gagccgccgt   26160
cccgatctgg acgtggcgtt tgccaagccc gccacggagc tcgaacgcaa gatcgcgcag   26220
gtctggcaga cgacgctcca gatctcgtcg gtgggattgc acgacaactt cttcgatctg   26280
ggcgggcact cgctcctgct cgcgcaggcg ttcgagcgta ttcggccgct cgtgccgggc   26340
aagcagtggt cgatgatcga gatgttccag tacccgacgc tctattcgct cgccgggttt   26400
ctcagtgagc ggccggacgc cggcgccggg cagcttgccg gcgcgcagga tcgcggacgc   26460
cgccagcgcg agatgctgac gcgtcagggg cctgccctga gcagagtcga aggggtccgg   26520
taatgcagaa cggcatcgcc ctcgtcggga tggccggccg cttccgggc gcgcggtcga   26580
tcgaggagta ctggcgcaac ctcgtcgccg gcacggagtc gatcacggtc ttcaccaacg   26640
aggagctggc gacggccggg atcagccaga gcgatctgca gaatcccgac tacgtccgcg   26700
cgcgcgggct cgtcccggat ccggaccgct tcgacgccgc gttcttcggc atcagccagc   26760
gcgaagccga gctgatggat ccgcagcacc ggctcttcct cgaggcgtgc tggctcgcgc   26820
```

```
tcgaacacgc ggcgatcgcg ccgcggtcgt tccccggtct catcggcgtg tggggcggca    26880
tgagcacggg gatgacgaac agcacgtacc tgctgtcgaa tctccacagc cacgcgggat    26940
tgctccagcc ggaggacgtg ctgccggcgc tgctcggcaa cgagaacgac tacctcacga    27000
gccgcgtctc gtacaagctg cacctgcgcg gaccgagcat gaacgtgcag accgcgtgct    27060
cgacgtcgct cgtcgcggtg gtgcaggcgt gtcagtcgct gctcacgtgg cagtgtgatg    27120
cggcgctcgc cggcggcgtg tccgtgtcgt tcccgcaaca ggaaggctac gtctacgtcg    27180
agggcggcat cgggtcgcca gacgggcact gccgcgcgtt cgatgcgaac gcccaaggca    27240
cggtcttcag caacgcgtc ggcatcgtcg tcctgcgaag gctcgaggac gcgatcgccg     27300
acgggcagac gatctacgcg gtgatccgcg gatcggcgct gaacaacgac ggctcggcga    27360
aggtcagttt cgcagccccg agcgtggacg gccaggcgga ggtcgtggcc atggcgcaga    27420
gcgccgccga cgtggcgccg cagacgatcg actacgtcga ggcgcacggc accggcacgc    27480
cgctcggaga tccgatcgag gtggctgcgc tcacgaaggc ctttcgcgcc ggcggcgcca    27540
cggagaacgg gttctgcgga ctcggatcgg tcaagagcaa tttcgggcac ctcgactcgg    27600 cggcggcgt cgcggggctg atcaaaacgc gctcgcgct ccatcaccag cagattccgg      27660
cgacgctgca ctacgtcgag cccaacccga agtgtgattt cgccaacagt ccgttcttcg    27720
tgaacgccgc gctgcgacca tggccgcgcc gtggccatcc gcgacgcgcg gccgtgagct    27780
cgttcgggat cggcgggacc aacgcgcacg tcgtgctcga ggaagcgccg cccgccgcgg    27840
agcgaccggg cgccgagccc gccagcgacc tgctcgtgat ctcggcgaag acgccggcgg    27900
cactcgacgc ggcggctgcg aacctcgcga gtcatctcga ggcgcacccg gacgtcagca    27960
tcgccgacgt ggcgcacacg ctgcgcgccg gccgacagga gtttccgcat cgacgagcgc    28020
tcgcctgcac cagccgcacc gatgcgatcg ccgtgttgcg cggcgcggac gccaaacgtg    28080
tcgccaccgg cgacgccgaa tccggcagcc gtgccgtggc cttcatgttc tccggcggcg    28140
gcacgcagta cgcgaacatg ggccgggagt tgctgccggt cgcgcaggtc ttccgcgaag    28200
aaaccgagcg ctgcctcacg cacctgtcac tctccgccga cgtccgccgt gcgctgtttc    28260
cggatcatgc ggacgtcgag cgggccgcgc attggctcga agctccgtcc gttggtttgc    28320
ccgcgctctt tgtcgtgcag tacgcgctcg cccgtcagtg gatggcgtgg ggtgtgcagc    28380
ccgacgggct catcggtcac agcatgggcg agtacacggc cgcgtgcctt gcgggcgtga    28440
tgtcgctcga gaacgcgctc gcgctcgtgt gtctgagagg ccggctgttc gagacgcttc    28500
cggcggggga gatgctcggc gtcccgcttc ccgaggcaga ggtgcggccc gcgctcggcg    28560
atggactcgc gatcgccgcg gtgaatgcgc caagctcgtg cgtcgtttcc ggcgcgcccg    28620
acgcgctcgc ggccttttgcg cgcgtgatgg ccgaggccgg tgtcgaatgc cgccgcctcc    28680
acatcgcggt cgcggcgcac tcgccgatgg tcgatccgat cctggcggag ttcgagcgtt    28740
tcctccgcgg catcgcgctc gacgcgccaa gggttccagt cgtgtcgaac ctcagcggct    28800
cgtggctgac cgcggacgaa gcgaggtcgc cgcagtactg gacgcggcat ctgagacaaa    28860
ccgtcaggtt cttcgacggg ctcggcacgc tgctcgccga gccgaatcgg gtgctcctcg    28920
aagtcgggcc cggacagacg ctgtccggat tcgcacggca gcatccacag aaaacgcgg    28980 cgcacgtcgt tcaagcgacg ctccggcacg ccaaggaacc ggcgccggac gtcttgttcc    29040
tgcagcaggc ggtgggcagg ctctggacgg caggggtgcc cgtgaactgg gctgcttaca    29100
acagaggcga gggcaggcgt cgtgtgccgc ttccggccta tccgttcgag aagaagcggt    29160
acctggtcga atcgccccag gcgccggtcc cagcgccgct tcaagccctg cgccaaggg    29220
```

-continued

```
ccgatgctac tcagcagatg acgacaactg tgccttcgtc tccggcccga tcgcgtgccg   29280
atcgtatccg cgagcggctg accgaaatcc tgcacaaact gagcggcctc ccggcaggcg   29340
agatcgatcc cgcgctgtcg tttctggaga tgggattcga ctcgttgttc ctgacgcagg   29400
cgagtctgcg gttcaaggcg gagttcaagg tccggatcac gttccgccag ctcttcgaag   29460
aggcaccgac gatcgacgcg ctcacgagct acatcgacgc caagctgcct gcggacgcgt   29520
ttcctgcgcc ggcggaagcc gctccggcgc ctttcgtggc cgcaagcgtg ctgtccgcgg   29580
gccctcatgc ggccctggct ggcgtgccgg cggccgcgcc cggcacgctg cagcacgtga   29640
ttcaacagca attgcagttg atggccgagc aactccgcat gctgggcgga aatcccgccc   29700
tgctgcccgc gatgccgccg ccagcgtcgt ccgtcgcggc ggccgacgcg ggactgaagt   29760
cccgcgctac gacggcgccc gtctcgaagc cgcatgcggc cttcaagccg atcgacggca   29820
aagccagtgc ggagctgtcg cccgagcaga tggccgcgct cgccgcctgg atcgatcgat   29880
acacacggcg cacggccgga tcgaagcgac gcctggccga gtaccggccg gtgcttgccg   29940
atccacgctc ggtcgccgga ttcaaccggc tctggaagga gatgatctac ccgatcatca   30000
ccgaccggtc ggaaggatcg aaggtctggg acgtcgacgg caacgagtac gtggatctcg   30060
tgggcgggtt cggctcgctt ctgttcggac accgttcgcc gatcgtggtc gacgccgtgg   30120
aggaacaact ccaccggggg ttcgagctcg gaccgttgcc gccgctcgcc ggcgaggtcg   30180
cggcgctcgt caaggaattc acggggatgg agcgcgttgg attctccaac accggctccg   30240
aagccgtgct ggcggccacg cgttttgccc gaacggtcac cgggcgcgac aagatcgccg   30300
tcttcgaagg gtcgtatcac ggtctccttg acgaagtgct cagccggccg ctcgtggtga   30360
acggcgaatt gcgtcggcc cccgcggcgc ccggcatcgc cggcagcgcg gtgagcgaag   30420
tcatcctgct cgagtacgcg aacccgaagt cgctcgaggt catccgcgcg cacgagtcgg   30480
agatcgccgc gatcctcgtc gagcccgtgc agagccggcg gctcgacctg cagccgaagg   30540
agttcctgca cgaggttcgc cgcgtggcgg acagatcgg cgccgcgctg atcttcgacg   30600
aagtcatcac cggcttccgc gtgcatcccg gcggcgccca ggcgcacttc ggcgtccgcg   30660
cggatcttgc cgcctacggc aaggtcgtcg gcggcggcat gcccatcggc atcgtcgcgg   30720
gcaatgcgaa gttcatggac gcgttcgacg gcggccactg ggagtacggc gacgggtcgt   30780
tcccggaggt gggggtcacg tactttgccg gcacgttcat gcggcatccg ctcgcgctcg   30840
ccgctgcgaa ggccgtgctg acgtacatga agtcgcaggg tcccggcctg cagacgcggc   30900
tggcagatcg gatcgagcgg ctcgcgaacg acgcgcgcgc gatcgtggcc aggcacggcg   30960
cgccgtatca gattacgcag ttcagctcga tgatgagcct gaacttcccg cacgaccaga   31020
agacggcggt gctgctgttc ttcctgatgc gcgagcgcgg gattcatatc tgggagggcc   31080
gtcccttctt cttcacgacg gctcacaccg aggccgacta cgccgccatc ctccgcgcgc   31140
tcgacgagtc gctggccgag atgcaggcgg ctggcttctt cggcgcgccc gcccactccg   31200
cattgcaggt gaccgggacg gcggaccagg acgtcctgcc gttcaccgaa ggacagcagg   31260
agatctggct cggcggccag atgggcgagg cggcatcacg cgcctacaac gaagtcgtcg   31320
cgctcgacct gcgcgggcct ctgaatcgcg cggcgatgca gcgcgccgtc gacgaggtcg   31380
tcgcgcgtca cgaatcgctg cgcatgacgg tggccagcga accgctcggc ctgcgtcacg   31440
ttccgggcac gtcggtgccg gttgaatggc aggacgtgtc gggattgccg gaggacgctc   31500
agcacgaggc cgtgcagaag gtgctcgagg gcggcgacgg cgtggcgttt gacgtggaac   31560
gcgggccgtt gctgcgcgtg accaccatga cgctcacccc cgagcatcac gtcttcgtca   31620
```

```
tggcggccca ccatctcgtg tgtgacggct ggtcgttcgg cgtcatcctg cgcgatctgg   31680
cgacgttcta ttcggcccag gttcgaggca cgcgtgcgaa cctcgaggcg ccgatgcagg   31740
tgagccgctt cgcgcgtgag gatcgcgagg ccaagcagag tcctgaagcg gccgagaccg   31800
aggcgttctg gatccggcaa ttcgacaccg tccccgagcc gctcgagtta cccgccgatc   31860
ggccgcggcc gccagtgaag tcgtaccagg gcgcccgtgt gtccgtgccg tttgacgcgg   31920
cgctcgctcg cggcgccaag aagctcgccc cgaacaccg cacgaccctg tttacgacgc    31980
tgctcggcgt cttcgagacg ctcgtctacc gactgaccgg ccagcaggat ttcgtcgtcg   32040
gcatcccggt cgcggtgcag cctctgctcg gcgaggatct ggtcgcgcac tgcgtcaact   32100
tcgtgccgct tcgcgcgcgc gtgtcaccca ccgcgacgtt ctcggagtac ctgaacacgc   32160
tgaggacgca gtcactcgac ctcaatgagc accagaactt cacgtacggc agtttgctcg   32220
ccaagctgcg gttgccgaag cacccgggcc gcgatccgct cgtctcgacg agcttcacgc   32280
tcgagcccgc catcgtcgat cccggggttcg acggtctcac ggcgcgttcg ctgacggttc   32340
cgcgcgtgac atcgaagcgc gacctgcacg tgaacgtcat ggagatggac ggcggtctgc   32400
tggtcgaggc cgactacagc accgatctgt tcgacgaacc gacggtgcgc cggtggctgg   32460
atagctatcg gatcctgctc gaggccgtcg tgtcgtcccc cggccggtcc ctcctgagcg   32520
tgccggtgat ctcggagccg gaccggagtc agcttgtcac cggctggaac gacacggccg   32580
ccgactaccc gcgcgatcgc gtcatccatc aactcgttga gagcgcgcc gtgcagaccc     32640
cggagggact cgcgctcgtc tgtggtgccg agcggctgac ctggaccgag ctcaaccgac   32700
gcgcaaaccg gttggcgcat gcgctcgtga agaagggcgt cgcccccggg agcagggtgg   32760
cgctgtgcct ggaacgatcg gccggggttca tcgtctcggt gcttgccgtg cacaaggccg   32820
gcgccgcata tgtaccactc gaccccgtct cgcccggcga tcgcaagtcc ttcgtcgtcg   32880
aggattccgg tgccgtgctg gtcgtgaccg attcgcggtc cgaaggccga tggctgacgc   32940
ccaggacgcc cgtgctccac ctcgacgccg acagtccgcg aatcgcgcaa gagtcgcacg   33000
atgatctgaa ggtcgccctg tcggccgaag acgccgcgta cgtgatctac acgtccggat   33060
cgacgggaca accgaagggc gtcgtcatcg ggcaccgcca gctcgtgaat tacacgtggg   33120
cggtgatcga acggatcggg ttacccgccg gctcgagtta tgcgctcgtg tcgaacgtcg   33180
cggccgatag cggtgtgacc gggctctcgg cgctcgcgat gggctgggtg ctgcacgtga   33240
tcacctcaga ggtcgcgacc gacgggcggg cgctcgggtc gtatttgacc gttcacgaca   33300
tcgacttcct gaagatcacg ccgtcgctgc tcgcgtcgct gctcggcgat cacccgtcgg   33360
cctcgctgct gccgcgccgc tgtctcatgt tgggcggcga gccgtcacgt ccggcgtggg   33420
tggaagagct gcagcgtctc gcaccaggct gccggatcat gaaccactac ggcccgacgg   33480
agaccacggt cggcgtgttg acgtactgga ccggtgaccc cagggatctg ttcgtcgaga   33540
gcgtgccggc cggcaggccg ctcgggaacg tccgcgccta cgtgctcgat ccggccgag   33600
cgcccgcgcc gattggcgtc gtcggcgagc tctgtatcgg cggcgcgtgc gtggcacgcg   33660
ggtatctcaa tcgtcccgac ctcaccgccg agcgcttcgt ccccgatccg ttcgccaccg   33720
agccgggagc gcgcatgtac cggaccggcg accgcgcccg gttccggggcc gacgggaaca   33780
tcgagttcct cggtcgcgcg gactatcagg taaaagtacg cggattccgc gtcgagctcg   33840
gcgaaatcga agcggcgctt cgcgctcatg agggcgtcga gcaggccgta gtcgtgctgc   33900
gaaaagatca gcccggcgac gagcgcctga tcggctatgt cacgaccggc ggcggcgcct   33960
cgatctcgat ggcggagctt cgcacgtcgc tcaagcagag gttgccggac tacatggtgc   34020
```

```
cggcggtgat cgtcgcgctc gacaagctgc cggtcacgtc gattggcaag atcgatcgac    34080
gcgccctgcc ggcgccgccc gagcgcgcca gtttcgagtc ggagttcgtc acgcccgcca    34140
ccgagacgga gcgccggctt gcggagatct ggagcgcggt gctcggtctc gagaagattg    34200
gcgcgcacga caacttcttc gacctgggcg ggcactcgct gctcgcggcc cgcaccgcca    34260
tgaaggtccg cgacacgttt cgcgtggacg tgtcgctcat cacgttcttc gaaatgccca    34320
ccatcgccat gatggcggca gcaatcgacg ccggtaccgc ggccctgcc tcccggacca     34380
tcacgccgag ggcccgcgtc agggcccgca gggatgagct ggtccgccca tgaaccccgg    34440
ccaccccgca actgagtccc ccgacctgcg gcgcgacggg atcgccgccg aagcgggcga    34500
cgtgtttctg gcgccggcgt cgtacgccca ggggcgcttg tggttcctgg cgcagctcga    34560
gcctgaaagc tccgcctaca acattccgat cgcgctcaga ctgaagggcc gcctcgaccc    34620
cgccgcgctc gaacgcgcca tcaacaccat cgtccagcgt cacgagacgc tgcggacgac    34680
gttctcgctg cagggcgatg agctcaagca ggtcatctct ccgacgctgc gtattccgat    34740
ctccctcgtg gacatgcgtc tgctcagtcc tgagaaacgc gaggccggat ggcgccgcgt    34800
tgcgccgac gacggcgcgc gcgtcttcga tctggctgag ggcccgctgc tcaaggtcgt     34860
actcgtcatc ctcgagccct ccgatttcgt cctcctgatc accgtgcatc acatcgtctt    34920
cgacgggtgg tccggcggga tcttcatccg cgagctggcc gaggcgtacg cggctgagct    34980
cgacgggcgc gacccgaagc tgccggagct gccgatccag tacgcggact tgccgcgtt    35040
ccagaaggaa cagaccgaag ggccggcct gccggtgctg ttgaagcact ggacgcagga     35100
gctggcgggg gcgtcgatga cgctcgacct gccgacggat cgtccgcgtc cgcccctgca    35160
gacctcccgg ggcgccctcg cctcgcttcg gctcgacgga gcgatctggc cgggcgtcgc    35220
cgcattcagc cggggcgaga acgcgacggt gttcatgacg cttctctccg ccttcggcgc    35280
cgtgctgcat cgctggtccg gacaggaaga catcctcatc ggcagcccgt cggcggccg    35340
cgatcgtccg gagcttgagg gcctgatcgg gttcttcatc aacacgttcg tcctgcggct    35400
caacgcgtcg ggagatccca cgtttcgcga gttcgtcggc cgggcgcgcc gcgcgtgccg    35460
tgcggcctac gcgcatcagg acctgccgtt cgatcggctc gtcgagacgc tcaacccgga    35520
gcggacccgg gatcggcatc cgatctatca agtcatgttc gcgcaggatc cgccggcgtc    35580
gaaagatgacc ttcgccggga tcgagctcga gcggcttgtc gtccacaacc gcagcaccaa   35640
gtgcgacctc acgctcgagg ttgccgaaga cgccgacggc gtcaccctgt acgtcgagta    35700
cagcgtcgac ctgttcgatg cggcgacggt ggcgtcgctg ctgcagcaat atcgccgtgt    35760
gcttcagacc gcgatcgcgg acccggacca gcggctctcc gagctgcgtc tgcttggcga    35820
cgacgagcgc atgcagctga tcgcactggg gaccggtccg gcggccgtct acccgcgcga    35880
cgtcagtctg gccacggtct tcgaagagcg ggtccgcgcg actccggcgg cagtggccgc    35940
gacgctggag ggacagcacc tcacgtacgc ggatctcaac cggcaggcga accgcctggc    36000
ccggcggttg aaggcgttcg gtgtgggccc gaacgtgctg gtcggcgtgg cgctcgaccg    36060
gtcgttcgat ctgctggtgg cgctcctcgc cgtggcgaag gccggcggcg cgtatctccc    36120
gctcgatttc gctcacccgc aggaacggct tgcgttcatg ctcgccgaca cgcgcgcgcc    36180
catcgtgctc acgctgcggc gatttgccgg ggcgctcgag tcctttcccc tcttctgcct    36240
ggacgacgag ctgccggcca ccgccgagga gccggacgaa gatctgccgc gcagtcgac     36300
cggagaccac ctggcctatg tgatgtacac ctcgggctcg actggtcagc caagggcgt     36360
cgcgatcacg catcgcggcg tggttcgtct cgtacgcggc acagactacg tccgctggaa    36420
```

```
cgacgtgcgg gcgatcctcc acatcgcgcc gacgtcgttc gacgcgttga cgttcgaggt   36480
gtggggcgcg ttgctgaacg gcgcgcggct ggtgctggtt cccgagcggc tcgtcagcct   36540
ggagacgctc gagcgcacgc tccggtcgga gcaggtggac tgcctgctgc tcacgaccgc   36600
gctcttcaac gccgtcatcg acgcgaagcc cggcattctc gtcggcgtga agcaactcct   36660
gatcggcggc gaagcgctgt cagtcgcgca cgtgcggcgc gccctggcgc acctgccgga   36720
cacgcggctc gtgaacgcgt acggtccgac cgagtgcacg accatcgcgt gcgcctacca   36780
gattccgcgc acgctcgatc cgcaggcgcg gtccatttcg atcggccggc cgattgccaa   36840
tacgcaggcg ctcattctcg atcgacacgc cgacctcgtg ccgttcggca tcgccggcga   36900
gctctgcctc ggcggagacg ggctggcgcg ggaatacctg aatcagccgg cgctcactgc   36960
ggaacggttc gtgcccaacg cgttcagccc cgagccggcc gccggctgt accgcacggg   37020 agacctcgcg cggatgcgcc gcgacggcaa catcgagttc cttggccgga tggatcgcca   37080
gatcaaactg cgcggcttcc ggatcgagcc gggcgagatc gagcatgccc ttcgtgcccc   37140
gggagacgtt ctggacgcgg tggtggagat ccgggtcgat gcccacatgg cccatctcgt   37200
cgcctacgtc gtgcgcgccg atgggagtca actcaccgga accgacctgc gcgaacgtct   37260
gaaggcgcgc ctgccggaat actgtgtgcc cgcgaagtac gtgttcctgg ccgaggtccc   37320
gcgaacggcg gccggcaagg tcgatcgctc ggcgctgcct gcatcggcga tcgaggcgcc   37380
cgcgcccgag ccgcgcgatc cgtcgttcct gaacgaggtc gaagcggagc tcgcgcgaat   37440
ctggagcgaa gtgcttcggc tgccctccgt gctcgcgacc gacaattttt tcgatcgtgg   37500
```

<210> SEQ ID NO 2
<211> LENGTH: 37507
<212> TYPE: DNA
<213> ORGANISM: Artificial sequence
<220> FEATURE:
<223> OTHER INFORMATION: DNA sequence of clone FS3-135.

<400> SEQUENCE: 2

```
gatcccacga tcggcgccag cggattgcgc agctcgtgcg cgagcatcgc gaggaactcg     60
gtcacgtggc ggccctcggc ctccagctcc tccatgcgct tgcggtgcga gaggtcgcgc    120
gtcaccttgg cgaagcccat gtgccttcca ctcgcgtcgc gaagcgccgt cacgacgacg    180
tcggcccaga agcgcgtgcc gtccttgcgc acgcgccagc ccgtgtcctc ggcgcggcgg    240
tgcagcagcg catcgtgcag ctcggcctcc gggcggccgg ccgcggcatc ctcgggcgga    300
tagaagagcg aaaagtgccg tccgatgatc tcttcggcgc tgtagccggt gatgcgctcg    360
gcgcccttgt tccagctggt cacgtggccc gcggggtcca gcatgtagat cgcgtagtcc    420
tgcacgccct cgatcaggag gcgcgagcgc tcctcgcttt gccgcagctg ctcctcgtgc    480
tcgcggcgct cggtcaggtc gcgcgtgacc ttgccgaagc cgaccagcgt gccgtcctcg    540
tcgcgcagcg ccgtgatgat gacgttggcc cagaagcgcc ggccgtcctt gcgcacgcgc    600
cagccctcgt cctcgaagcg gccgtcctcg cgtgcgcgca gcagctcctt ggcgggccag    660
tcgcgcgcga tgtcctcctc ggtgtagaac gcggagaaat ggcggccgat gatctcttcg    720
gcgcgatagc ccttcaactg ttcggcgccc gcgttccacg aacgcacgta gccctcggga    780
tcgagcacga agatcgcgta gtccgtgacg gacccgacca gcagccggaa gatggcgtcc    840
tcgccggcca gcccgctcgg ggcgccgaag gcgaggttgc gcaccgaggg ccgcggaccg    900
gatgggcttg gcatggctat tagggtacaa cggtgcacgc aagttgcaat cggacaatca    960
gagataattg cttgatgaag atgccatttt tggaattctt acgcagggag ctggggacgc   1020
```

```
tcgaggccca gggcctgtac aagtccgagc gcgtgctcga ctctccgcag ggcgccagcg   1080
tgcaggtggc cgcccacgac gtgctcaact tctgcgccaa taactacctc ggcctggcca   1140
accacccggc cctggtcgcg gccgcgaagg agacgctcga gcgcgacggc tacggcatgg   1200
cgtcggttcg cttcatctgc gggacgcacg ccgtgcaccg cgagctggag acgcgcctcg   1260
cgcgcttcct cggcaccgag gacgcgatcc tgtacggctc ctgcttcgac gccaacggcg   1320
ggctcttcga gacgctgctg ggcgaggagg acgcggtgat ctcggacgcg ctgaaccacg   1380
cctcgatcat cgacggcgtg cgcctctcga aggcgaagcg cttccgctac gacaacaacg   1440
acatggcgag cctcgaggcc cagctgaagg cggcggacgc ggccggcgcg cgctacaaga   1500
tgatcgccac cgacggcgtg ttctcgatgg acggcatcgt cgcgaacctg gcgccatct   1560 gcgagctggc cgggcgctac cacgcgatgg tgatggtgga cgactcgcac gccgtgggct   1620
tcatgggcgc gcacgggcgg ggaacgcccg agcattgcgg tgtcgaaggg aaggtggaca   1680
tcctcaccgg cacgctcggc aaggcctgg gcggcgcttc cggcggctac acggcgggca   1740
agcgcgaggt ggtggcctgg cttcgcaacc gctcgcgccc ctatctcttc tccaacacgc   1800
tgatgcccgc catcgcgggc gcgtcgctca aggtgctcga tctcctcgag gcggcggcg   1860 agctgcgcgc gaagctcgcg cgcaacgccc gccacttccg cggcgagatg acgcgcctcg   1920
gcttcacgct ggccggcgcc gaccatccga tcatcccggt gatgctgggc gaggccccgc   1980
tcgcgaagga gatggcggac cggctgctga aggaaggcat ctacgtggtc ggcttctcgt   2040
ttcccgtggt gccccgaggg caggcgcgca tccgcacgca gatgtcggcc gcccatgaac   2100
cgaagcacgt cgatcgcgcc atcgccgcct ttgccaaagt cgggcgcgat ttgggagtca   2160
ttgcttgaga accctttcga agacgaagcg cgagcccggc atctggatgg tcgagtcgcc   2220
caagcccgtg gtcggccaca cgacgtgct gatccgcgtg aagaagaccg ccatctgcgg   2280
caccgacatg cacatcttca actgggacga ctggtcgcag aagaccatcc cggtgccgat   2340
gacggtcggc cacgagtacg taggcatggt ggaggccatg ggccaggagg tgcgcggcct   2400
gcaggtcggc cagcgcgtct ccggcgaggg ccacatcgtc tgcggccatt gccgcaactg   2460
ccgcgccggg cgccgccacc tgtgccgcaa cacgcagggc gtgggcgtga accgccccgg   2520
cgcgttcgcg gactacctgg tgattcccgc ggagaacgcg ttcccgattc ccgacgacat   2580
ccccgacgag atcgcctcga tcctcgatcc gttcggcaac gcggcgcaca ccgcgctctc   2640
gttcgacctg gtgggcgagg acgtgctgat caccggcgcc gggccgatcg gcatcatggc   2700
cgcggccatc gcgcgccacg tcggcgcgcg ccacgtcgtg atcacggaca tgaacgacta   2760
ccgcctggcg ctcgccacga agatgggtgc cagccgcgcg gtgaacgtat cgaaggaaaa   2820
cctgaaggac gtgatcgcgc agctcggcat ggtcgagggc ttcgacgtcg gcatggagat   2880
gtcgggcgtg ccctcggcct tccgccagat gctcgacacc atgaaccacg cggcaagat   2940 cgccatgctc ggcatcccgc ccagcgaggc cgcgatcgac tggacccagg tgatcttcaa   3000
gggcctggtc atcaagggcg tctacgggcg cgagatgttc gagacctggt acaagatgat   3060
cgccatgctg cagagtggcc tcgacctctc gcccatggtc acgcaccgct tcgacgtgcg   3120
cgagtacctg aagggcttcg agacgatggg ctccgggaaa tccggaaaag tcgtcctgtc   3180
gtgggattag cgagggccac ggatcgcggc ccggttcccg cggcggcgat cgtgcaggcg   3240
ggttggcagc acgccccggg atttccgccg tggctcacgt gcgacttcgc cgtcgacgca   3300
ccgatcgcga tcgacgtcga cgtgagcgtg tcgctgctcg atgcccaggg cacctcgctg   3360
tggacgcagt cgatggccgg cagcgggcgc gacaccccgt ggctaccgac cggcacgtat   3420
```

```
cgcgcctccc tgcgcctgga gccgttccgc ttcccggccg cggccgcctc ggtcgagttc    3480
gcgctctcga tgcgggtgca aggtgagcgc gcgtcgtgg ccaccgcagc gggcgtggtg     3540
cccgcgggcg caccccacgg cgtggcgcgc gcggcctggc acctcgaggc cctggatggc    3600
acgccggcgc tcgagacgct ggcctggtcc gatcccacgc acagctggtt ctcccagcat    3660
ttcgaccatg cgtcgcgcac gtgcgtcgag tacctgggcg ccggatggcc cgggtggcgc    3720
gggcgcgtgc tggatgcggg atgcggcgac ggcatcacgg cgctcggcat cgcgctgcgc    3780
tatgcgcccg agcaggtggt gggcatcgat ccggggcgct gctaccgggt gcttcccgac    3840
atcctcgagc gccacgccct cggccacctc gcgctgccgg acaacctgca gttcctcccc    3900
gcggatgcca acgcgctccc gttcgccgac agcagcttcg acgtcatcgt ctcgtggtcc    3960
gcggtcgagc atttcgtggg cggctacctg ccctcgctcg ccgaggcgcg gcgggtgctc    4020
aagcccggcg gcctgctggt catccatccc gagctctact acaccgcgca ccacggccat    4080
cacctcggcg agtacagccg cgagcccttc ttccacctgg tgaagtcgcc cgacgaggtg    4140
cgcgacatcg tgttcggcgc ggacgtgagc ctccacgacc gcggcggcat cgcgccgacg    4200
cgcgcggagc actggcgctg gtacaacgag ctcaatcgca tcacgcccgc gcagttcgag    4260
gacgagttgc gcgcgctcga cttcgagccg tggcgcctgg cactgcgcgc cgagccgctg    4320
gtggagtaca agccggagct gctgcgctac cgcttcacgg agctgggcgt ctccgagctc    4380
tacgtggcct gcatcaaccg caagcccgtg tcagatggtt cctacaggac gcatgggcag    4440
gcggcattcc ggtaaggtcc gccgggacgg gaattgaagg cgcaagcgcg ttgttatccc    4500
cgtcactccc ggactgccgg gatcaccctc acaggagaac ccccgatgaa gacccagacc    4560
caggccgtgc tcgccgcggc cctgctgtcc cttgccggca ccacgctggc ccgcgccgaa    4620
gccgtcacgc tgacgggcgc gagcgaagtc ccgcccgtca cctcgagcgc gaagggcagc    4680
ggcacggtgg tcgtgaaggc cgattgcacg gtcaccgcga agatcaccgt caccggcatg    4740
accgccaccg cggcccacat ccacgaaggc aaggccggcg caacgcgggc cgtggcagtc    4800
ccgttcgtga agaccgcgga cacacggttc gaggcagccc cgggcgccaa gatgaccgag    4860
gcgcagtgcg ccgcgtacaa ggcgggcggc acctacgtga acgtgcacag cgaggccac    4920 aagggcggcg aggtccgcgc ccagctggcc ggcaagtagg gcagccgctg caaaaagaaa    4980
aagcccgcgc aagcgggctt tttcgttgaa ggctttggtc ggggcgaaag gattcgaacc    5040
ttcgaccccc tgcaccccat gcaggtgcgc taccaggctg cgctacgccc gaccgaact    5100 tgaaattata cctgcatcgg ggtcgcagcc gccatgaatc gaaacgcccc gggcttcggg    5160
tagcatccgc ccatggcgac gaccctcgtg acgggtggtg caggctacat cggcacccac    5220
atcctctgcg cactggccca ggccgggcga cgcagcatct gcatcgacaa ctactccaac    5280
agctcgccgc gttccatcga acgcgtgctg cagatcgcac ccggttgcgt cgaggccttc    5340
gacgtggaca tccgcgacgc cgacggcatc cgcaaggtga tcgcagggcg cgacgtggac    5400
agcgtgatcc acctcgcggg actgaaggcg gtcggcgaat cggtcgagca gcccgagcgc    5460
taccacgaca acaacgtccg cggcaccgag agcctgctcg cggcgctcgc cgactcgccg    5520
gtgcgcaagt tcgtcttcag ctcctcggcc accgtgtacg gcctcgccga aaagatgccg    5580
atcgacgagg acgcgcccac ctcgccgcag agcccgtacg ccagaacaa gctcgacatc    5640 gagcacatgt ggtcgcccct cgccaagcgc gaccctcct ggcgcgtagt gaacctgcgc    5700
tacttcaacc cggtcggcgc acacgagagc gcgctgatcg gcgaggaccc ggccggggtt    5760
cccaacaacc tcatgcccta cgtgtgccag gtcgcctccg ggcgactgaa ggagctgagc    5820
```

```
gtctacggca gcgactaccc caccccggac ggcaccggca tgcgcgattt catccacgtc   5880
tgcgacctgg ccgaaggcca cgtggccgcg ctggaagcac tcgagcgcgc ggcccccggg   5940
accgtcctca cggtgaatct cgggacgggg ctcggctaca ccgtgctgca attgctcgaa   6000
accttcgagc gcgtgaacaa actaagcatt gcccggcgca tcgtggggcg gcggccgggc   6060
gacgtcgcga tctgctacgc gaacgcgggc cgcgcgaagg ccgtgctggg ttggaccgcg   6120
aagcgcggaa tcgaggagat gtgccgcgat gcctggcgtt ggcaggaaag gaatgcaaag   6180
ggctacggtt gacggattgc aaatcatggc cttggcgacc cttgctgcaa tgcggcatga   6240
agggggcggt tcttgtaaga tccaaggttc gggatgcgtc caggacgtca aaaacagcac   6300
ccggcgttgg aaggaagaag gcaaccctag tgttgtcatg gctccagacg ggattgcgcg   6360
ccgagtaaga atcgtcagtc gagaccaact cgcctccggg tgcaacgaat cgtgagccga   6420
agcaacacct cgcatcgcgt cgccgtcgtc ggcattgcgt tccgccttcc cggcgctacg   6480
cgcgaatccc tctggccctc gctcctcgag gggcgcaacc tcgtcaccac cgtcgatccc   6540
gcgcgctggg cgaaggagcc gtactaccac ccgcgcaagt ccgagcccgg caccagctac   6600
tcgttcgccg ccggcaccat cggcgacatc agccggcttcg acgcgtcgtt cttcggcatc   6660
tccccgcgcg aggccgcgca gatggatccg cagcagcgcc tgctgctcga gctctcctgg   6720
gaagccctcg aggccgcggc ggtgaagccc tcgaccctgc gcggcagcga ttgcggcgtg   6780
ttcgtgggcc tgtccaccgt cgactacagc tacggcctcg cctacgacct ggcgtccatg   6840
gacgcgtcgt cggccaccgg caacaccgcg agcatcgcgg ccaaccgcct ctcgtatttc   6900
tacgacctcc acggccccag catggtcgtg gatacggcgt gctcgtcctc gctggtggcg   6960
ttccaccagg cctgccagtc gatcgccatc ggcgagacgc gccaggcgct ggtgggcggc   7020
atcagcctgc acctgcatcc gtacgggttc atcgcgttct ccaaggcgtc gatgctctcg   7080
aagcgcggcg cctgccgcgt gttcgacgcc agcggcgatg gctacgtgcg ctcggaaggc   7140
gcgggcgtgc tggtgctgaa ggacctcgac cgcgccgtgg ccgacggcaa cccgatcctc   7200
gccgtcgtcg ccgcgagcgg cgtgaatacc gcgggccgct cctccagcct caccgtgccc   7260
agcgtcgatg cccaggctgc attgctgtcg gatgtgtacg agcgcgccgg catcgacccg   7320
tccgagatcg actacctcga ggcccacggc accggcaccg tggtgggcga tccgatcgag   7380
acccgcgccc tcggcatcgc gctcgggcgc ctgcgcccgc gccaccagcc gctgccgatc   7440
ggttcggtga agagcaacgt cggccacctc gaggcggcct cgggcatggc gggcctggtg   7500
aaggcgctgc attgcctcaa gcaccgcgcg gtgccgccca ccatccacct cgattcgccc   7560
aaccccaaca tccacttcga cgagtggaac ctgaagccgg tcctcgagcc gctcacgctc   7620
catccgtaca agaagctcgt cgtcggcgtg aactcgttcg gcttcggcgg cgccaacgcg   7680
cacgtgatcc tcgagagcac gcccacttcg cccaaggcgg tcgaggcccc ggccggcgag   7740
gtggcgctca tgctgagcgg ccacgacgac gcggcgctgc gcgacgtggc ggcctcgtac   7800
gcgaacttcc tgcaggcgag cgagcaaccc gcgctgcacg acatcgcgta caccaccgtg   7860
cactgccgcg actggcacca gctccgcgcc atggtggtcg gcaccgaccg cgccagcatc   7920
gccggcgccc tcgcgcaatt cgccaagggc cacaacacgc ccggcgtcgt gagcggccgt   7980
gcgctgccca acgcgtccgg ccccgcattc gtgtattcgg gcaacggcgc gcaatggccg   8040
gcaatggggc gcgccctgct cgccggcgag ccggtgttcc gtgccgccgt gcaatcggtc   8100
gacgcgctgt tccgccgct cggcggctac tccatcctcg agatgctgga gcaggaggtc   8160
cccgccgacc agctggaccg caccgagatc gcccagccgc tgctcttcgc cgtgcaggtg   8220
```

```
ggcttgaccg agctgctgcg ccactggggc atccagccca cgcgcgtcac cggccacagc   8280
gtgggcgagg tcgccgccgc ttgggcgagc ggcgcgctga cgctcgacga tgcggcgcgc   8340
gtgatctacc accgcagccg ctaccagggc gagaccaagg gcgcgggcgc gatgaccgcc   8400
gtcggcctcg ccgaggacgc cgcgcgccgc cagatcgagg cgctcgggtt gaagggcgag   8460
gtgaacgtcg cgtgcatcaa cagcacgcgc aacgtgacgc tcgccggcac gcgcgccggc   8520
atcgaggcgc tcgaggccga gctcacgcag cgcaaggtgt tccaccgccg cctcgacctc   8580
gactacgcgt tccacagccc ggcgatggac ccggtgcgcg acgggctcgt gagcgcgctg   8640
cgcggcctca cgccgcgcgc cacccgggtc gcgttccatt cggcggtcac cggctcgccc   8700
gccgcgggca accagctcga cgccacctac tggtggagca acatccgcga gccggtgcgc   8760
ttccaggccg cgatccgcgg catcgccgag tcgggcgtca atgtcttcat cgagatcggc   8820
ccgcacccga tcctcaagaa ctacatcaac gacggcctgc gcgccgcctc gatcgagggc   8880
cgcgcgctgg tcacgctgca gcgctcggcg agcgatcgcg cggcgatccg cgccgccgcc   8940
caggaagtcg tgatcaccgg ctgcccggtg gagaccgcga agatgctccc cgcgcagggc   9000
cacttcgtcg agctgccgcc ctacccgtgg cagcgcgagc gccactggcg cgcgcccacc   9060
tcgcaggcct acgacctcat ccagcacggc aagcagcacc cgctgctggg ctatcgcctg   9120
cacgagaacg acttccagtg ggaaaaccac atcgacaccg cgctctatcc ggcgtacgcg   9180
gaccatgtcg tcggcggcgc cgtggtgttc cccgcggccg gcttcgtcga gatggcgctc   9240
gccgcctcgg cgatcgcgct gggcggcgac gcgcacgaga tcgagacgct cgagatccgc   9300
agcgcgctgc tgctcgagga ctccacgtcg aagaccgtgc gcttcgcgct ggaacccgat   9360
ggccgcttca caatccgcag ccgcgctcgc ctgagcgagg atccgtggca actccacgtg   9420
gtcggcaagc tggtcggcac gcccaccgag cttccgcgcg cgccgcgcca gtcggcgccg   9480
tcgcgcaagc ccgatgtgat cgcggcccag cactacgaag gcgccgcgaa ggccggcctc   9540
gcctacggcc cggccttcca gtcggtctcc aaggtgtggc tcgacgccgc ggacccgggc   9600
agcgcctacg cgcgcctgat cctccccaag ccgattcgcg gcgagctggg cgtgatgcac   9660
ctgcaccccg cgtcgctgga cggctgcttc cagctgctgg tcgacctgct gcgcgccgag   9720
gcctcccggc acgcgcagat cgccttcgtg ccgatcctgg tcgggcgcac gcgcctctac   9780
ggccctgccg ccctcgtcac cgcctgccgc gtccgcctga ccgcgcgcag cccgcgctcg   9840
ctggtcgcgg acttcgagct ctacggcccc aacggcgacg tggtggccgc gctcaccggc   9900
gtgcgcttcc gcgcgtccta gctgaagcag ccgcagggcg cgcgcctgcg ctacctgtcg   9960
taccgcgcca tcccgcgcct gaatggcggc gacacgccgg gcgccaagcc gctgcccctc  10020
gcgttgctgg ccgcggcgtg cggcgagcgc tggcattcgc tctcggccgg ctcgcgcaag  10080
cgctactacg atgaggtcga gccgctctcc gacgtgctgt gcagctcctt cgccgagcac  10140
gcgctgcgaa agcggatcgg cgaggcccgc ctcatcgacc cggccgcgct cgccgcgtcg  10200
acgccggccg agcattggcc gctcctcaag cgcgcgatcg agatgctggt cgaggaccag  10260
ttgctcgagc ccgccgaagg cggctggcgc tggagcccgg tcaccgaatt gcccgacgcg  10320
caggagagct ggatcacgct gctgcgcgac tacccggacg aggccggcca gctgatcgcg  10380
ctcgggcgcg ccggcgctca cctcgcggaa gtgttcgccg gcaaggaagc gtccttgccg  10440
agcctgttgc cggccacgca ggcgaacgtg ttcgcgcgcc tgtgctcggg cgcacccgcg  10500
ttcgccaacg ccgggcgcgc catcgccgac acgctggcgc tcgccctcga gcgcctgccc  10560
gcgcaccggc cgctgcgcgt gctcgaggtg acgccgtgcc gctccgagat cacgctgcgc  10620
```

```
gtcctcgagg ccgtggacct cgaccgctgc gagtaccacg tcggctgcac cacggacgaa    10680
gcactgggcg agtacgaagg cgtcctcgat gccattccgc acgtcgagac ttgcgtcgtg    10740
gacctgaaga tcccgggcat gggcctgaag gcgccgaacc agggcccgtt cgatgtcgtg    10800
atcgtttccg atggcctgct cggtgcggcc gatccggatg cggccgcggc gcacctcgcc    10860
ggcgcgctcg cggaagacgg gctgctggtc atggtcgcgc agcatccgtc gcgctggacc    10920
gacctcctct tcggcgcgga cccggcgtgg tggacgctcg ggcctcgggc ctcgcagcgc    10980
tcgcgcctgc gttcgccgga cgagtggcgc atcgcgctgg cccacctcgg cttcgggccc    11040
accgtcgcgc tgcccgagct gcccggcctc gagcgcggct cgtacgtcct catggcgcgg    11100
cgcgacggcc cggtgccgca ggctgccgag cgcagcgttc ccgccaagtc gggctggatc    11160
ttcgtgcagg aagcgggcgg ttattcggcg gcgttcggcg cctgcgtgca ggcggatctg    11220
cgcgcacgcg gccacgcggt gttcgagatg gcgcccgatt ccgtcgaggg ggccgagatg    11280
gcgcagcttg cgcgcgcgcg ccagacgctg gcgacatca gcggcatcgc cttcctggcc    11340
ggcctgcccg acgacgcggc cgccacgggc gacgcggccg agcgcctcgc gcgccagacc    11400
gcgcgctgcg ccgcgctcgc gcgcctgctg cgcgaatgca aggcgagtgc catgacaccc    11460
gcggtgtgga tcgtgacctc gggcgcggcc tccagcctgg cgcgcaacgt ccccgcccttt   11520 gcctcgcgcc gccgccctcc cgatccggac gaggcgatcg tatggggggtt cgcgcgcacc    11580 gcgatgaacg aattccccga gctgcgcctg cgcctcgtgg actgcccgaa cccggagaac    11640
ctcgagcgca acgccgcctc gctggtgcag gagctgctct cgcccaccgc cgacgacgag    11700
gtggtcctca ccggcgccgg ccgctacgcg ctgcgcctgg gcgcggtgcc gccgcccgca    11760
tccgtgcgca ccgctaccca gggcatcacg cgcctcgact tcgccgcgcc cggcccgctg    11820
aagaacctcg cgtggcgcgg cgacgtgcgc cgcaagccgc gcgcgaacga ggtggaaatc    11880
gaggtgcgcg ccgcgggcct caacttccgc gacgtgatgt acgcgatggg cctgctctcc    11940
gacgaggcgg tcgagggcgg cttcgccggc gcctcgctcg gcatggagct ctcgggcgtc    12000
gtcaccgccg tcggcaagga cgtgacctcg gtcgcgcgcg cgacgaggt gctcgcgttc    12060 gcgccctcgg cgttcgccac gcacgtggtc accaccgccg attcggtcgc gaagaagccc    12120
gccggctgga cgttcgagtc cgcggccacc atcccgaccg cgttcttcac cgtgtactac    12180
tcgttgaagc acctgcccca gctgcgcgag ggcgagcgcg tcctgatcca cggcgccgcg    12240
ggcggcgtgg gcatcgccgc gatccaggtc gccaagtggc tgggcgcgga gatcttcgcc    12300
accgccggct ccgacgagaa gcgcgacttc gtgcgcctgc tgggcgcgga ccacgtgctc    12360
gactcgcgca cgctcacgtt cgccgacgac gtgctgcgca tcaccaacgg cgagggcgtc    12420
gacgtggtgc tgaactcgct ctccggcgag gccattgcgc gcaacctgcg cgcgctgcgc    12480
ccgttcggcc gcttcatcga gctcggcaag cgcgactact acgagaacac gcacatcggc    12540
ctgcgcccgt tccgcaacaa catctcgtac ttcggcgtcg atgccgacca gctcatgaag    12600
gagcggcccg acctcgcgcg ccagctcttc aacgagctga tgcagctctt cgagcagggc    12660
gtgctctcgc cgctgcccta ccgcgccttc gccgccaccg aggcggtgga agccttccgc    12720
tacatgcagc actcgcgcca gatcggcaag gtggtgctgt cgttcgccga cggcgtgaag    12780
gcgcagcccg cccggcccgc cgtgccgcgc gagctggcgc tgtcgccgaa cgccacgtac    12840
ctcgtcaccg gcggcctgtc gggcttcggc ctgcgcaccg cgcagtggct ggtggacaag    12900
ggtgcccgcc acctggtgct ggtctccaag agcggcgccc agtcgctcga gaccaaggcc    12960
gcggtggccg acctcgaggc ccagggcgcc acggtgatcg cggaggcgtg cgacatcacc    13020
```

-continued

```
gaccgcgcct ccgtgcaacg gctgctcgcc gaggtcgcgg ccgcgctgcc gccgctgcgc  13080
ggcgtgatcc acgcggcggc cgtgatccag gacggcttca tcaccaacat gacggccgcg  13140
cagatccgcg acgtgctggc gcccaaggtc ctcggcgccc gccacctgga cgagctcacg  13200
cgcggcgcca agctcgattt cttcgtgctg tactcgtcgg cgacgacgct gttcggcaac  13260
ccgggccagg ccaactacat cgcggccaac tgcttcctcg aggcactcgc caaggcgcgc  13320
cgcgtcgagg ccagccggc gctgtgcgtg ggctggggcg cgatcgggga cgtgggctac  13380
ctcgcgcgcc acgagaaggt gaaggaagcc ctgcagacgc acatgggcgg caccgcactc  13440
gagtcggagg ccgcgctcgc ggtgctggag cagctcctgc tcgccgacgc ctcgggcctc  13500
ggcgtgctcg acttcagctg gcgcaacctc cgccgcttcc tccccaccgc cgcctcgccg  13560
cgcttccgcg agctgggcgc gcgcggcgac gacgcgaagg acgacgacga ccggcgcggc  13620
gagctgcgcc gcctcgccaa cgagctggac gcctccgagc tctcggcgat gttcaccgac  13680
ctgctgcgcc gcgaggtggg cgagatcctg cgcatcccgc cggaccgcct cgatacgcgc  13740
cagcccttgc aggaaatggg catggattcg ctgatgggcg tggagctgct gaccgcggtg  13800
gaggcgcgct tcggcgtgaa cctgccggtg atgtcgctct ccgagcagcc gtcgatcgag  13860
aagctggtcg accgcatcgt gcgcgcgctg aaggacccga acgccggcac cgaggccgaa  13920
tcgcgcagcg accagatcga gcgcgtcgcc gcgcagtacg cgcccgagct cgactcgcgc  13980
caggtcgagg agctcacgca ggcggtcgat gacgcgcaag ccacgcagca gggacgtccg  14040
tgaaggcgcg caacctccgc ggcctctcgc aggcagtgaa ggagcagctg atccagcgcg  14100
tgctcgagca gcgcgtgcgc cgggtcgaga aggacaagcc ctcggcggtc gagtccgcca  14160
tcaacgcctt ccgccccgac cccgatgccc tgggccacat ctcggagcgc tactgccgct  14220
tcgacatgca cccggtctac cagcagatgc agctggtgaa ggaaggtgcc gcgaagctgg  14280
gcattcccga tccgtacttc cgcgcgcacg acggcgtggc cgcggatacc acgcgcattg  14340
ccgggcgcga gtacatcaac ttctccagct acaactacct cggcttctgc ggcgacccgg  14400
ccgtggatgc cgcggccaag caggccatcg acgaatacgg gaccctcggt ctcggccagc  14460
aggctcgtgt ccggcgagcg gccgctgcac cgcgagctgg agcgcgccat cgccgaggtc  14520
tatggcgtgc acgacgccgt ggccttcatc agcggccacg cgaccaacgt ctccaccatc  14580
ggccacctgt tcgggccgcg cgacctcatc gtgcacgacg cgttcgtgca caacagcatc  14640
ctgatgggca tccagctctc gggcgccaag cgcatggcct tcccgcacaa cgactggcgg  14700
gccctggacg agctgctgcg cgcgcagcgc cgccacttcg agcgcgtgct gatcgtgatc  14760
gagggcgtct acagcatgga cggggactac cccgagctgc ccgaattctc gcgcctgcgc  14820
cgccgccacc gcgcgttcct gatggtggat gaagcgcact ccttcggcgt gatgggcccg  14880
cgcggcttcg gcatccgcga ccacttcggc atggccggcg acgaggccga catctggatg  14940
ggcacgctct ccaagacgct cgcctcgtgc ggcggcttca tcgccggcga gaaggcgctg  15000
gtcgagcacc tgaagttcgc cgcccccggc ttcctctaca gcgtcggcat ggccccgccc  15060
gtggcggccg cggcgctcgc cgcgctgaac cgcatgcgcg aggagccggc gcgcgtggcc  15120
gccctgcagg cgcgcggacg cttcttcctc gaggccgcgc gcgccgcggg catcgacgtg  15180
ggcctctcgc agggcatggc cgtggtgccc gccatcaccg gcagctcgat ccgcgccggg  15240
cgcctggccg aggcgatgtt ccagcgcggc atcaacgtcc agccgatcgt ctacccggcc  15300
gtgcaggaga actcggcgcg cctgcgcttc ttcgtgagcg ccacgcacac cgaggagcag  15360
ctgcgcttca cggtccgcga gctcgccgac gcctggcgca agctctgagt ggcgggcccc  15420
```

```
cggctgcgcg tcgtcgtctg cacccacggc ggcctgaacg gcgcgctggt gctctcgcgg   15480
ctgctggccg cccccacgct cgaagtctcc gcgctggtga tctccagccg cgcgcgcggt   15540
gcccatgagt cgtatggccg tgccgcgctc ggatacgtgc gcgcgagcgg cgtcgcctat   15600
gcgctgtacc tctggtgcgc cacggcgctc gccgacctgc tgctgcgcgg cacgtccgag   15660
ggcccggtcg cgcgcatcgc cctcgcgcgc ggcatcccgc tcctcgccac gccgcgcgtg   15720
aacgatgcca ccgcgcgcgc cttcatcgcg ggggcggcgc cggacctgat cgtctccgcg   15780
ttcttcaacc agcacatcga cgccgacgtg gctgcgctcg cgcgcgtggc cgcggtcaac   15840
atccacccgt cgccgctgcc gcacttccgc ggcgtggatc cggtgtcctt cgcgcgcctg   15900
cgcggtgccg agcgccacgg cgtgagcgtg catcgcatcg aacccggctt cgataccggc   15960
gcgctgctcg cccaggaaac cgacgtcgag gcccccggca gcgtctttgc cgccaccgcg   16020
gcgctctatg accgcggggc ggcgctcctc gccggccgtg ccgcggcgct ggccgccgac   16080
ccgcgcggaa cccccagcc ggcgggggc tcctacgact cctggcccac ccgcgcccag   16140
gtcgccgcct tccggcgcgc cggcgggcgc ctgctccgcg cccgcgacct gtggcgcctc   16200
gcgcgccggg ggcggccgc tttcgtaata gaatcagcgc ggtagcggcg actcacgccg   16260
cgcttttccc cgaccccccg aggcccatga aacactggct gaagcaacac gcaatcttcg   16320
cgctcaccgt cctgctgccg accgtggccg cgatcctcta cttcggcctg atcgcctccg   16380
acgtctacat ctccgaatca cgcttcgtgg tgaggagccc ccagcgccag gtgcagaccg   16440
gcctggtggg cgccctgctc tcgggcaccg gcttctcgcg ctcccaggac gacacctact   16500
cggtgcacga cttcatcacc tcgcgcgacg cgctgggcga gctggacaag aagctcgccg   16560
tccgcaagct ctacacggcc gccaacatcg acttcatcaa ccgcttcccg gggctcgact   16620
gggacgacag cttcgaggcg ttccaccgct actaccagaa gaaggtcacg atcgacttcg   16680
acaccgcgtc ctcgatcacg gtgctgcgcg tgcgcgcctt cgagaaggcc gactcgcggc   16740
gcatcaacga cctgctgctg cagatgggcg agcgcctggt gaacgagctg aacgagcgca   16800
gccgccagga cctgatccgc ttcgcgcagg ccgaggtctc gctcgccgag gacaaggtga   16860
aggatgccgc gctggcgctc tccgccttcc gcagcaacca gtcggtgttc gagcccgacc   16920
gccaggcctc gatccagctg cagggcgtgg ccaagctcca ggaggagctc atcgccaccg   16980
aggggcagct ggcacagctg cgcaagctct cgcccgacaa cccgcagatc ggcgcgctcg   17040
agaacaagtc ggcggcgctg cgcgtggcga tggcgcgcga gtccgccaag gtgaccggcg   17100
gcagcggctc gttcagcgcg cgcgccccgg cgttcgagcg cctcaccctc gagaagggct   17160
tcgccgaccg ccagctgggc gttgccctca ccgcgctgga gaccgcgcgc agcgaggcgc   17220
agaggaagca gctctacctc gagcgcatcg tgcagcccaa cctgcccgac gaatcggtcg   17280
agccgcgccg catccgctcg atcttcaccg tgttcgtgct gggcctggtg gcctggggcg   17340
tggtgagcct gctggtggcg agcgtgcgcg agcacgtcga ctaggccgtg gagcagaacc   17400
cttccctcct gcgcgccctc ggggtgcagc ggcgcgtgct ctacgcgctg ctgatgcgcg   17460
aggtcatcac gcgcttcggg cgcgacgacc tcggcgtgct gtggctggtg gtcgagccga   17520
tgatcttcac gctcggcgtg acggcccgt ggaccgcggc cggcatgaac cacgctcgt   17580 cgctgccgat cgtggccttc gcggtcaccg gatactccgc ggtgctggta tggcgcaact   17640
gcgcctcgcg cgcctcgatg gccatcgagg ccaacaaggg cctgctcttc caccgcaacg   17700
tgcgcgtgat cgacgtgttc gtgacgcgca tcatcctcga gatcgcgggc gccacggcgt   17760
cgttcaccgt gctgggcatc ttcttcatct ggatcggctg gatgccgatg ccgatcgaca   17820
```

```
tgctcaaggt cgcgttcggc tggttcatgc tgtcgtggtt cggcgccagc ctggcgctcg   17880
ccatcggcgc cggcaccgcg tactcgctgg tggtcgagcg gctgtggccg ccgacggcct   17940
acctgctgtt cccgctctcg ggcgccgcct tcatggtcga gtggctgccg gagaaattcc   18000
agcagttcgt gctcttgctg ccgatggtgc acggcaccga gctgctgcgc gacggctact   18060
tcggcaacgc ggtgcgcacg cactacgacg tgggctacat ggcaacggtc tcgctgggcc   18120
tgtcgctgct cggcatgcac ctggtgcgca tggcggccaa gcgcgtggag gccgcgtgat   18180
ccgggtcgag aacgtgacca gatgtactca cgcgcctcgg cccagaacgt gctgacgcgt   18240
cagcttcgag ctcggccgcg ggcgcaacat cggcatcctc ggcaagaacg cgcgcggcaa   18300
gtccacgctg atccgcctga tcagcggcgc cgagagcccc accaccgggc gcatcgtgcg   18360
cgagatgagc gtgtcctggc cgctcgcctt cggcggcgcg ttccagaccc acctcaccgg   18420
gctggacaac ctgaagttcg tctgccgcat ctacggcgtc gactaccgcg acaaggtcgc   18480
cttcgtcgag gacttcaccg agctcggcgt gtatttccgc gagccggtgt tccactactc   18540
gcacggcatg atcacgcgcc tcgccttcgc gctgtcgatg gcggtggagt tcgactgctt   18600
cctgatcgac gaggcgatgg tggtgggcga cgcgcgcttc cacgagcgct gccacgtcga   18660
gctcttccac aagcgcaagg accgcgcctt catcctcgtc acccacgacg ccaaggtgat   18720
caagctctat tgcgagagcg cctgcgtgct gcacgagggg cggctgctgc ccttccccac   18780
cgtggacgcc gcctacgagt tctacatgaa cgaggtcatg caggacctcg ccccggaggt   18840
tgcctgaacg ccccgcgcg gccgctgcgc gtgctcctcg agctgcggcc ggcgttcgac   18900
ggccacgccg gcatcccgca ggaggcacgc ctgctgttcc gcggcctgcg catgatcgag   18960
ggcatcgacg tggagggcct gctgcagcac agcggccacg tgctcgccaa gggcctgccg   19020
ccgcgcggcg gcggcgacct cgcaccggac cgccagctga accgcctgtc gcgcgtcgtg   19080
gtctccacca gcaggagct caccaacgcg cacgtggcga cggcgctgat ggccattcgc   19140
cagctgctgg gcgcgcgcga gaccctctac cgcttcgacg cggcgcactt ccgcgacttc   19200
gtctggcagg cgctcttcgc gcgcacgctg cacgccgcgg acttcgactc ggtcaccgc   19260 gccggctttc gcgtcgcgcg cgtgccgtgg acgggcatgc accgctgcgc gctggtcacg   19320
cgcaagctcg gctacacgct gcatccgcgc atcgacactt ccgatttcga cgtgctgatc   19380
gccgagacgc cctacccggc gcgggtcgcg gacggcacgc gcctcgtggt gcgctaccac   19440
gacgcgatcc cgctcctcat gccgcacacc atctccgaca tgtcctacca ccaggcctcg   19500
cactaccggg cgctgcgccg caacgtggcc tcgggcgcgc acttcgcgtg cgtctccgaa   19560
gccacgcgca aggacctgct ctcggtctttt cccgaggtcg aggcgcgctc cagcaccatc   19620
cacaacatgt tctcgcacca ctacttccgc gagaccgccg acgccgggcg catcgaggag   19680
atcctgcgaa cgcgcgcgag cgagcgcatc aagggcgcgc caacggagc cgccaccgcc   19740 gtcgcacgat cgccctcctt cctcgcgcgc gccgcgcaac ccagcgaccc cggctacctg   19800
ctcgccgtgg cgacgatcga gccgcgcaag aaccacgcgg gactgatcgc cgcgtgggag   19860
cacctgcgca cctcgcgctt cccgggcctg cgcctggtgg tggtcggcat gcccggctgg   19920
ggctacgagg cgctggtagc caagttcaag ccgtggctcg cgcgcggcca gctcttcgtg   19980
ctcgaggacg tgcccgcccc cgagctgcgc ctgctctact cgcacgcgcg tgccacggtg   20040
tgcccgagct tcggcgaggg cttcgatttc tccggcgtgg aggcgatgcg ctgcggcagc   20100
ccggtgatcg cctcggagat cgccgcgcac cgcgaggtgt accgcgacgc cgccgagtac   20160
tgcagcccct attccgtggc cgacctcgcc gaggcgatcg ggcgcgtcat cgacccggcg   20220
```

```
gcgacgggcc tgcgccaggc gctggtcacg cgcggcaccg aggtctcgca gcggtacacg    20280
cccgaagcca tcctgccgca gtggcgcgag tacctgctcg gcacggtgcg cgcggaggcc    20340
ccgtgagcga tccgaaggcc accgaccagg cgtgggagga gtggggccag cgcgacccct    20400
acttcggcgt gatcaccaac ccgcgcttcc gccgcgggca gatggacgag gaagcgaagc    20460
gcgaattcct cgcgtccggc cgcgtccatg ccgactacgt gatgcgcatg gtgcacgcgc    20520
acatcgcgcc cgacttccgt ccgcgcacca tcctcgattt cggctgcggc gtgggccgcc    20580
tcgtcatccc cttcgccgcc caggccgagc aggtgaccgg cgccgacgtc tcccccctcga   20640 tgctggccga ggctgcgcgc aactgcgccg agcagggcgt ggccaatgcg cgcctcgtgg    20700
tctcggacga ctcgctcacc gggctgccgg gccccttcga cctcgtgcac tcgttcatcg    20760
tgttccagca catcgatccg gcgcgcgggc gcgacatctt ccgccgcctg ctgggcaccc    20820
tggcgagcgg cggcgtgggc gcgttgcact tcgtctatgc gaagcgtatc tacgcggcga    20880 cgtacgcgt ggcgccaccg cccgagccgc cgccgccccc gccgccgccg cagcctccac    20940
ccagccgggc ggagatcaag gccgcgagca aggcgcgggc cgcgctggcc acgcaggcac    21000
gggcgccgga accggcaccc aatcccgacc ccgacatgca gatgaattcc tacccggcgg    21060
cggagatgct gttcctcgtg caggaagccg gcgtcacgcg cttccacgtc gagttcaccg    21120
accacggcgg cgagctgggt ctcttcctct tcttccgcaa gccctaggcg tccttcgagg    21180
cgaaggagag gccagcgcg gtgatcgtcg cggcgtgctg cggggcgacc gccgccgcgg    21240
ccgcgacttc ggcagccacg cgctcgaggt cgccgcgcga cccgtacagg cgcacgcgcc    21300
agtagtgcac ccagtaggag tccggacagg ccgacgcgat tccagcgcg cgctcgacct    21360 cgggcccgac gcgcccctgg tgcacttggt gcgaggccca ttgcaggttc acggagggct    21420
cgaggggcag gacggcgagc agcgcctcgc tcaccgccag cgcgcgcgcc tcatcgccgt    21480
cgtcggcgag gcgcatcagc gtgggcaggg actccggcgc aagcgcgtgc gcggccgcga    21540
gcgaatcgcg cagcatcgca gcgtcgccgc gcgcgagcgc caggcgggcg cggtggtagt    21600
gggtccagaa cgaaggcgcc gcggcatcga gcgcgcgcgc gacctcggcg cttgcgtcgc    21660
ccccggagag ccgggacgcg gcccacaaca ggttcgcctc cgccgcgtgc gccggcacgc    21720
tccgcaacgg cgccagcacc gcggtggcga cctcgcgcga accctcgcgc gacgagaagg    21780
ccgagcgcgc gaactgcatc agcgattcgc cgagcgacga atgttcggcg cagagccgcg    21840
cgggatccac cgcgccgagc gcgcgggcgg cacgcagcgc cgcctcctcg tcaccgcgaa    21900
gcgcgtgcag ccgcaggcga tggaacgcgg cccactccgc cgacatcgac gccgccccgc    21960
gctccagcgc accctcgacg gcgccatcgg tgcgcccgcg cgcgatgtgc aggatggccc    22020
aggtcgcctg cgccgcgggg aggttcgtgc cttgcgcgac gagcgggtcg aggaccgcga    22080
gcgccgcggc ggcgtcgcgc gcgccactga agtcgttggc caggccgatc agcgccccgg    22140
cgagctcggg ggccgcgcgg aaggcggccg ccgcgtcgcg ccccaccgcc gcgaggtcgc    22200
cgcgcagccg gtagaggcgc gcgcggtggt aatagcccca gaacgggtcg gggctcgcga    22260
tcagtgaatc gaacgagcgc tcgacctcgc cgcccacgtt gccgaggtcc acctggtgcg    22320
cgccccacag ggtcgccgca tgcgcggcca tcggctcgtc ggggacgaag gcgcggtgga    22380
tcagctcgac gtcgccgaag cgccgctcgc gcaacgcgag ctccagggcg ttcagccgct    22440
cgaggctcgc cttgtactcg cgataggcat cgcggtcgcg gtcgtattcc tgcgcggcac    22500
tgtcgtccat cagcgaggcc gtgagccgct ggtcgccgtg aacggtgtcg tatgcgtagg    22560
ccgcgcgatc gtcgtagggc agcgtggccg cgcgcagcga cccgaacgcg gcgcggtcgc    22620
```

```
ggaatcccag cttgcccagc acgcggggtg ccaggtcgtg ggcttccatc tcgcccgggc   22680
tccagtcgcg cagcgccggc acgttcgagt agagccacaa cggcgtgcgg tagagctgcg   22740
ccaggtccgc gtccgggcgg ccctgcgcct cgaagatcgc cttccactcc gcgagtccct   22800 cgtggccgg ggagaagatc ggcacgtggt cgccgaagat cgccagcacg tagggccgcc   22860
cgcgcacctc gagacgctcg accagcgagc gcagcgcgcg gtcggtttcg gccatcaccg   22920
cgcagtactt gtcgatcgcg ccctggcgca cgtgcccggc gaggaagtgc ggcgccacgt   22980
agcgcggctc ggcgcccttg tcgcccaggt agggtccgtg gcccatcagc gagacgccga   23040
acacgaagcg cggccgcgaa tcgtcgagct ccgcgatcac ggcatccatc acggccgaat   23100
ccgcgatgcg ctcgaactgg cgcggcgcat gggcgaacgc ctcgtcggcg tggaacgccg   23160
cgaagccgag cttcttgtac acgcggtcgc ggttgtagaa ccagcggtgg aacggatgga   23220
tggccacgct gcggtagccg tggcggcgca gcatgcgcgg caccgcatac acccggtcgc   23280
gcaactgccc catgtagggc agcgcgcggc agccttcctc gcccaatgcg atgccggtga   23340
ggatctcgaa ctcggtgtcg caggtgttgc cgccgatcac cttcacgcgc aggcggccgg   23400
tggtgcggcc cggccgcgtc gcgccgagga acggcagcgg gtcgcgcgcg agcggcacgc   23460
cgaacgggcg caggtcggcg agcgactcca tcatcaggaa gatgatgtcg gggcgctccg   23520
cggtggccgg gccgctcgcc gagcgctcct ggcgctccag cagccgctcc acgccctcgc   23580
gcagccgccg cggcgcgacc gggcgggcga tgctcccggc gaccagcacg gcgtgcagga   23640
cgaagcccag gcgccgcacg ttcacgttgt ggtcggtggg cgaatacgtc atcgcgtcga   23700
actccaccgg ccagcggcgc aagcgtccgg cgacgaaggc gacgccgagc gcggcgagca   23760
cgagcagcca ctgccggcga tcgtcgtacg cgtcgtgcag gtcgatggcc tcggtgatct   23820
cgaacgcggc ccacgccagc gccgcgagca ctgcggcagc ggcaagcgcg cgcaccgcca   23880
cgcgcgggcc atgcaggtac gccggcgcga acaccagcgc ctcgcgagcg ctcaggaaat   23940
cgcccgggcc gaccacgcgg ccgaagaacg cgagcaggcc tgcgttcacc gcgtagagcg   24000
cgcccgccag cgccacggtc cccaccgtcg cgagcgcccc gaccgcgacg aagagcagcg   24060
catggaagat ggcgagcagg ccggcgttcc aggccaggcg ccgcgcgcgc gccacgggtt   24120
ccacgtcata gcccaccacg aggcgccgct cgagggcggc ctgcagcacc gcgtaggcga   24180
gcacgcagac cagcgtgccg cccagcagca cgccgaggaa acccgccaaa ccagccgtgt   24240
cgtcgaggat catgggacca ccagggacgt cttccggcca gtctataacg ccccgcccca   24300
tgaaaaacgg cgaggcccgg gggcctcgcc gtggagggaa ccgcgcaacc tcagggttgc   24360
gggggtgcga ccgaccagcc gccggggccg atcaggtttg cgctgccgat ggtggcgagc   24420
ccgttcatca ggcgcaccgt gacgctgccg tcggtgtggc ggaagaccag gtccttgcgg   24480
ctgtcgccgt tcaggtccag cagctgcgtc acgttccaac ccgtgcccgc cggcagcgca   24540
tcgcccgcgg tgatgatgga aacaccatcc atcaggcgga tgtgcacgcg gccgtcggtg   24600
tggcggaaga ccaggtcgtc cttcgcgtcg ccgttcaggt cgcccaccag gttcaccgac   24660
cacccgctgc cggccggcag gagctgggcg ctggcgccga aggtggtgcc gttcatcagg   24720
aacaggtgcg cgcggccgtc ggtgtggcgg aagatcatgt ccgcgcgtcc gtcgccgttg   24780
aggtcgccca ggtggcttac cgtccagccg ctggcggccg agaggaagcc cgctccggcc   24840
gtcaccgtgg tgccgtccat gatgtagatg tagccgcggc cgtcgctgtg catgaagacc   24900
aggtccgcct tgccgtcgcc gttcatgtcg cccgcctggg tgagcgtcca gccggtcccc   24960
gccccgaaga gctgggcgct gccgatgatc gtcgtgccgt ccatcaacca gatgtgcgcg   25020
```

```
cgtccgtcgg tgtggcgcag gatgatgtcc gccttgccgt cgccgttcag gtccgccgtg    25080
tggctcacga tccagccgag cccggcgggc agcagctcct tgccggccgt caccgtagtc    25140
ccgttcatga tgtacgcgta ggcgcggcca tcggtgtggc ggaacaggat gtcggcgcgc    25200
aggtcgccat tgaggtcggc cgtctggctc accgtccagc ccgcgccggc gccgatcagg    25260
ttggccgagc cggtgatggc ggtgccgttc atcgtccaca ccgcgatgcg cccgtcgctg    25320
ttctgcagca cgaggtcgct cctgccgtcg ccgctcaggt ccgagacgac cggcttggtg    25380
ggcggcgtga cgccaccgga aaccggcagt gccagcccgt cgatccaggc gcggtcggcg    25440
cagttggcgc catccggggc cggcgggttc caggtcggcg agttgcaagg cgtggagagg    25500
aagttcgaga aacgccacac cagcgtgtgc gcgcccgcgg tcaccgggaa cgacaccagc    25560
ttccagcccg aggccgtggt gcccgcgtcg ctgaacacca ccgtgccgtc gatcaggaac    25620
tcgaacttgc cggcgttggg gaagctcgac acgcgatagg cgaacgcgac gttgcccgcg    25680
agcagcgtgc ccgcgaacga gaggtcggag ttcaccgtcg tcgagttggt cgggtcgctc    25740
gtcaccacct gcgccgaacg aaggctggtc gcgccctcga aggcctggtc ggagccgacc    25800
gtccatgcgt tggcgccgcc cgaggtcgtg aagccggcag gcagcgtgcc acccgtgggc    25860
cacggcgaga ggatgatgcc ggtcgcggtc gccgggccgc cgatgaagac acccgtggaa    25920
cccgtcgcat tggagagcgc gacgttgaac gtctcgttgc cttcaccgat accgtcgctc    25980
gccaccggga ccgtgatggt cttgggcgtg gtctcgccgt tgcccagct gagcgagccc    26040 gaggtcgcgg tgtagtcggc gcccgaagtg cggtgccgt tggaggtggc gtagctgacc    26100
gagatggcac ccgccgagcc gccgatgcgg ctcacggtga gcgtcacgtt gccggcggtt    26160
tccgcggccg cgaaggtggt gccggtgaac tgcaccgaac cgggaacggc gggcggggtg    26220
accgtggact tgagcgccga gagtgccgcg cggttgttgt tcagcgagag cgcgtcgttg    26280
gcctgcgcgg tgccgcacgg ttgcggcgca ccgacacccg tcgtgcacga gaggcccggg    26340
ttggagaagc ggtagacctt ggtcgtcgag tcatgcagca cgacatgat ggtggtgaag    26400 ttcgccgcgt cgttcgtcgt gcactcgggg cgctggctca cgccgcaggc gccgccgccg    26460
gagccgttgg gcagggccga gttgcaggtg aggttgccgc tcgcgcaata gaagtggccg    26520
tacgagtacg cgaacgcacc ttgcggcggg ctcgcggtgc cgcccgcttc ccaggcctgc    26580
gaggggcggt cgtggcggtt gcccatggca tggccgagct cgtggatgaa gacccactcg    26640
caaccgaaca ggcagccgga agcaacggcg taggcaaagt tggggtccgg cgtgctggtg    26700
ccgatccagg ctgcgccgtt gccgccgaag tcggcgccgt tgcgcatgaa ggccaccatg    26760
tccgcgccgt attgcgtgcg gatggcctcg atgttgccga acgtcgcggc gtcgaagctc    26820
gcgtcgcccg gggtgatggc atgcatcgcc gtggtgtcgt cgatggcgtc gtcgtagttc    26880
acctgcgtcg cattcaccag gcgcagcgtg atggcgacct cgctgtcggc atacgcagtg    26940
ttggcgcgcg tgacgaggaa gttcaggcgc gtcatcaggc tgccgccgag gcgctggccg    27000
aagccgcgcg agtacacgat catcaggtcg atgacgttct gcggcgtggg cgtcacctgg    27060
gcgagccgac ggtattcacg ccggggatgg cgatcagggt ctcggggctg ccggtcgcga    27120
cgacgcgcga cttcgagccg gtcgtggcca cggcgtggtc ggcgccgagg ctgatgatcg    27180
gcatgctggc ctgctcggcc gtcatgtcga ccaggtagtc gacggtgccg cccggaatca    27240
ggcggtactc accctgcggg gtcgagaaca cgccgaagga gccttcaggc ccggtcgtga    27300
cgatcgcgcg gtggttgatg ccgtcggtct tgctcttcgc gatccacgac gtgatgccgt    27360
cgccgtgggc ctggagcaac tcgaagacat acgagtggcg caccccgttg gggagcgaca    27420
```

```
gctcgacctc ggagcgcgga ctcagggcat ggagggccgc ggcgttgaag cgcaccgctt   27480
gccgggcaac ggcgctgccc ggcgccggca tcgcggcggc gggtgcggag accaggatct   27540
ggggaaccgc ggcgaaggcc acggaagaga agacgatcgc cagcgcgccg aggaaggcgg   27600
ctgtgatccg ttgcgtgaat gcgttcatgt ggagctccgg aagttgaccc atgcccaatc   27660
cgctatgtcg cggagatgtg gacaaaaggt atcgagcggg cgtgacgacc cgcccccgga   27720
gggatgctcc aaaaggacta cgagggtgct acggctgggt tggtggcgaa ggccgaagga   27780
gaactccttg tggtctccgc gcgacttaag gttgcgaggg aaccaccgac cacccaccgg   27840
ggccgatcaa gtccgcgctg ccgatcgtgg tgacgccgtt catcaggcga atcgtcacgc   27900
gcccatcgtt gtggtggaag accacgtcca tgcgcccgtc gccgttgaag tcgaggagct   27960
gcgtcaccgt ccagcccgcg aacggcggca ggatgtcggc ggcgccgagg atcgcggtgc   28020
cgttcatcag gcgcacgtgc gcgcggccgt cggtgtgcgc gaacacgagg tccgcccggc   28080
cgtcgccgtt gagatctccc accaggttca ccgaccatcc ggtgcccgcg ggcaacagct   28140
cggcgctggc gccgaacgtc gtgccatcca tcaggaacag gtgtgcgcgg ccgtcgttgt   28200
ggcggaagac gaggtcggcc ttctggtcgc cgctgaagtc cgcgacgtgg ctcaccgccc   28260
agccgctgcc gggcgcgagg aagcccacgc cggcggtgat cgccgtgccg ttcatgatgt   28320
atgcgtagcc gcgcccatcg acgttggaga agacgatgtc ggccttgccg tcgccgttca   28380
tgtcgccggt gccgaccacg ttccatcccg agcccgcggg cagcaggctc gcactgccgc   28440
tgatcgcggt gccattcatc agccagatgt gggcgcgtcc gtccgtgtgc tgagcagcag   28500
gtcggccttg ccgtcgccgt tcaggtccgc cgtgtggctg atggtccagc ccgtgccggc   28560
ggggaacagc tccttgccgc ccacgaccgt gagcccgttc atctggtacg tgtagatgcg   28620
cccgtcggtg tgctggaagt agatgtcggc ctggctgtcg ccgttggaat ccgcggccat   28680
tgatcacgct ccagccggcg ccggcgggaa tcaggttcgc cgaaccagtg atcgtcgttc   28740
cgttcatggt ccacgcggcg atgcgcccat cggtgtgctg gaacaggaag tcgctctgcc   28800
cgtcgccgtt caggtcggtc gccgcatggg tcgggaacgc caccttcgcg aggaaggcat   28860
cggagaaacc cgtgagcaac gtcttgtacg cgccgggcgt ggtcggatag ttcgccgacg   28920
acgtgcggcc ggccacatag gccgcgcccc gcgcatcgac gccgacgccg taccccacct   28980
cgacgttgtt gccgccgatc agcgtcgaga acacgatgtc gccgttgcgc acgcgagtga   29040
ggaacgcgtc ggcatcgccg ccggggccct gcaccgggtt cagggtcggg aagccggcga   29100
cctgcgtgta gcccacgacg agcgcatcgc cattcggcgc cagggcgacg tccagggat   29160 tgtcgtaggc cgagccgccg aagatgcccg acgattcgag cgcgccggtg ccgagaagc   29220 gcgtcacgaa cgcatcgacg gtgccggcga aattgcgcac cgttccggtc tgcgggaagc   29280
tgggcaggcc ggtatcgccg acgacggtcg cctggcccgt gaccgggttc accgcgatcg   29340
cggtcacgtt gtcgccgctg ccgccgagga acgtggaata cgcgaccggg ccgccgctcg   29400
caccgatctt ggtgacgaag ccgccaccgg gttgggtctg gtacgcattc acgttgcgga   29460
acgtcgagga gcgcgtggag cccgcgacgt acgtgttgcc cgcattgtcc gttgcgatac   29520
cgcggccgat gtcatcaccg ctgccgccga gatacgtgga atagacgaag ccgccgttga   29580
acgagagctg gtgacgaacg cgtcgcgatt gaggccggtg ccgacgaaca cggctgcagc   29640 ggcgctgccgc cggtcgggaa gccgcgcgcg gccgaacccg tgacatgcat gaagccgttg   29700
ttgtccacgg cgatcgccat gccctcgtcg tcgccggagc cgcccagcag ccgcgagaag   29760
atgacgttgc cagtggtatt cagcgccgtg acgaatgcat cgcgcccgcc ggcatggttg   29820
```

```
gtgcaatcgg tgacggcgaa gcaatgcggg aacgcgttgg tgccggtgga accggtgatc    29880
gcgacgaact cgttgccgcc ggaggcgccg agcgccagcc cgcggagata cgcttcggcc    29940
ccgagcgtgg tcgagtacac cacctgctgc gtggtggggt tgaacttcac caccgtggct    30000
tcgtacgtgc ctgcggtata ggtcgcgagc ccgacgtaca cgttgccctg cgcgtccacc    30060
ttgaccggcg tggtccactg ctcgtcgccg gcgccgccca ggtacgtgga aacgccatc     30120 accgggtcga tcaccagcgt gcgggtgctg tcgtagtcgg cgatcacgaa gccggcctcg    30180
gcgccctgct cgcccacgaa gagctcgaag cgcgcggcca ccggcacgcg cgaatcgccg    30240
acctgctgga aggctaccgg cgcgtgctgc gtaaattcct cctggcccac gcgcatgcgc    30300
aggttgccct cgccatcgat ccacgcgtgg tcggcggacg agaggtcgag gcggatctgg    30360
cgcggatcgg cgcgcgggc gaccacgaag tcgtattcga gcgtgccctc cttgccgtac     30420
acggtgaggt ccacgccgcg atacaggtcc ttcagcgaca cgcggccgaa gtgcggcacg    30480
ttttcgcgcc ggccggcggc cgtggtgccg ctgtaatagt ggctgagggt ggcccggggc    30540
tcctcggcct cgatgaccgg atcggaagcc cccgcgaagc gcacgcgcaa cagcgaggcg    30600
ctggcagctt cctggagcg tggctcgaag gcaatgccat cgcggctcac ggagacgcgt     30660
ccggcctgcc cgcgcgagac gtagagcgca tccgggccga actggccctc gttgcgctcg    30720
aacgtgatgg gcgcgttcct gagggcatca gggacgacgg catggacggc ggcgggagtg    30780
gcgagggcgg ccgcgacgag cacggccagg gggcggagcg ccgggcgggc gccgctggag    30840
ctgcgggtca tggggcagtg acctttctgt tgttatggct gcttgttgtc tttgcgggat    30900
ccacagctcg gatccagctg gcgatactac cagcgagcga gtggttttc gtgacccagt     30960 cccgcagtcg ggccccggcg acaacggcgg catcgcggtc ctttgccagg gcacgcacgg    31020
cctcgatcca gtcgccgtcg cgggccagca cggcgggggc atcgcggtag ggctcgagat    31080
ccgaggccac caccgggatg ccgaggcagc cgtactcgag cagcttcagg ttgctcttcg    31140
cgcgattgaa cgggttgtcg cgcagcggtg ccaccgcgac gtcgagtgcc agcgacgcga    31200
gcttctccgg gtactgcgcg atgggcacca tgtcgtgcac ttccgcggcg aacggcgcca    31260
gctcgggcgt gcacaggccg aggaacaccc agtcgatctc gcgatgcgtg gcgcgcacca    31320
cgggctcgag caacttcagg tcttccccat gctgtttcgc ccccgcccag cccacgcgcg    31380
gacgcgcgcc acccgcggga cggttcgcga ggccggccca acgctccgca tcgatcgcgt    31440
tcgggatcac gcgcacgtcc ttcgcgccgc ggccgaaggc ctccgcgagc ggtgcggtgg    31500
acaccacgag gcggtcgcac aacgccaccg cgcgcgcgat gcgctgggcg atgtccgggt    31560
agatcgtcgc cgcatacgga ttgccgggcg gcagttgcgt gagcaggtca tccaggccca    31620
ggaccttcag cgcgcgtccg tggcgcgcga gcacctcgag cgaggtgagc tggtagttgt    31680
ggaagaagtt gtgcgcgagc acggcgtcgg cgtcgaggcg ctgccactcg acgcggttgg    31740
gcgcgcagcc cgtggcgtgc tcgcccatca tcacgacctc gacgcggccc gcgcgctcca    31800
gcgccgcgca cggctggcgc acgcgcacct cgccggagcc ccagcggtcg aacgaaacg     31860 cgcagagccg aaccgcgtgc gtgtcgttgc cgcgcggcgc gaagcgttcc acgggcccgt    31920
agccctcgcc gcccatgcgc aacgccgggt ggtagtgcgg atcgtcgtcg agcaccggct    31980
gccagcgctc gcgcatccac gcctcttcgg aaggaatgac gagcttcgcc accggaacga    32040
cggcatcggc gcgcgcatcg gcgagcaacg ggaagtccgc cgcgatgccg gggcgcgcaa    32100
ggatgtcgaa gcccgctgcg cgcagcccga ggcacaggtg cgccatcgcg aacgccccg     32160 cgcgctcgat ctcgtgcagc gcctgcgcgg agagcgccgc gtcgcggttg accagcgcga    32220
```

```
gacggcccgc cgcgacgctc acctcgcgcg gcgatgcgta gagtgccgcg aggcgctcct    32280
cgccctgcgc gcgcggcgga gcgcccgaga cggcccacgg cccgccgccc gcgatttccc    32340
agccgggaac gcgcacaccg ccggggccca gcaggtcggg cgcgagggca cccgtggagg    32400
ggcctgcgat gccctgctcg aggcgctcga gccagccggc gcggaattcg ctgcaacgcg    32460
catcgacgat cgcgatccac agcgtcgccg cgttgcggat ggcgcgcgcg aacgcggagc    32520
cggtttcgcc gcccaccgga accaggtgcg tgcgcacgcc gcgcccgccc agctcaccgg    32580
gccagcgttt cggcgccctt cgcgtcgaga tcgacgtaca cgtggccgat acgttcgcgg    32640
cagcccttca cgagcgcctc gatgcacgcc accagccgct ccggcgcgtg cgtcgcgtca    32700
atgaaggcgc aaatcgtgcc ggccccgatc gcgcgcgccc acgatgcggg cgcatcggac    32760
gcagctggca ggaacgcggc ctgcgtgcgc gtgcggcgga agtgctccgc gaccacgcgc    32820
tggtggcgct cgcgcgcggc gtcgctttcc tgcgcggcga tgttcaggtc gaggcgatgc    32880
acgagcagct cgcgcagtgc caccacgcgc ctcgcacggc cctcctccgc gaggcgcagc    32940
gcgagatcgg tgacgcccgc ccagccgccg gcgcgcagcc cgccacgctc cagcaacgca    33000
gcgcggcgca gcaccgcgag cccggcgagc ggctggtgtc gcgcgaactc cgcgccgaac    33060
gtggggacga acgccggatc gtagcgttcg ccgtgcgcgc tcagggcatc actgcagccg    33120
tagagaagct cggcgttcgg gttgcgtgcg accgcacccg ccaccgcgct cggcgcgcca    33180
tcggccagcc ggtcgccctc ctccaccagc acgacccatt cgcccttcgc gtccgcgatc    33240
gcgcggttga cgcgcccgag cgccgcgtcg ctcgcgtcgc gctcgaggac cacggtctcc    33300
agggcgatcg cggcagtgct cctggccggc aaggcctcgc gcgccatcca gtggtcgtag    33360
gcatcgccgc ccagcggcgt gcgctcgcgg cggcgtggaa agccgaggca cgccgcggcg    33420
aacaacggat cgatcgttgc gggcacagca tccaccgcgc catcgcgctc cgccgccagc    33480
tcgcgataga gcgccaggta ctcggccgca ttcgcctcga tcgtcttcgg gcggtggtac    33540
ttcaggttct ccgcgacgcg atcgagcgcc gtgcggtcgt cgcgcaggcg cagcaggagg    33600
gccacgatcg cgccgggatc gttgtgcggc agcaggaagc cggtctcgcc atcgcgcacg    33660
cgctcgggaa tggcgccatc gcgcgtgccc gccaccggga tgccgaggcg ctgtgcctcg    33720
ctcaacacca gcagaaggt ctcctccatc gtcgagggca gcaggaccag gtcgatgccg    33780
cgaaggatgc gcgcaggtc cgtcgcggca taggcgccgc gctgcatgat gcccgccgca    33840
ttcgccgccg cttcgagcgc gagatcgcgc ggaccccagg cctcgatcgc gatgcgctgc    33900
cccgccagcc ggcgcgcggc ctcgatgatc aggtgcgcgc ccttgcgccc gccgaagcgg    33960
ccgaggaagg ccacgcgcag caccggccgc gcttcggggc gcggaagcag cggcaggtcg    34020
gcaatgccgt gcccgatgac gcgcagcttc gcttcgcagc tcgcgccgaa gcccttgcgc    34080
atgcgcatcg ccgcgtactc ggacgggcag aggatcacgt cggccgcgtc cacggcatcg    34140
gacgccgcgg cgaagcgcga ttcgaggtag ccggtcacgg acgccggcgc cgtcggcccc    34200
acgatcgcct cgctgcggcc gcgcaggcaa tccacgcatc cgccatcggc gccgcgcgcg    34260
gcggcgcggc cgcacggcag gtcctgcggc ccggtcatca tgttgtagtc ggcgcacagg    34320
tacgagaagt cgtgcgccgt gatgaccacg cgtgcccccg actcacgcgc gatgcgcggc    34380
aggcgcaggc tgttccagcc caccaacgac tggaagtgca cgacgtcgta gcccccggac    34440
agcagttcgc ggaaggccgc ctccacgccc gcgtcggcaa ccgccgcctc gtgcccgatc    34500
acgcggatgc cggcgtcat gcgctcgggg ttcaggcgcg cgagtcgcac gtgcgtcgcc    34560
aggcgctcgg tggtgaagtc ggtccacgcg cgcgggccct cgggcagcac cagcgtcgag    34620
```

```
gcgacgtcct tgcgcagcag gttcaccagc gcgcgcgtgt gctcctcaat gccgccgcgc   34680
gagtcgaggc gatgcagcac ctgcagcacg cgcgggcggc ccggcatccg ctcgcgctcg   34740
gccgcggcgt tgacgcgctc ggcggcgcgc cgcagcgggt tcgcgatcgc ccacgcgcgc   34800
acgcccgcga cgtaggtggg ccagcggcgc tcgaggcgca cgcggttggc ctcgcgcgcg   34860
gcgtcgatgc cggccacccc gccgaacgag gcctcgcccg cgtggtgcac gtagacgtcg   34920
tcgcagcacg cgatctgcca gtcccggtcc agcgcgcgca tcgagaggtc gttttcctcg   34980
ccgtagccgc ggccatagag cgagtcgaac gggccgcatt gcacccacac ctcgcggcgc   35040
accagcatgc agaagccgac cgccgtcggc aggcgcggat actcgcggcg gctggcgcgc   35100
gcgacgcagg cggagatggc atcgacgtcc ggctcgccgt cgggccgctc gaagatatcg   35160
gcgacgccgg gcaggctgag gatcgtcgcg cggttggaga gcgggcacac gatgccgacc   35220
cgcgcatcgc tgtcgcggca acgcagcagg ccctcgagcc aaccggggcc gacctgcgta   35280
tccgaattga gcaccacgaa gtcgccgccg ctgccggcca ggcccgcagc gaccgcgcct   35340
gcgaagccga ggttcttcgc attggtgacg acacgagtgc cggcacgacg cgccgcgaag   35400
ctgcccagca accggcgag gcgcggatcg gtgctcgcgt catcgacgag gacgatgccg   35460
tgcgcggcgc ccgtgtggcg ggccagcgac gcgaggcagc gttcggtgtc gtcgtggccg   35520
ttgaagaccg ggacgacgac tagcgccggc gccatccgac cggcgcttcg agctgggcca   35580
atcgcgccag caggcgctgg tgctcctgcg agagtgcctc gagctgcttc tgcgaggcga   35640
cgtaggcgcc tccatgcgct cccaggtgcg tgcgcgcctc ctcgagctgc cgcagcgact   35700
gctcgtggcg accggagacg tcgtggtcgc ggtcggagag cagcgagaag cgcccggccc   35760
ccgccgtcac cgcctcgcgc tcgccgcaca gggcgaggaa gtacatcgca tcggcgacgc   35820
ccgccgcggg tttcgcagcc tccggcgccg aagcttgcag caactgcacg gcgtcgggca   35880
ccgcgtgcag cggccagatc gccgaatacg catcgacgcg ttgcccgaac agggccacct   35940
ccgggaaccg cgccttcagc acggcgagga attcgtgctc gtagagctcg cgcacgtgat   36000
gcgggttgcg gtagtcgcgc tggtccgagt acacctcgcg gttcggcgtc gagaccagca   36060
gcaggccgcc gggcgccagc acgcgcttcg cttcgtcgag caggcgctcg ggatcgggaa   36120
tgtgctcgag cgtctcgaag gagacgagga gatcgatgct tgcgtcatcg cacggcagcg   36180
actcgcagcg gccctcgacg tactgcaggt tctgcgcggc accatagcgg cggcgcgcct   36240
gcgcgatggt ctcggcggcg acatccgcgc ccaccacgga cttcgcgcgc gtcgccagca   36300
gcgccgagcc gtagccctcc ccgcaggcga tgtcgaggac gcggcagcct ccggcgagcg   36360
gcaacgcaaa gtggtagcgg tgccagtgct cgtaccagat ctcgccctcg aagccgggct   36420
ggaaacgttc gtgttccatc gggagagtat aggtggatgt gcaaccgccc tccggagagg   36480
gcggttgcga tgatcttatt cgagatcggc tgctacggaa gcaccggcaa cggctgcggc   36540
ggcgccaccg accatccggt gcccgcgccc agcaggttcg cgctgccgag cgtggtgagg   36600
ccgtccatca ggcgcaccgt gatgcggcca tcgacattct tgaacaccat gtcgagcttg   36660
ccgtcgccat cgaagtcgag cagttgcgtg acggtccagc ccgcccccgc cggcagcacg   36720
tccgccgcgc tgaggatggc ggtgccgttc atcaggcgca cgtgcgcacg gccgtcggtg   36780
tggcggaaca cgatgtcacc gcgcccgtcg cggttcatgt cgcccacgtg gctcacgatc   36840
cagccggtgc ccgcgccgag gagctcggaa ccggcgccga acgcggtgcc gttcatgatg   36900
aagagatgcg cgcggccatc ggtgtggcgg aagaacatgt ccgccttgcc gtcgccgctc   36960
acgtcgccca ggtgcgtcac cgtccagccg ctggcgggcg agaggaagcc cgcgccggcg   37020
```

```
gtgatggtgg tgccgttcat caggtagatg tagccgcggc cgtcagcgtg gatgaagacg    37080
atgtcgtccc tgccgtcgcc gttgaggtcc ccggtggcca cgactctcca gcccgtcgcc    37140
ggccccagca gctgctggct gccgatgatg ccgtgccat  ccatcagcca caggtgcgag     37200
cggccgtcgg cgttgcgcag caggagatcc gccttgccgt cgccgttcat gtcggcggtg    37260
cggtcgatgc tccagccgag gccggcgccc agcagctcct tgccgccggt caccgtgagg    37320
ccgttcatcg tgtacacgta cacgcgcccg tcggtgtggg gggatcctct agagtcgacc    37380
tgcaggcatg caagcttgag tattctatag tctcacctaa atagcttggc gtaatcatgg    37440
tcatagctgt ttcctgtgtg aaattgttat ccgctcacaa ttcacacaac atacgagccg    37500
gaagcat                                                             37507

<210> SEQ ID NO 3
<211> LENGTH: 26
<212> TYPE: DNA
<213> ORGANISM: Artificial sequence
<220> FEATURE:
<223> OTHER INFORMATION: Sense primer.

<400> SEQUENCE: 3
ggsccskcss tsdcsrtsga yacsgc                                              26

<210> SEQ ID NO 4
<211> LENGTH: 23
<212> TYPE: DNA
<213> ORGANISM: Artificial sequence
<220> FEATURE:
<223> OTHER INFORMATION: Antisens primer.

<400> SEQUENCE: 4
gcbbssryyt cdatsggrtc scc                                                 23

<210> SEQ ID NO 5
<211> LENGTH: 773
<212> TYPE: DNA
<213> ORGANISM: Artificial sequence
<220> FEATURE:
<223> OTHER INFORMATION: OriT derived from plasmid RP4.

<400> SEQUENCE: 5
gatctgtgat gtacttcacc agctccgcga agtcgctctt cttgattgga gcgcatgggg        60
acgtgcttgg caatcacgcg cacccccgg  ccgttttagc ggctaaaaaa gtcatggctc       120
tgccctcggg cggaccacgc ccatcatgac cttgccaagc tcgtcctgct tctcttcgat       180
cttcgccagc agggcgagga tcgtggcatc accgaaccgc gccgtgcgcg ggtcgtcggt       240
gagccagagt ttcagcaggc cgcccaggcg gcccaggtcg ccattgatgc gggccagctc       300
gcggacgtgc tcatagtcca cgacgcccgt gattttgtag ccctggccga cggccagcag       360
gtaggccgac aggctcatgc cggccgccgc cgccttttcc tcaatcgctc ttcgttcgtc       420
tggaaggcag tacaccttga taggtgggct gcccttcctg gttggcttgg tttcatcagc       480
catccgcttg ccctcatctg ttacgccggc ggtagccggc cagcctcgca gagcaggatt       540
cccgttgagc accgccaggt gcgaataagg gacagtgaag aaggaacacc cgctcgcggg       600
tgggcctact tcacctatcc tgcccggctg acgccgttgg atacaccaag gaaagtctac       660
acgaaccctt tggcaaaatc ctgtatatcg tgcgaaaaag gatggatata ccgaaaaaat       720
cgctataatg accccgaagc agggttatgc agcggaaaag atccgtcgga tct            773
```

<210> SEQ ID NO 6
<211> LENGTH: 2012
<212> TYPE: DNA
<213> ORGANISM: Artificial sequence
<220> FEATURE:
<223> OTHER INFORMATION: Psi C31 integrase.

<400> SEQUENCE: 6

| | | | | | |
|---|---|---|---|---|---|
| agatctcccg | tactgacgga | cacaccgaag | ccccggcggc | aaccctcagc | ggatgccccg | 60 |
| gggcttcacg | ttttcccagg | tcagaagcgg | ttttcgggag | tagtgcccca | actggggtaa | 120 |
| cctttgagtt | ctctcagttg | ggggcgtagg | gtcgccgaca | tgacacaagg | ggttgtgacc | 180 |
| ggggtggaca | cgtacgcggg | tgcttacgac | cgtcagtcgc | gcgagcgcga | gaattcgagc | 240 |
| gcagcaagcc | cagcgacaca | gcgtagcgcc | aacgaagaca | aggcggccga | ccttcagcgc | 300 |
| gaagtcgagc | gcgacggggg | ccggttcagg | ttcgtcgggc | atttcagcga | agcgccgggc | 360 |
| acgtcggcgt | tcgggacggc | ggagcgcccg | gagttcgaac | gcatcctgaa | cgaatgccgc | 420 |
| gccgggcggc | tcaacatgat | cattgtctat | gacgtgtcgc | gcttctcgcg | cctgaaggtc | 480 |
| atggacgcga | ttccgattgt | ctcggaattg | ctcgccctgg | gcgtgacgat | tgtttccact | 540 |
| caggaaggcg | tcttccggca | gggaaacgtc | atggaccgga | ttcacctgat | tatgcggctc | 600 |
| gacgcgtcgc | acaaagaatc | ttcgctgaag | tcggcgaaga | ttctcgacac | gaagaacctt | 660 |
| cagcgcgaat | gggcgggtta | cgtcggcggg | aaggcgcctt | acggcttcga | gcttgtttcg | 720 |
| gagacgaagg | agatcacgcg | caacggccga | atggtcaatg | tcgtcatcaa | caagcttgcg | 780 |
| cactcgacca | ctcccccttac | cggacccttc | gagttcgagc | ccgacgtaat | ccggtggtgg | 840 |
| tggcgtgaga | tcaagacgca | caaacacctt | cccttcaagc | cgggcagtca | agccgccatt | 900 |
| caccccgggca | gcatcacggg | gctttgtaag | cgcatggacg | ctgacgccgt | gccgacccgg | 960 |
| ggcgagacga | ttgggaagaa | gaccgcttca | agcgcctggg | acccggcaac | cgttatgcga | 1020 |
| atccttcggg | acccgcgtat | tgcgggcttc | gccgctgagg | tgatctacaa | gaagaagccg | 1080 |
| gacggcacgc | cgaccacgaa | gattgagggt | taccgcattc | agcgcgaccc | gatcacgctc | 1140 |
| cggccggtcg | agcttgattg | cggaccgatc | atcgagcccg | ctgagtggta | tgagcttcag | 1200 |
| gcgtggttgg | acggcagggg | gcgcggcaag | gggctttccc | ggggggcaagc | cattctgtcc | 1260 |
| gccatggaca | agctgtactg | cgagtgtggc | gccgtcatga | cttcgaagcg | cggggaagaa | 1320 |
| tcgatcaagg | actcttaccg | ctgccgtcgc | cggaaggtgg | tcgacccgtc | cgcacctggg | 1380 |
| cagcacgaag | gcacgtgcaa | cgtcagcatg | gcggcactcg | acaagttcgt | tgcggaacgc | 1440 |
| atcttcaaca | agatcaggca | cgccgaaggc | gacgaagaga | cgttggcgct | tctgtgggaa | 1500 |
| gccgcccgac | gcttcggcaa | gctcactgag | gcgcctgaga | agagcggcga | acgggcgaac | 1560 |
| cttgttgcgg | agcgcgccga | cgccctgaac | gcccttgaag | agctgtacga | agaccgcgcg | 1620 |
| gcaggcgcgt | acgacggacc | cgttggcagg | aagcacttcc | ggaagcaaca | ggcagcgctg | 1680 |
| acgctccggc | agcaaggggc | ggaagagcgg | cttgccgaac | ttgaagccgc | cgaagccccg | 1740 |
| aagcttcccc | ttgaccaatg | gttccccgaa | gacgccgacg | ctgacccgac | cggccctaag | 1800 |
| tcgtggtggg | ggcgcgcgtc | agtagacgac | aagcgcgtgt | tcgtcgggct | cttcgtagac | 1860 |
| aagatcgttg | tcacgaagtc | gactacgggc | aggggcagg | gaacgcccat | cgagaagcgc | 1920 |
| gcttcgatca | cgtgggcgaa | gccgccgacc | gacgacgacg | aagacgacgc | ccaggacggc | 1980 |
| acggaagacg | tagcggcgta | gcgagacacc | cg | | | 2012 |

```
<210> SEQ ID NO 7
<211> LENGTH: 84
<212> TYPE: DNA
<213> ORGANISM: Artificial sequence
<220> FEATURE:
<223> OTHER INFORMATION: Left arm of pPAOI6 transposon.

<400> SEQUENCE: 7
ctgtctctta tacacatctc aaccatcatc gatgaattttt ctcgggtgtt ctcgcatatt      60
ggctcgaatt cgagctcggt accc                                             84

<210> SEQ ID NO 8
<211> LENGTH: 94
<212> TYPE: DNA
<213> ORGANISM: Artificial sequence
<220> FEATURE:
<223> OTHER INFORMATION: Right arm of pPAOI6 transposon.

<400> SEQUENCE: 8
gatcctctag agtcgacctg caggcatgca agcttgccaa cgactacgca ctagccaaca      60
agagcttcag ggttgagatg tgtataagag acag                                  94

<210> SEQ ID NO 9
<211> LENGTH: 31
<212> TYPE: DNA
<213> ORGANISM: Artificial sequence
<220> FEATURE:
<223> OTHER INFORMATION: Primer AmF.

<400> SEQUENCE: 9
ccctaagatc tggttcatgt gcagctccat c                                     31

<210> SEQ ID NO 10
<211> LENGTH: 34
<212> TYPE: DNA
<213> ORGANISM: Artificial sequence
<220> FEATURE:
<223> OTHER INFORMATION: Primer AmR.

<400> SEQUENCE: 10
tagtacccgg ggatccaacg tcatctcgtt ctcc                                  34

<210> SEQ ID NO 11
<211> LENGTH: 32
<212> TYPE: DNA
<213> ORGANISM: Artificial sequence
<220> FEATURE:
<223> OTHER INFORMATION: Primer OriTF.

<400> SEQUENCE: 11
gcggtagatc tgtgatgtac ttcaccagct cc                                    32

<210> SEQ ID NO 12
<211> LENGTH: 37
<212> TYPE: DNA
<213> ORGANISM: Artificial sequence
<220> FEATURE:
<223> OTHER INFORMATION: Primer OriTR.

<400> SEQUENCE: 12
tagtacccgg ggatccgacg gatcttttcc gctgcat                               37

<210> SEQ ID NO 13
<211> LENGTH: 32
<212> TYPE: DNA
<213> ORGANISM: Artificial sequence
```

```
<220> FEATURE:
<223> OTHER INFORMATION: Primer Fint.

<400> SEQUENCE: 13
aacaaagatc tcccgtactg acggacacac cg                                32

<210> SEQ ID NO 14
<211> LENGTH: 21
<212> TYPE: DNA
<213> ORGANISM: Artificial sequence
<220> FEATURE:
<223> OTHER INFORMATION: Primer PJ.

<400> SEQUENCE: 14
cgggtgtctc gcatcgccgc t                                            21

<210> SEQ ID NO 15
<211> LENGTH: 30
<212> TYPE: DNA
<213> ORGANISM: Artificial sequence
<220> FEATURE:
<223> OTHER INFORMATION: Primer amyE-BamHI.

<400> SEQUENCE: 15
atcgcaggat cctgaggact ctcgaacccg                                   30

<210> SEQ ID NO 16
<211> LENGTH: 37
<212> TYPE: DNA
<213> ORGANISM: Artificial sequence
<220> FEATURE:
<223> OTHER INFORMATION: Primer amyE-EcoRI.

<400> SEQUENCE: 16
cgactgaatt cagatctagc gtgtaaattc cgtctgc                           37
```

METHOD FOR THE EXPRESSION OF UNKNOWN ENVIRONMENTAL DNA INTO ADAPTED HOST CELLS

Figure 1A:
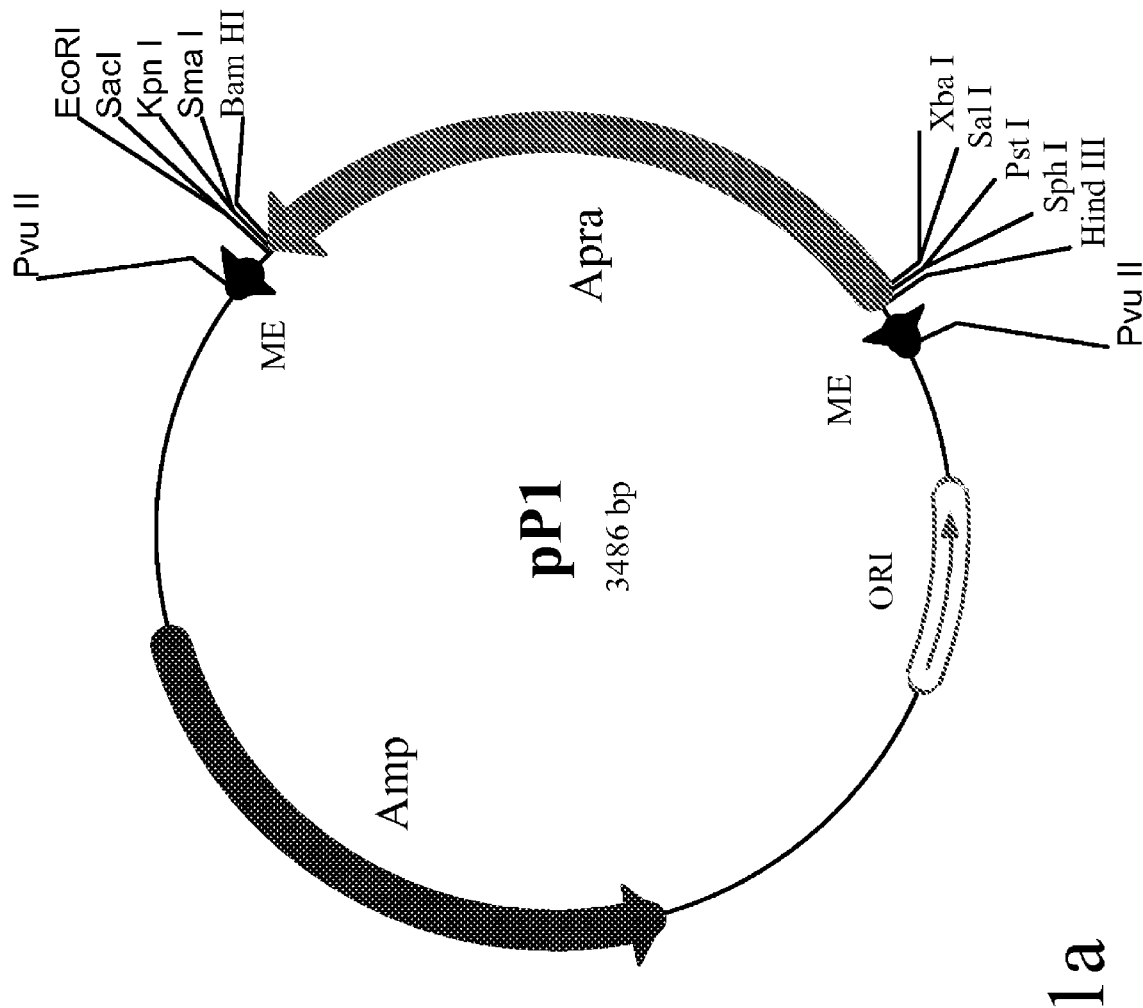

This application is the US national phase of international application PCT/EP2003/007765 filed 17 Jul. 2003 which designated the U.S. and claims benefit of EP 02291871.8, dated 24 Jul. 2002, the entire contents of each of which are hereby incorporated by reference.

INTRODUCTION AND BACKGROUND

The present invention relates to methods and compositions for nucleic acid production, analysis and cloning. The present invention discloses tools and methods for the production and analysis of libraries of polynucleotides, particularly metagenomic libraries, which can be used to identify novel pathways, novel enzymes and novel metabolites of interest in various areas, including pharmaceutical, cosmetic, agrochemical and/or food industry.

Drug discovery process is based on two main fields, namely combinatorial chemistry and natural products. Combinatorial chemistry has shown its ability to generate huge amounts of molecules, but with limited chemical diversity. At the opposite, natural products have been the most predominant source of structural and molecular diversity. However, the exploitation of this diversity is strongly hampered by their limited access, complex identification and purification processes, as well as by their production.

Microorganisms are known to synthesize a large diversity of natural compounds which are already widely used in therapeutic, agriculture, food and industrial areas. However, this promising approach to the identification of new natural compounds has always been considerably limited by the principal technological bolts of isolating and in vitro propagating the huge diversity of bacteria. Most microorganisms living in a natural, complex environment (soil, digestive tract, sea, etc. . . . ) have not been cultivated because their optimal living conditions are either unknown or difficult to reproduce. Numbers of scientific publications relate this fact and it is now assumed that less than about 1% of the total bacterial diversity (when all environments are considered together) have been isolated and cultivated (Amann et al, 1995).

New approaches have been developed to try to overpass the critical step of isolation, and to access directly to the huge genetic potential established by the microbial adaptation processes through their long evolution. These approaches are called "Metagenomic" because they address a plurality of genomes of a whole bacterial community, without any distinction (metagenome).

Metagenomics involve direct extraction of DNAs from environmental samples and their propagation and expression into a cultivated host cell, typically a bacteria. Metagenomic has been firstly developed for the identification of new bacterial phylum (Pace. 1997). This use is based on the specific cloning of genes recognized for their interest as phylogenetic markers, such as 16S rDNA genes. Further developments of Metagenomics relate to the detection and cloning of genes coding for proteins with environmental or industrial interest. These first two applications of metagenomic involve a first step of gene selection (generally using PCR) before cloning. In the case of protein production, the cloning vector used are preferentially also expression vectors, i.e., they contain regulatory sequences upstream of the cloning site causing expression of the cloned gene in a given bacterial host strain.

More recent developments of metagenomic consider the total metagenome cloned without any selection and/or identification, to establish random "Metagenomic DNA libraries". This provides an access to the whole genetic potential of bacterial diversity without any "a priori" selection. Metagenomic DNA libraries are composed of hundreds of thousands of clones which differ from each other by the environmental DNA fragments which have been cloned. In this respect, large DNA fragments have been cloned (more than 30 Kb), so as to (i) limit the number of clones which have to be analysed and (ii) to be able to recover whole biosynthetic pathways for the identification of new metabolites resulting from multi enzymatic synthesis. This last point is of particular interest for bacterial metagenomic libraries since, most the biosynthetic pathways have been found to be naturally organised in a same cluster of DNA and even in the same operon in bacteria. Nevertheless, the heterologuous expression of a whole biosynthetic pathways (large DNA fragment) needs a much more improved system than a simple expression vector to have a full and stable expression.

Except for the identification and characterisation of bacterial community at the phylogenetic or diversity levels, metagenomic libraries produced in the prior art are gene expression libraries, i.e., the environmental DNA fragments are cloned downstream of a functional promoter, to allow their expression and analysis. In this regard, WO99/45154 and WO96/34112 relate to combinatorial gene expression libraries which comprise a pool of expression constructs where each expression construct contains DNA which is operably associated with one or more regulatory regions that drive expression of genes in an appropriate organisms. Furthermore, the expression constructs used in these methods have a very limited and invariable host range. Similarly, WO 01/40497 relates to the construction and use of expression vectors which can be transferred in one chosen expression bacterial host of the *Streptomyces* genus. All these approaches are, however, very limited since they require the presence of expression signals and confer invariable or very limited host range capabilities. Furthermore, most (if not all) metagenomic DNA libraries have been established in *E. coli* which is the most efficient cloning system. However, most environmental DNA are not expressed or functionally active in *E. coli*. In particular, functional analysis in *E. coli* of genes cloned from G+C rich organisms, such as *Actinomyces*, could be limited by the lack of adequate transcription and translation system. Also, posttranslational modification system in *E. coli* is not operative on heterologous proteins from Actinomicetes and some specific substrates for proteins activity are not present in *E. coli*.

The stable maintenance of large foreign DNA fragments (>10 Kb) into a selected host cell is one of the key points for academic research or applied industrial purposes. Usually, the vector carrying the foreign DNA is maintained by cultivating the host cells in a medium with a vector-specific selective pressure (resistance to an antibiotic for example). However, when large foreign DNA fragments are cloned and/or expressed, their propagation and/or expression require energy, which is not allocated for cell growth anymore. As a consequence of this new resource allocation (nutrients/energy), it is not unusual to have a genetic rearrangement of the foreign DNA (deletion, modification etc. . . . ) as a recombinant cell reaction. This results in the modification of the foreign genetic information and in the loss of DNA functionality. This can be observed without any loss of the selective pressure carried by the vector. As a result, the recombinant clone is no more exploitable for genetic or functional analysis.

Thus, the exploitation of the huge potential of metagenomics for the discovery of new natural compounds, pathways or genes cannot be achieved with currently existing methods. Alternative technologies and processes must be developed, to allow stable maintenance and propagation of large foreign DNAs into host cells for production of efficient libraries and functional screening in a large variety of host cell species, including Bacillus or Streptomyces, to take full account of the huge diversity of the environmental DNAs.

SUMMARY OF THE INVENTION

The present invention discloses improved tools and methods for the production and analysis of libraries of polynucleotides, particularly metagenomic libraries, which can be used to identify and produce novel pathways, novel enzymes and novel metabolites of interest.

More particularly, the invention now proposes to keep the advantage of high efficient cloning in E. coli and to modify the properties of metagenomic libraries, to allow genetic and functional analyses of particular selected clones in any appropriate system, thereby making possible the stable maintenance and propagation, the analysis and/or the expression of the huge diversity of metagenomic libraries. According to the invention, polynucleotide libraries can be produced in any convenient cloning system, such as E. coli, and then modified, depending on the desired selection or screening system, to adapt host range and/or properties of the library (or a portion thereof).

A particular object of this invention resides more specifically in a method of analysing a library of polynucleotides, said polynucleotides being contained in cloning vectors having a particular host range, the method comprising (i) selecting cloning vectors in the library which contain a polynucleotide having a particular characteristic, (ii) modifying said selected cloning vectors to allow a transfer of said vectors into a selected host cell and integration of the polynucleotide contained in said vectors into the genome of the selected host cell, and (iii) analysing the polynucleotides contained in said modified vectors upon transfer of said modified vectors into said selected host cell.

An other object of this invention is a library of polynucleotides, wherein said library comprises a plurality of environmental DNA fragments cloned into cloning vectors, wherein said environmental DNA fragments contain a common molecular characteristic and wherein said cloning vectors are E. coli cloning vectors comprising a target polynucleotide construct allowing (i) transfer of the environmental DNA into a selected host cell distinct from E. coli, (ii) integration of the environmental DNA into the genome of a selected host cell, and (iii) stable maintenance and propagation of the environmental DNA into the selected host cell.

A further object of this invention is a method of producing modified libraries of polynucleotides, the method comprising selecting a sub-population of clones in a first library, based on the presence or absence of a characteristic of interest, and modifying the properties of said selected clones to allow their functional analysis or expression.

The modification in the library or cloning vector is typically obtained by targeted insertion of a polynucleotide construct, preferably using transposable elements, either in vitro or in vivo.

The integration into the genome of the selected host cell is typically obtained by site specific integration or by homologous or heterologous DNA/DNA recombination.

The invention is particularly suited for producing and analysing genetic diversity (metagenomic libraries), to identify new genes and isolate new metabolites, drugs, enzymes, antibiotics, etc.

LEGEND TO THE FIGURES

Figure 1B:
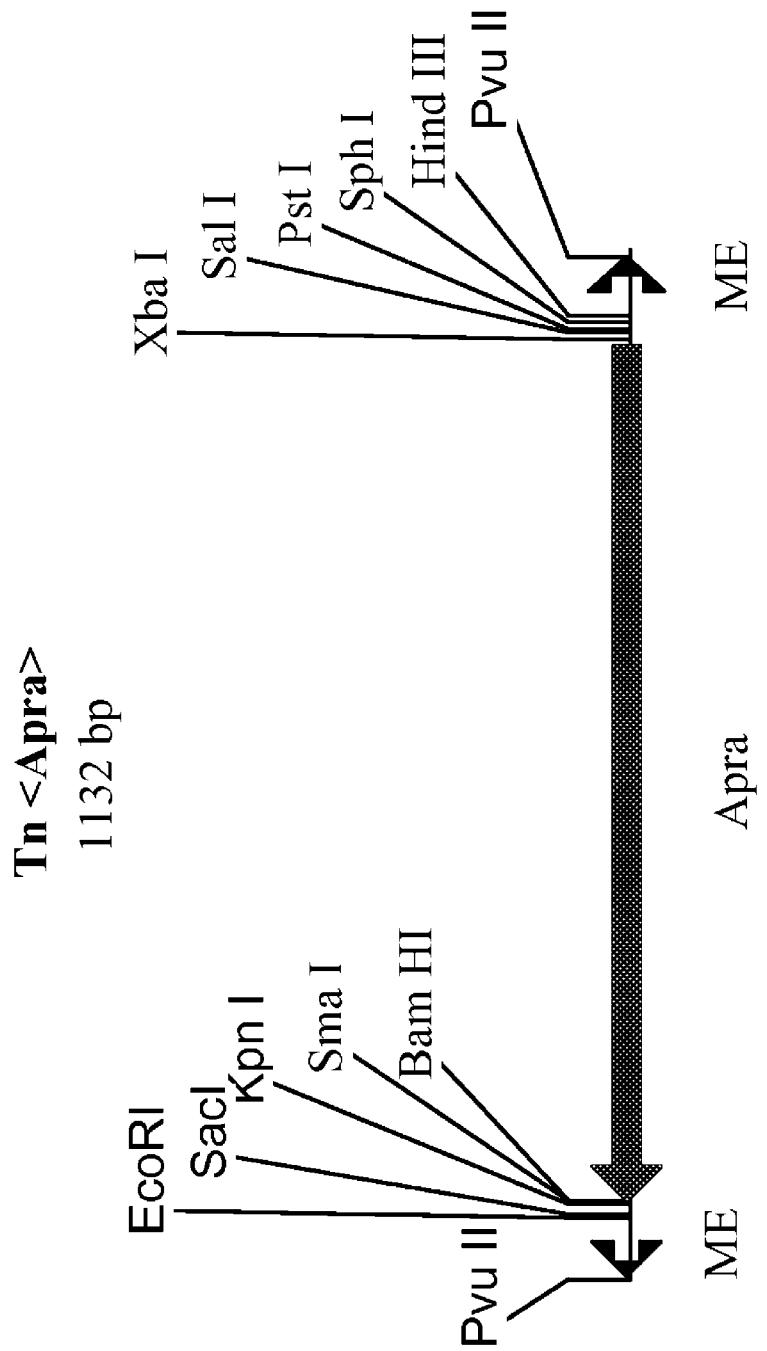

FIG. 1: Map of pP1 vector carrying transposable construct Tn<Apra> FIG. 1a. Excised transposable construct is 1132 bps in size. It contains two mosaic ends (ME) and a gene conferring resistance to apramycine (Apra) FIG. 1b.

Figure 2A:
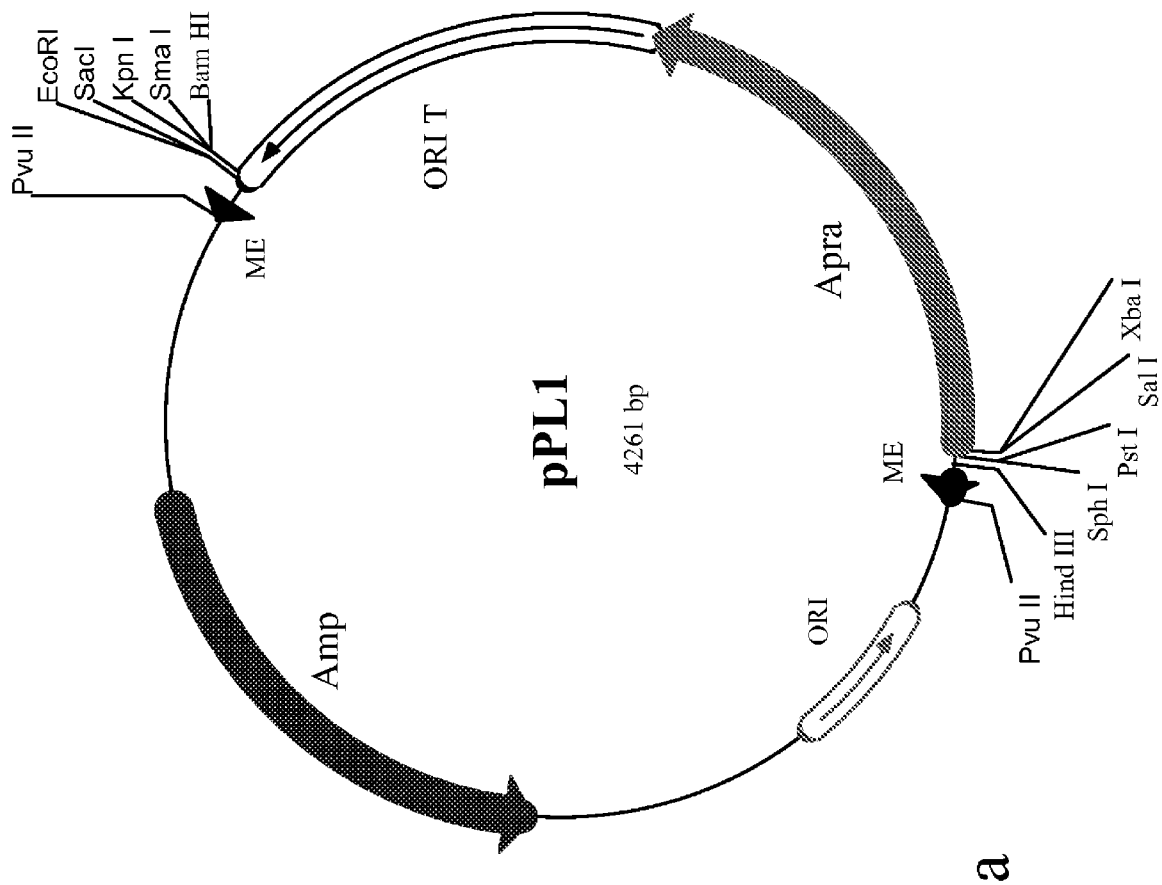
Figure 2B:
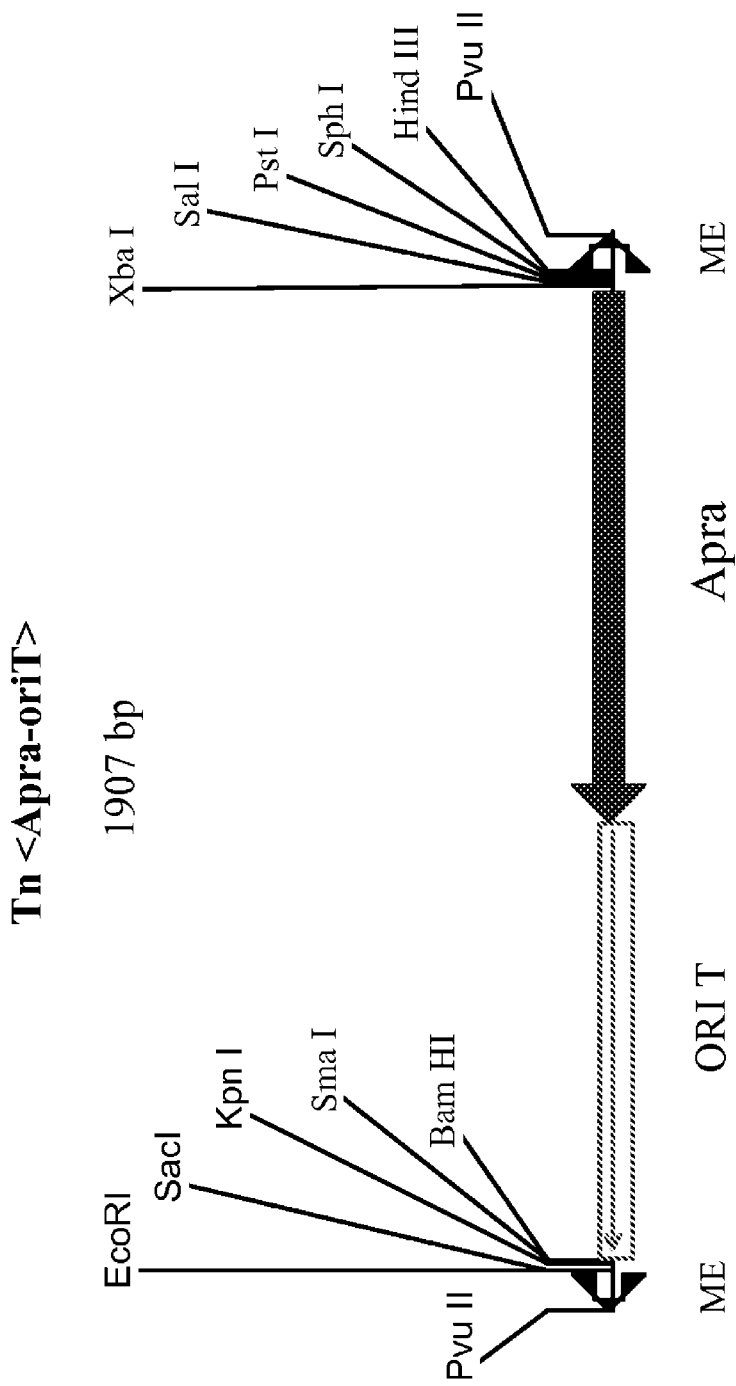

FIG. 2: pPL1 Vector (FIG. 2a) that carries the conjugative transposable construct Tn<Apra-oriT> (FIG. 2b). The nucleotide sequence of the transposable construct contains an origin of transfer (oriT) and a gene conferring resistance to apramycine (Apra). Direction of DNA transfer at oriT is shown by an arrow.

Figure 3A:
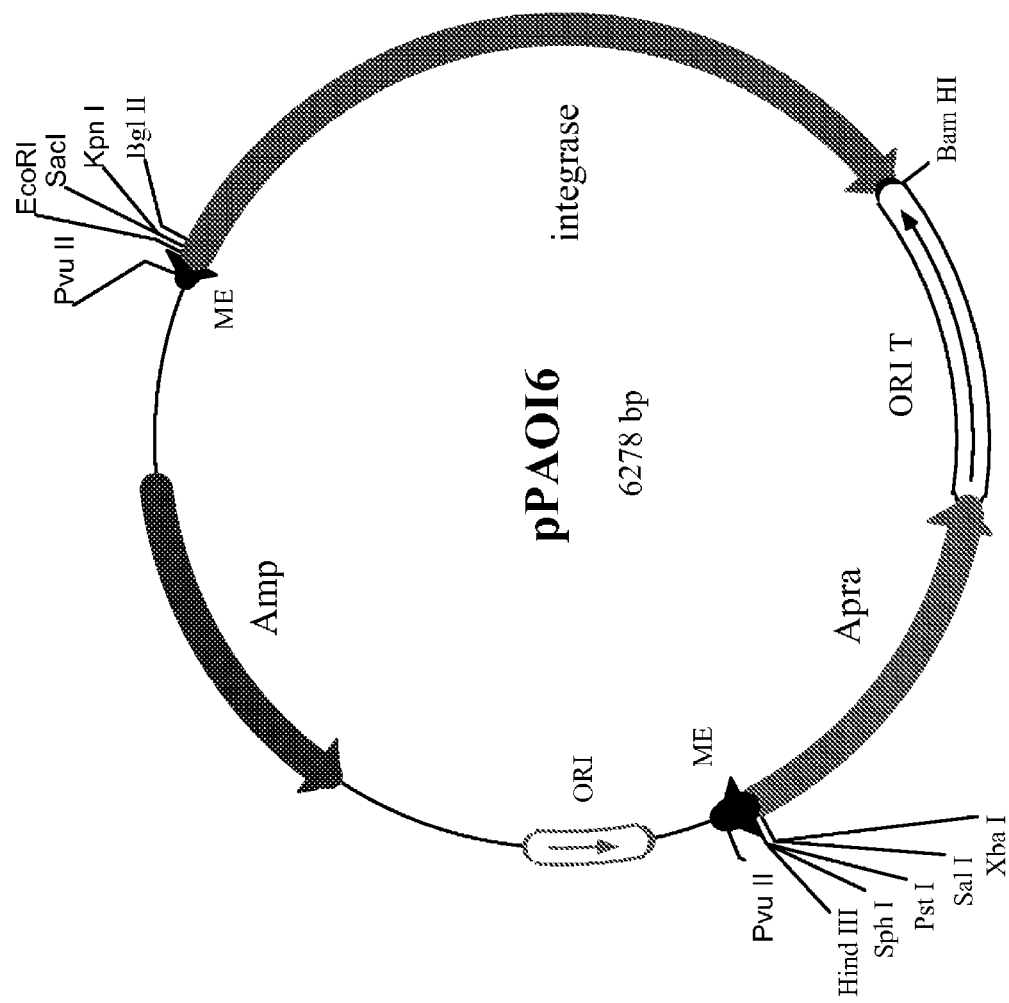
Figure 3B:
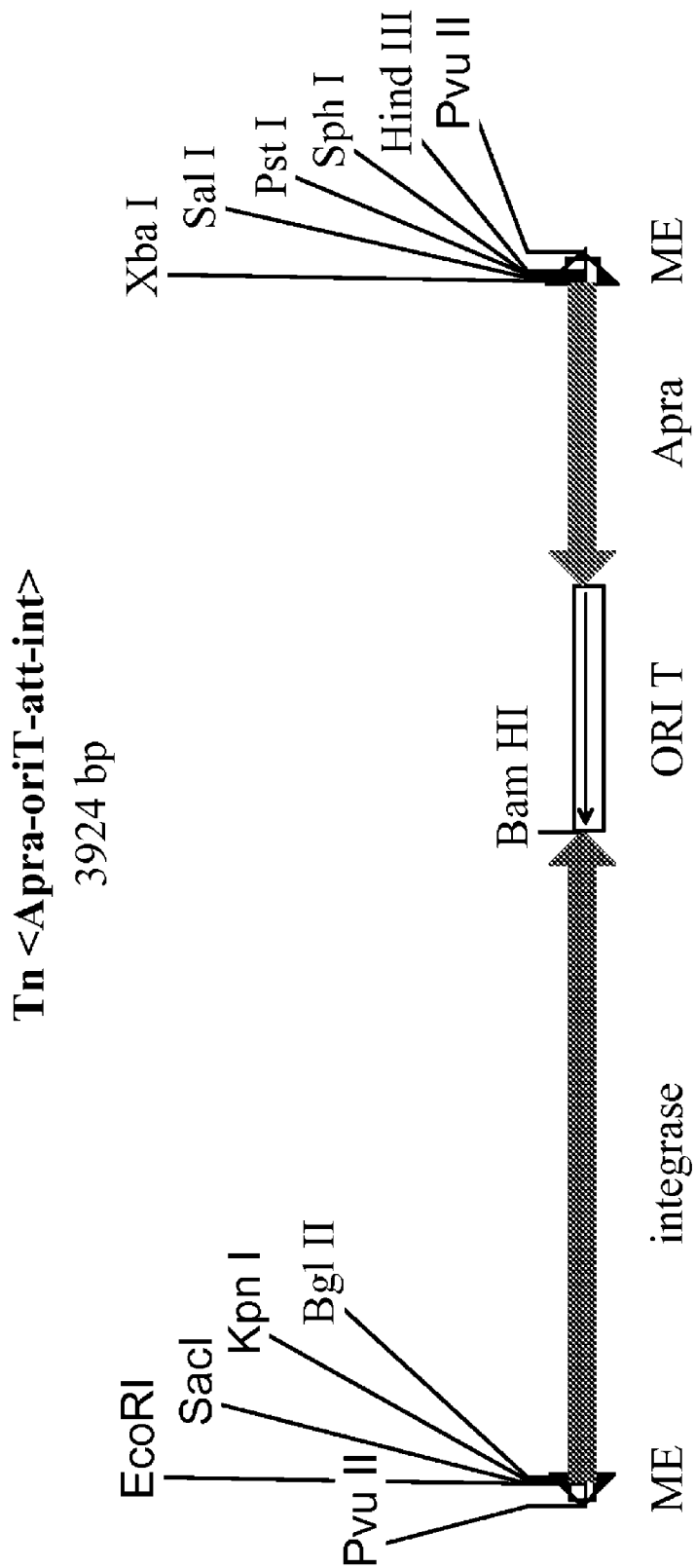

FIG. 3: Transposable construct Tn<Apra-oriT-att-int> (FIG. 3a) on vector pPAOI6 (FIG. 3b). The transposable construct contains ΦC31 integrase gene and attachment DNA sequence for site specific integration, origin of transfer and gene for selection. The orientation of genes and direction of DNA transfer are marked by arrows.

Figure 4A:
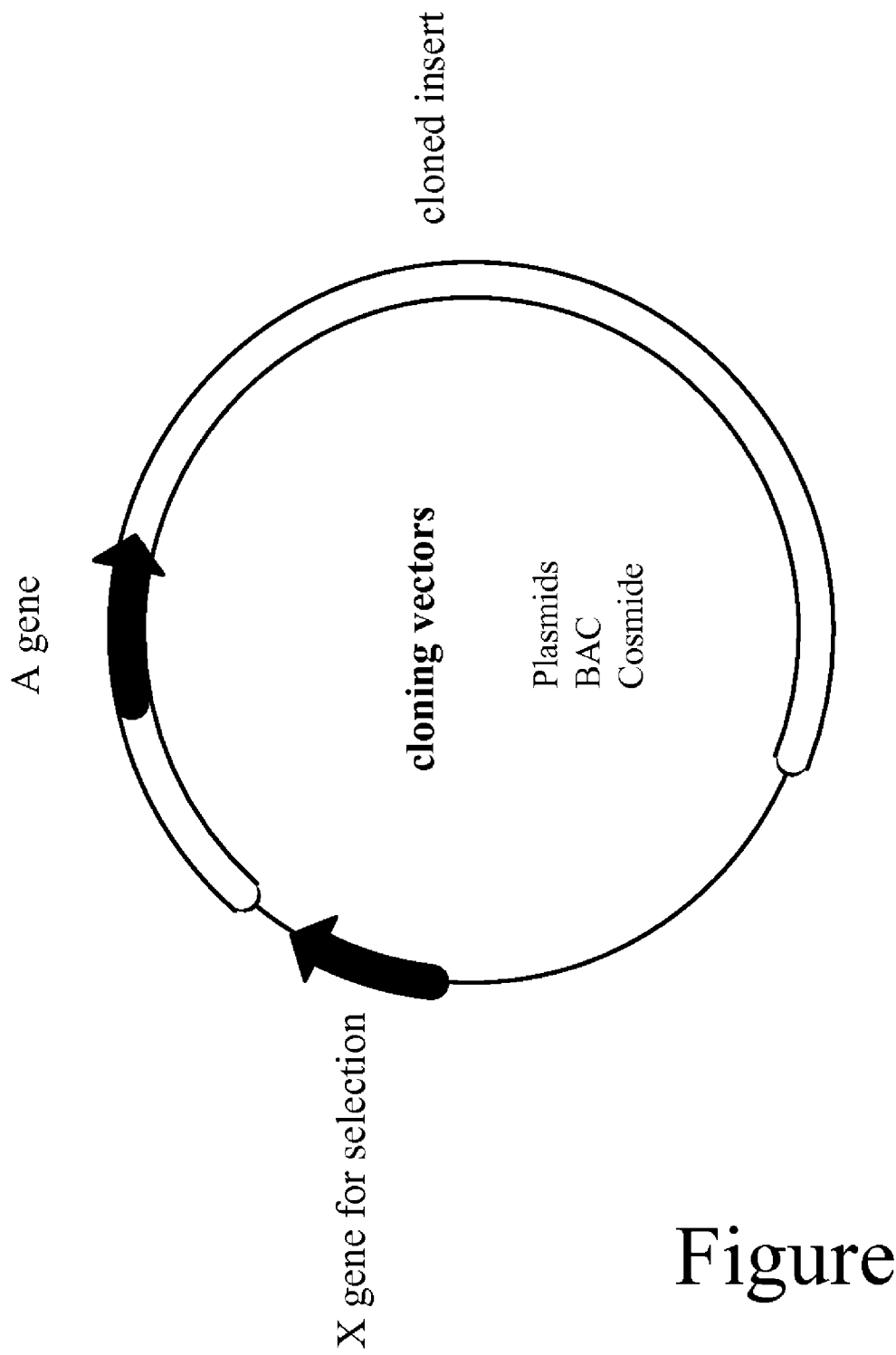
Figure 4B:
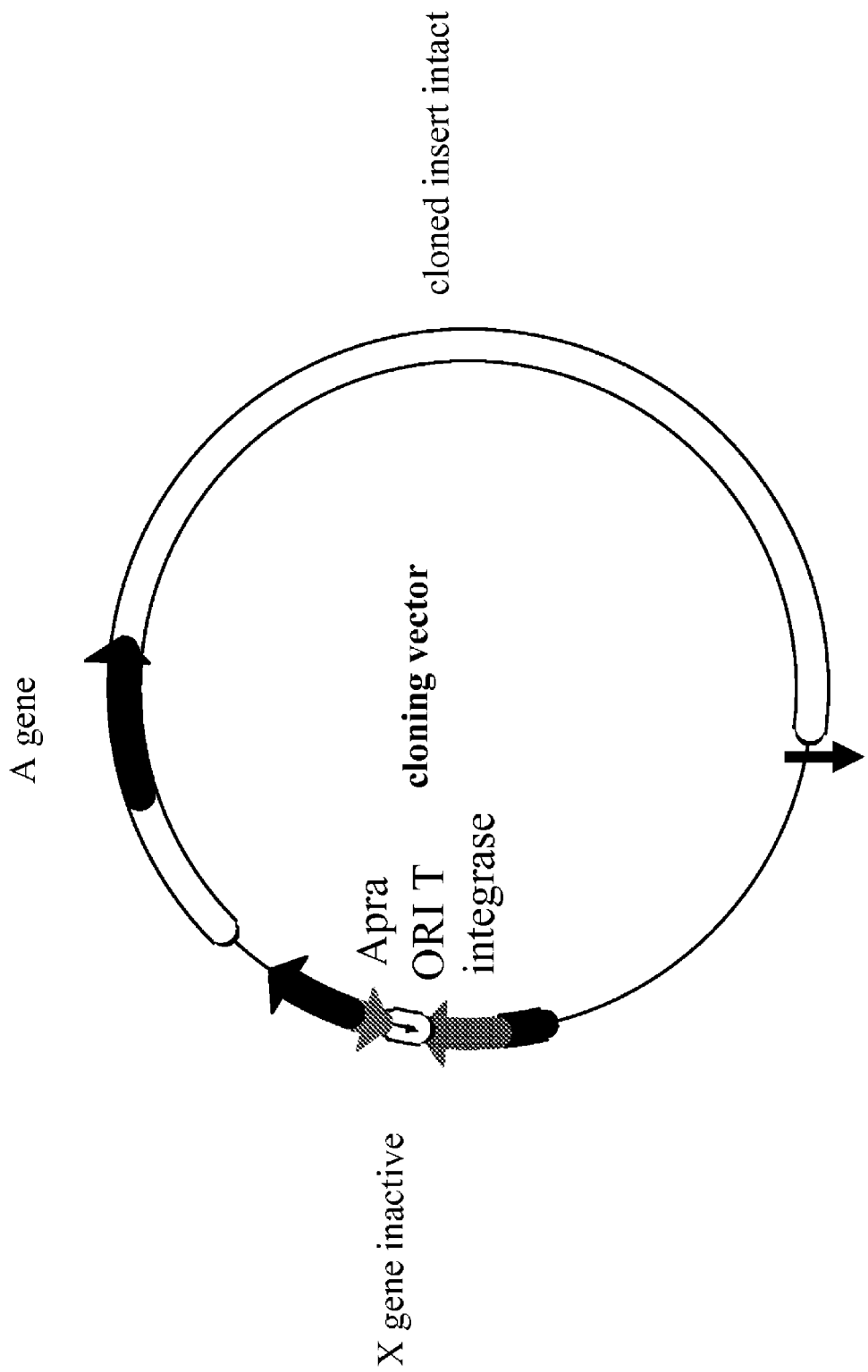
Figure 4C:
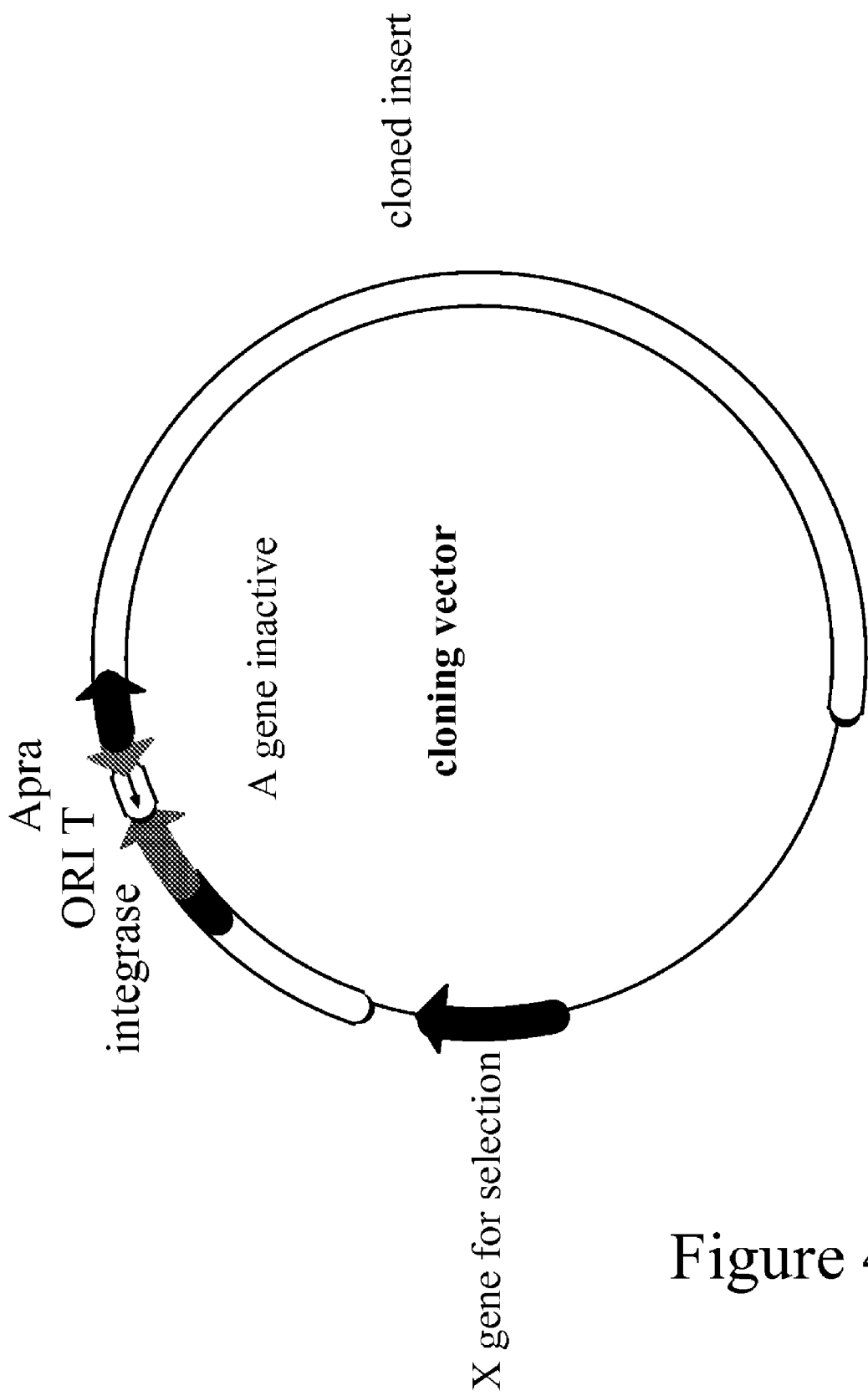

FIG. 4: This figure shows any target DNA suitable for insertion of transposable construct (FIG. 4a). Insertion of conjugative and site specific integrative transposable construct Tn<Apra-oriT-int> is shown on FIG. 4 b and c. Insertion of transposable construct into selective gene marker carried on original vector is shown on FIG. 4b. In this event, the cloned insert is intact and can be transferred to heterologous host. Insertion of transposable construct into cloned DNA insert results in gene inactivation (FIG. 4c).

Figure 5:
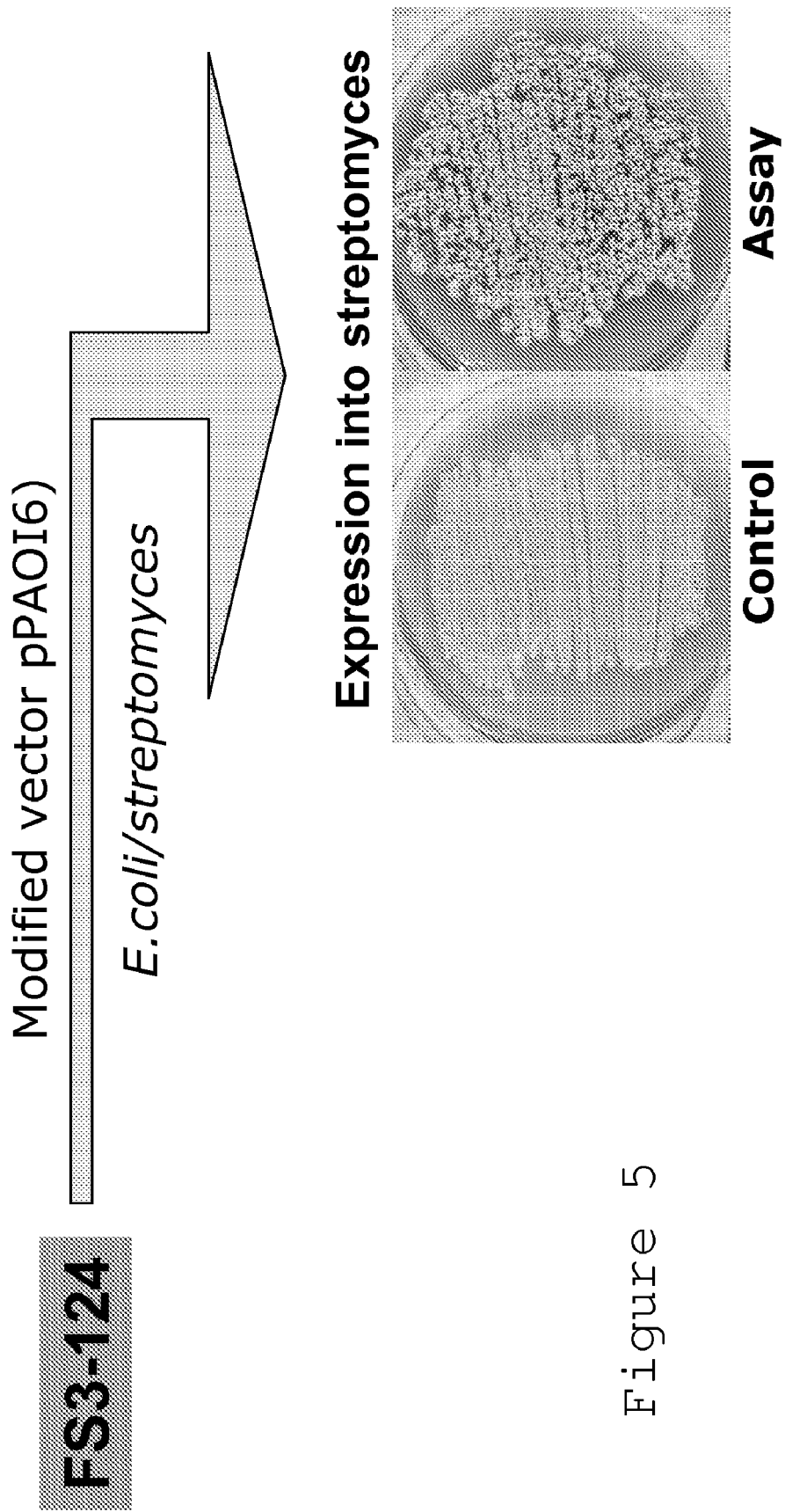

FIG. 5: Morphological differences between Streptomyces transconjugant (assay). Conjugations have been performed with FS3-124 modified with transposable construct pPAOI6; (control) conjugation have been performed with pPAOI6.

Figure 6:
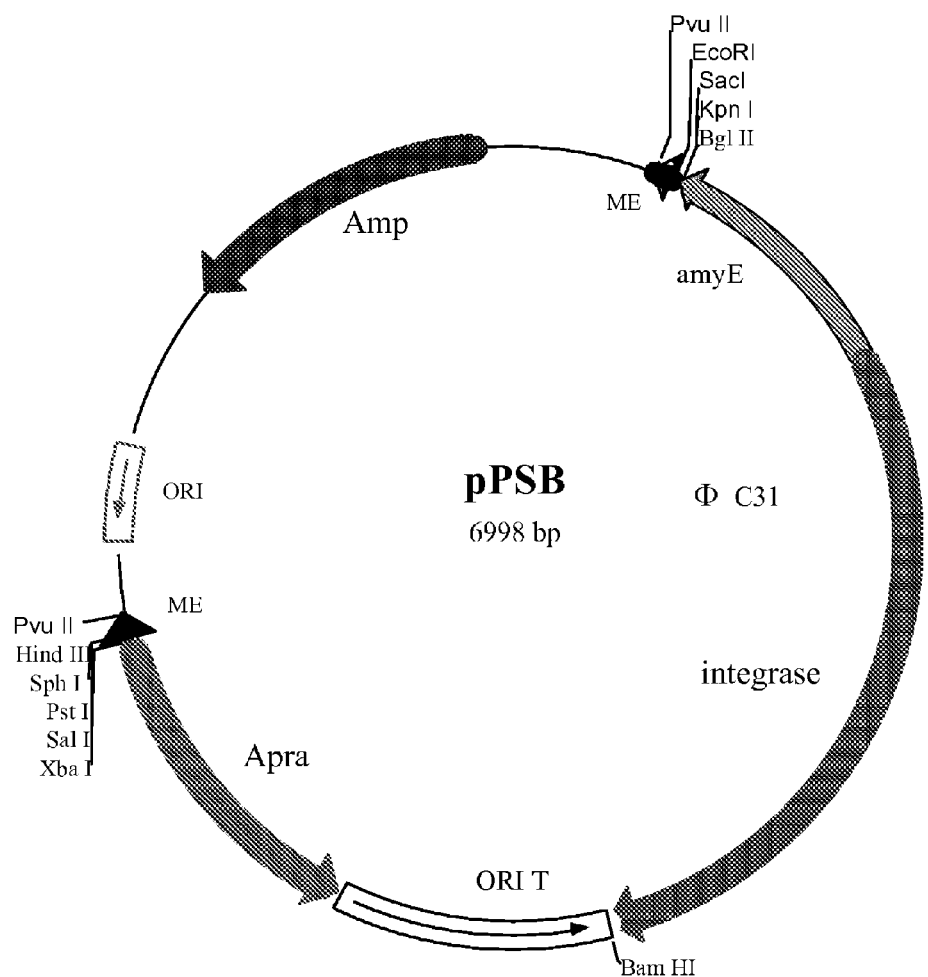
Figure 6:
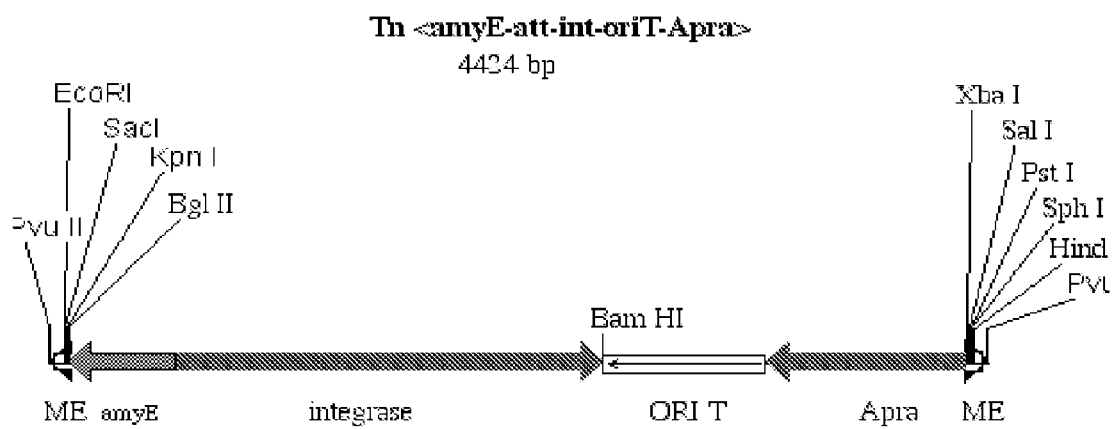

FIG. 6: Schematic Map of pPSB vector (top) and transposable elements (bottom). The transposable element has 720 bp DNA of the amyE gene from B. subtilis in addition to att-int-oriT-Apra.

Figure 7:
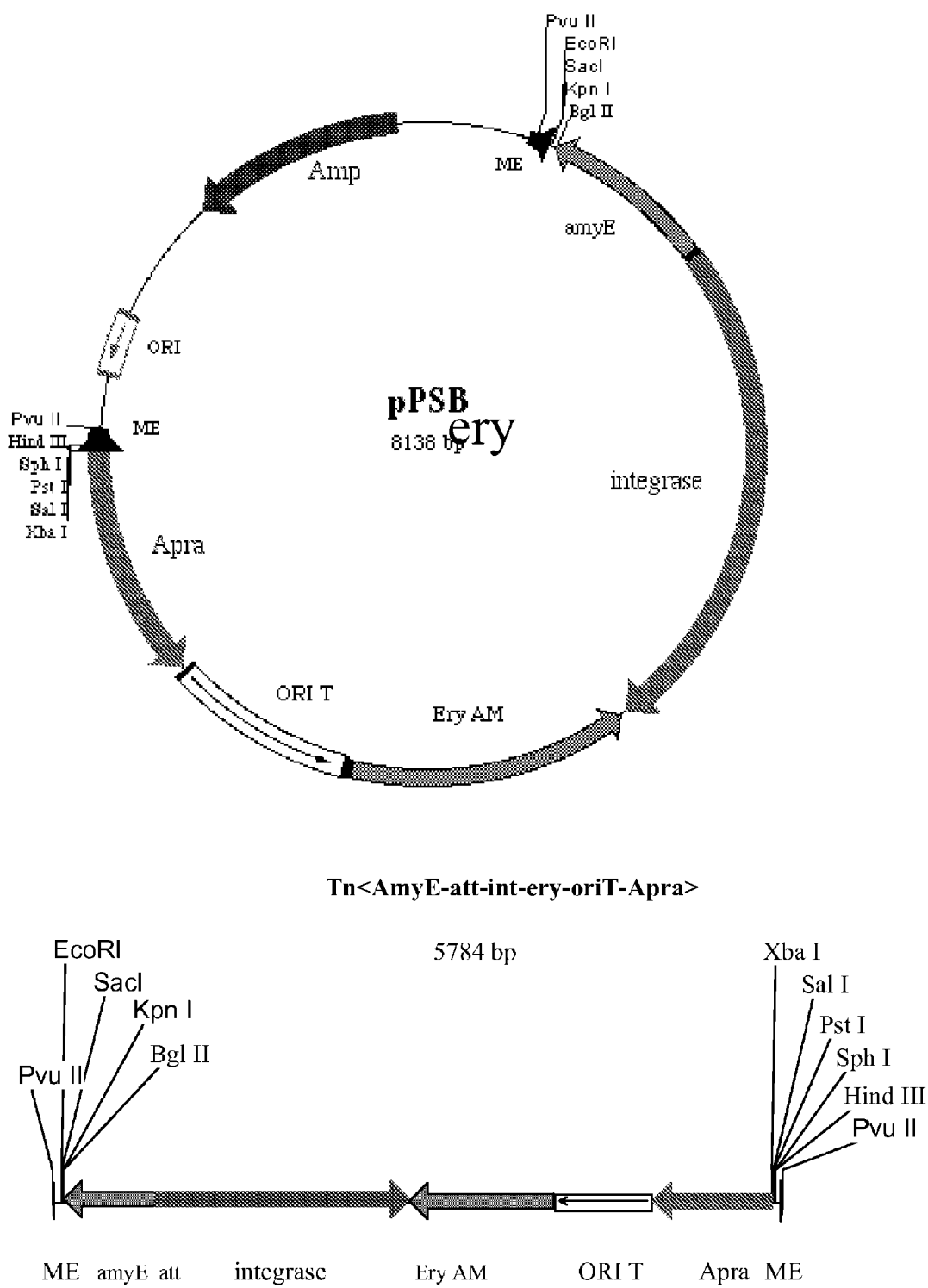

FIG. 7: Plasmid pPSBery (top) and transposable element (bottom) carrying selective marker ery AM, for resistance to erithromycine, and part of amy E gene for homologus recombination in B. subtillis.

Figure 8:
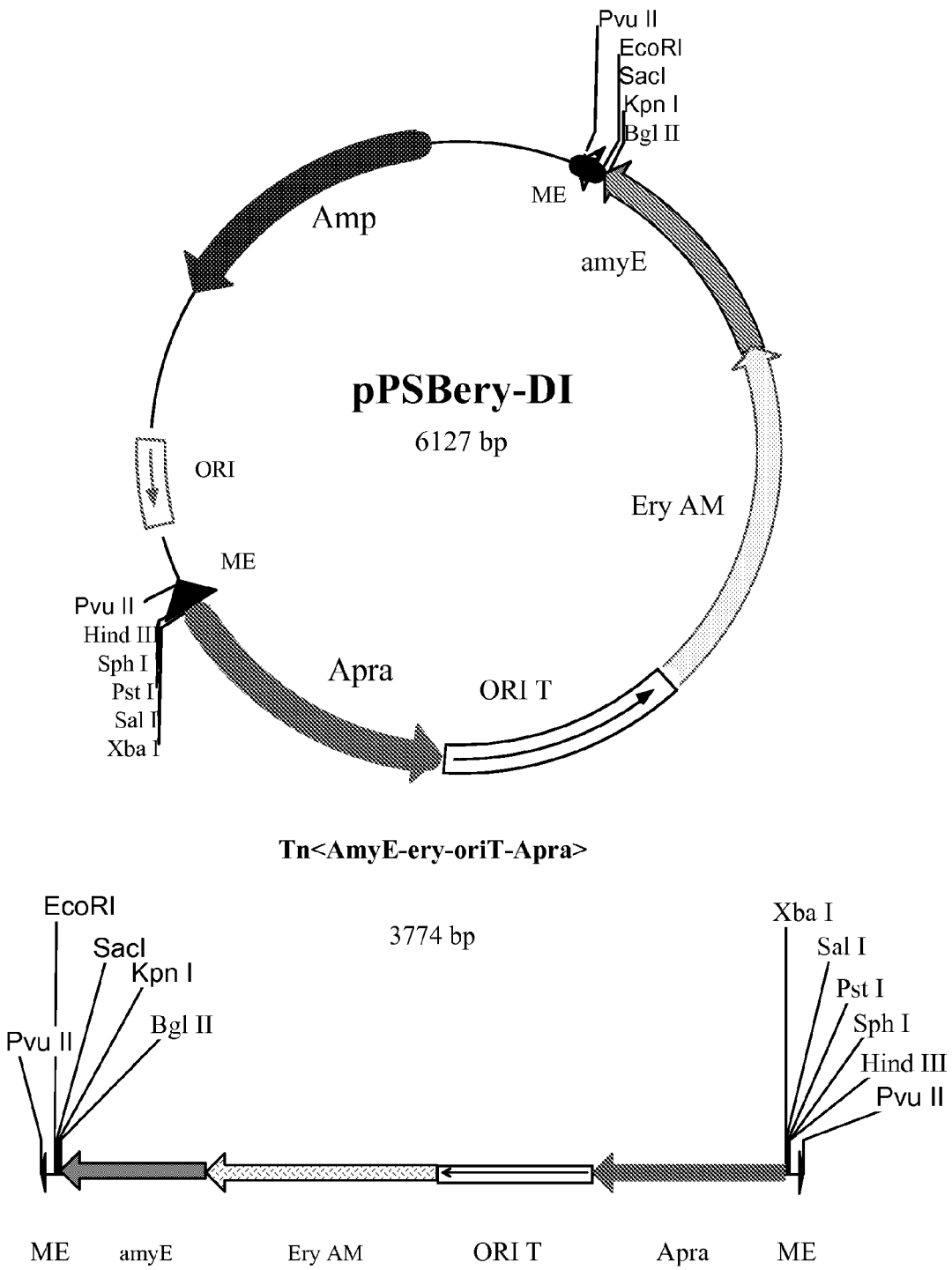

FIG. 8: Integrase ΦC31 was deleted from pPSBery plasmid. Resulting plasmid is pPSBery-DI (top). Transposable element contains Apra and ery AM genes for selection, oriT origin of transfer and a part of amyE gene for integration in to amyE locus of B. subtilis chromosome (bottom).

Figure 9:
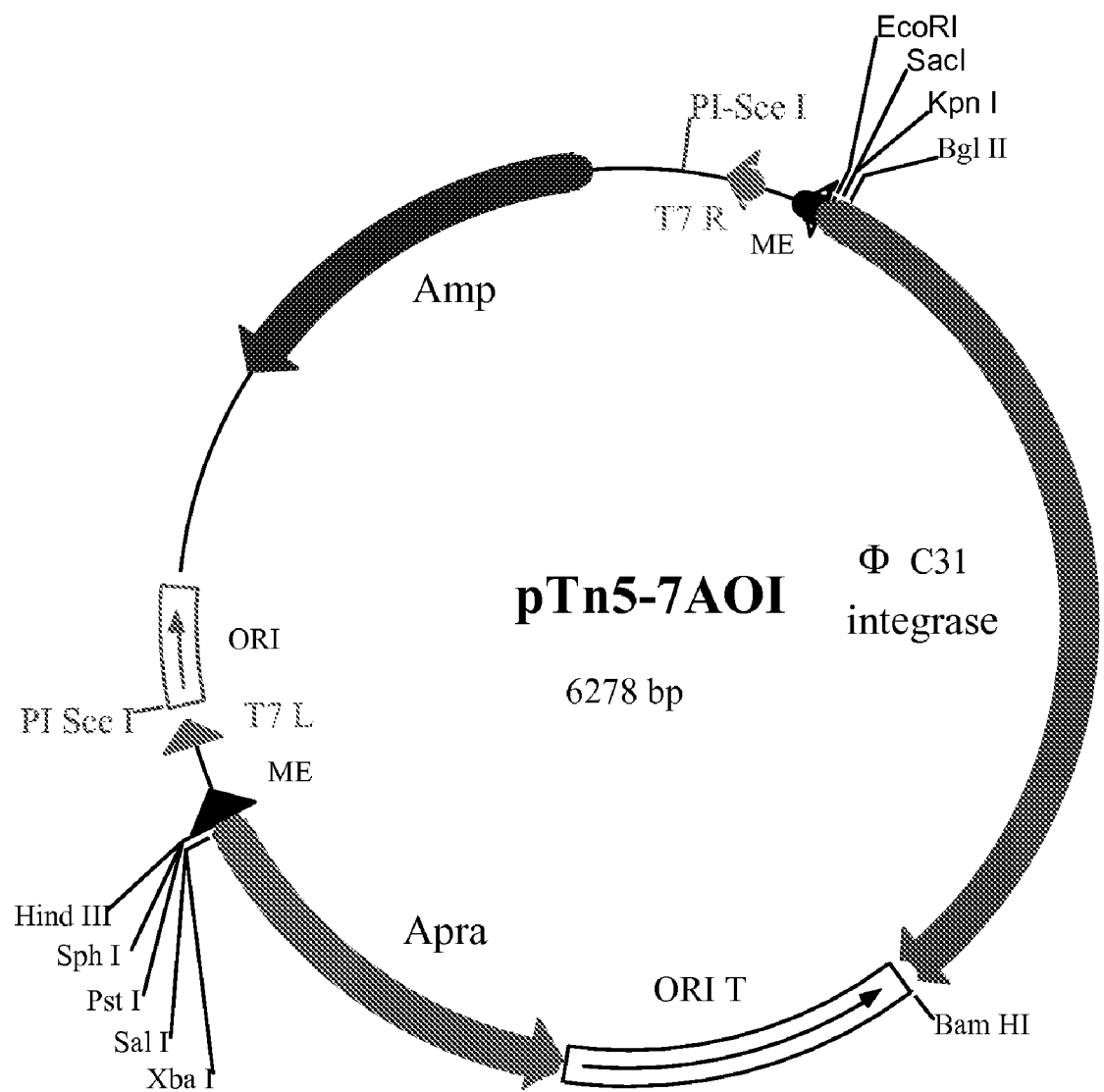

FIG. 9: Map of pTn5-7 AOI plasmid. Transposable element has ends of tn5 (ME) and tn7 (T7 R, T7 L) transposons.

DETAILED DESCRIPTION OF THE INVENTION

The invention provides novel strategies, methods and products for generating and analysing combinatorial gene libraries. As indicated above, the invention discloses, particularly, methods of analysing libraries of polynucleotides, said polynucleotides being contained in cloning vectors having a particular host range, the methods comprising (i) selecting cloning vectors in the library which contain a polynucleotide having a particular characteristic, (ii) modifying said selected cloning vectors to allow a transfer of said vectors and/or expression of the polynucleotide which they contain into a selected host cell, and (iii) analysing the polynucleotides contained in said modified vectors upon transfer of said modified vectors into said selected host cell, such as by genetic, biochemical, chemical or phenotypical approaches.

In a most preferred embodiment, the methods allow stable transfer and propagation of large environmental nucleic acids in a selected host following initial selection. Such methods comprise (i) selecting cloning vectors in a library which contain a polynucleotide having a particular characteristic, (ii) modifying said selected cloning vectors to allow a transfer of said vectors and integration of the polynucleotide which they contain into a selected host cell genome, and (iii) analysing the polynucleotides contained in said modified vectors upon transfer of said modified vectors into said selected host cell, such as by genetic, biochemical, chemical or phenotypical approaches.

Library of Polynucleotides

The term "library of polynucleotides" designates a complex composition comprising a plurality of polynucleotides, of various origins and structure. Typically, the library comprises a plurality of unknown polynucleotides, i.e., of polynucleotides whose sequence and/or source and/or activity is not known or characterized. In addition to such unknown (or uncharacterized) polynucleotides, the library may further include known sequences or polynucleotides. Typically, the library comprises more than 20 distinct polynucleotides, more preferably at least 50, typically at least 100, 500 or 1000. The complexity of the libraries may vary. In particular, libraries may contain more than 5000, 10 000 or 100 000 polynucleotides, of various origin, source, size, etc. Furthermore, the polynucleotides are generally cloned into cloning vectors, allowing their maintenance and propagation in suitable host cells, typically in $E.$ $coli$. The polynucleotides in the library may be in the form of a mixture or separated from each other, in all or in part. It should be understood that some or each polynucleotide in the library may be present in various copy numbers.

The polynucleotides in the libraries are more preferably obtained or cloned from complex sources of nucleic acids, most preferably from environmental samples. Such libraries are also termed "metagenomic libraries" since they contain nucleic acids derived from whole genomes of mixed populations of microorganisms.

The term environmental sample designates, broadly, any sample containing (a plurality of) uncharacterized (micro) organisms, particularly uncultivated (or non-cultivable) microorganisms. The sample may be obtained or derived from specific organisms, natural environments or from artificial or specifically created environments (e.g., industrial effluents, etc). An uncultivated (or non-cultivable) microorganism is a microorganism that has not been purposely cultured and expanded in isolated form. The sample may be obtained or derived from soil, water, mud, vegetal extract, wood, biological material, marine or estuarine sediment, industrial effluents, gas, mineral extracts, sand, natural excrements, meteorits etc. The sample may be collected from various regions or conditions, such as tropical regions, deserts, volcanic regions, forests, farms, industrial areas, household, etc.

Environmental samples usually contain various species of (uncharacterized, uncultivated) microorganisms, such as terrestrial microorganisms, marine microorganisms, salt water microorganisms, freshwater microorganisms, etc. Species of such environmental microorganisms include autotrophe or heterotrophe organisms, eubacteria, archaebacteria, algae, protozoa, fungi, viruses, phages, parasites, etc. The microorganisms may include extremophile organisms, such as thermophiles, psychrophiles, psychrotophes, acidophiles, halophiles, etc. More specific examples of environmental bacteria includes actinomycetes, eubacteriaes and mycobacteriaes, examples of fungi include phycomycetes, ascomycetes and basidiomycetes, etc. Other organisms include yeasts ($saccharomyces$, $kluyveromyces$, etc.) plant cells (algae, lichens, etc), corals, etc. for instance. The sample may comprise various species of such donor (uncultivated) microorganisms, as well as various amounts thereof. The environmental sample may contain, in addition, known and/or cultivable microorganisms (e.g., prokaryotic or eukaryotic), as well as nucleic acids and organic materials. The sample may also contain different animal cells: mammalian cells; insect cells, etc (arising from larvae, feces, etc.).

It should be understood that the present invention is not limited to any specific type of sample or environmental microorganism, but can be used to produce diversity, create nucleic acid libraries, etc., from any environmental sample comprising uncultivated microorganisms. The sample may be wet, soluble, dry, in the form of a suspension, paste, powder, solid, etc. Preferably, the sample is dry or in solid or semisolid state (e.g., paste, powder, mud, gel, etc.). The sample may be treated prior to nucleic acid extraction, for instance by washings, filtrating, centrifuging, diluting, drying, etc.

The term "environmental DNA" designates any DNA fragment or collection obtained from an environmental sample. Nucleic acids may be extracted/isolated from the sample according to various techniques, such as those described in WO01/81357, in WO01/40497, in Handelsman et al. (Chemistry & Biology 5(10), 1998, R245), Rondon et al. (Tibtech 17, 1999, 403; Applied and Environm. Microbiol. 66, 2000, 2541), Miller et al (Applied and Environm. Microbiol. 65, 1999, 4715) or Frostegard et al. (Applied and Environm. Microbiol., 65, 1999, 5409).

In a particular embodiment of the above method, the library comprises a plurality of environmental DNA fragments. The library may also comprise other types of nucleic acids, such as environmental RNAs, for instance.

The polynucleotides have a size which is typically comprised between 10 and 100 kb, more preferably between 20 and 80 kb, typically between 30 and 80 kb. Although not mandatory, it is preferred that the polynucleotide fragments in the library all have similar size, to produce homogenous libraries.

Cloning Vectors

As indicated, the polynucleotides are contained or cloned into cloning vectors. These vectors may be of various types, including plasmids, cosmids, fosmids, episomes, artificial chromosomes, phages, viral vectors, etc. In most preferred embodiments, the cloning vectors are selected from plasmids, cosmids, phages (e.g., P1-derivatives) and BACs, even more preferably from cosmids, P1 derivatives and BACs. By using cosmids or P1 derivatives, it is possible to generate homogenous libraries, since these vectors essentially accommodate polynucleotides having a size of approximately 40 kb and 80 Kb, respectively. Furthermore, since the invention provides that the vectors are modified after the initial cloning step, the cloning capacity of the vectors is maximized and inserts of as much as 40 and 80 kbs in length can be cloned into fosmids, BAC and P1 derivatives.

As indicated the cloning vector has a particular host range, i.e., the ability to replicate in a particular type of host cell. Typically, the host is a bacteria, more preferably an $E.$ $coli$ strain. Indeed, $E.$ $coli$ is so far the most convenient host cell for performing recombinant technologies. The advantage of the present invention is that the starting library can be produced in any suitable host system of choice, since the properties of the libraries will be adapted later during the process.

Cloning vectors generally comprise the polynucleotide insert and genetic elements necessary and sufficient for maintenance into a competent host cell. They typically contain, in addition to the polynucleotide insert, an origin of replication functional in a selected host cell as well as a marker gene for selection and screening. The cloning vector may comprise additional elements, such as promoter regions, for instance. Although cloning vectors may replicate in several different host cells, they are usually adapted to a particular host cell type and not suitable or efficient for replication or maintenance in other cell types.

In a preferred embodiment, the cloning vectors of the library are $E.$ $coli$ cloning vectors, preferably cosmids, BAC or P1 derived vectors. *E. coli* cloning vectors may carry an origin of replication derived from naturally-occurring plasmids, such as ColE1, pACYC and p15A, for instance. Many *E. coli* cloning vectors are commercially available and/or can be constructed using available regulatory sequences.

Screening of the Cloning Vectors

In step i) of the method, a first selection or screen is performed on the polynucleotide library. The screen is performed so as to identify or select clones having (or lacking) a particular, common characteristic. The selection may be carried out according to various techniques, such as molecular screening, protein expression, functional screening, etc. A preferred selection is performed by molecular screening. Molecular screening designates any method of identification of molecular or structural characteristics in a polynucleotide sequence. This can be made by a variety of techniques which are known per se, such as hybridisation, amplification, sequencing, etc. Preferably, molecular screening comprises the selection of clones in a library which contain, in their sequence, a particular sequence or region or motif, said sequence or region or motif being characteristic of a particular type of activity or gene (enzyme, biosynthetic pathways, etc.).

In a first variant, the selection is made by contacting the cloning vectors in the library with a particular nucleic acid probe (or set of probes) containing a sequence which is characteristic of a selected activity or function (a consensus sequence, a particular motif, etc.). The cloning vectors in the library which hybridise to the probe (or set of probes) are then selected.

In a second variant, the selection is made by contacting the cloning vectors in the library with a particular pair of nucleic acid primers specific for a sequence which is characteristic of a selected activity or function (a consensus sequence, a particular motif, etc.), and a PCR amplification reaction is performed. The cloning vectors in the library which lead to a positive amplification product are then selected.

In this regard, the present application provides new primers designed in conserved motives of the β-keto acyl synthase gene, which are particularly useful for screening polynucleotides containing putative polyketide synthase (PKS) genes or domains. These primers have the following degenerated sequence:

```
Sense primer:
5'- GGSCCSKCSSTSDCSRTSGAYACSGC -3'   (SEQ ID NO: 3)

Antisense primer:
5'- GCBBSSRYYTCDATSGGRTCSCC -3'      (SEQ ID NO: 4)
``` wherein:
R is A or G
S is G or C
Y is C or T
K is G or T
D is A or G or T, and
B is C or G or T.

A particular object of this invention is a polynucleotide primer having one of the above sequences, typically a mixture of different polynucleotide primers having a sequence corresponding to one of the above degenerated sequences. A particular object of this invention also resides in a pair of primers each having one of the above sequences.

Once particular clones have been selected, the analysis of their polynucleotides needs to be confirmed and/or validated, and/or their polynucleotides can be used to study their function and/or produce novel compounds or metabolites.

The invention now enables such further analysis and uses, by allowing a modification of the cloning vectors that is specific and adaptable by the skilled person, depending on the activity which is sought. In particular, it is possible to confer properties such as specific expression or a novel, specific host range to the selected cloning vectors, to assess their activity, as disclosed below.

Modification of the Cloning Vectors

After high efficiency cloning using most convenient cloning vectors such as BACs or cosmids propagated into *E. coli*, and after the identification, selection and/or characterisation of cloned DNA fragments, the invention now allows to modify specifically the cloning vectors to transfer, integrate into the genome, maintain, express and/or over-express the selected polynucleotides into any selected host expression system, which is suitable to assess the selected activity or property. Such selected hosts may be native or heterologous host cells, and include, but are not limited to, for example *Streptomyces, Nocardia, Bacillus*, fungi, yeasts, etc.

The selected cloning vectors of the library may be modified according to various techniques. The modification is typically a genetic modification, comprising the introduction of particular genetic sequences into the structure of the cloning vector, in addition to or in replacement of sequences contained in said vector. It is highly preferred to use specific or targeted (or oriented) techniques to improve the efficacy of the method. By "specific" is meant that the modification occurs at a pre-determined location in the cloning vector, through site-specific mechanisms. By "targeted" is meant that the modification occurs in a controlled way, so as not to alter the polynucleotide insert contained in the vector in a non-desirable way.

In a preferred embodiment, the selected vectors are modified by insertion, into the vector, of a target polynucleotide construct which contains genetic elements conferring the selected property(ies) to the cloning vector.

The target polynucleotide construct typically comprises the genetic elements necessary to transfer, propagate, integrate into the genome, maintain, express or overexpress the cloned polynucleotide into a chosen (bacterial) host expression system. Said genetic elements may include particular origin(s) of replication, particular origin(s) of transfer, particular integrase(s), transcriptional promoter(s) or silencer(s), either alone or in combination(s).

In a first, preferred variant, the target polynucleotide construct comprises a genetic element allowing transfer of the vector into a selected host cell.

Natural DNA transfer mechanisms between donor and recipient strains is known under the term conjugation or conjugative transfer. Conjugative transfer can occur between different strains of the same species as well as between strains of different species. Many naturally occurring plasmids carry so called tra genes, which are involved in and mediate conjugative transfer. The DNA transfer starts at specific DNA structures, known as an origin of transfer or "ori T". The presence of such an oriT in a vector allows said vector to be transferred into a desired host cell.

In a particular, preferred embodiment, the target polynucleotide construct comprises an origin of transfer functional in the selected host cell.

The structure of various oriT has been reported in the art (Guiney et al. 1983; Zechner et al. 2000). In a specific embodiment, the origin of transfer is selected (or derived) from RP4, pTiC58, F, RSF1010, ColE1 and R6K(α).

A specific example of an oriT which can be used in the present invention derives from plasmid RP4 and has or comprises all or a functional part of the following sequence (SEQ ID NO: 5):

```
gatctGTGATGTACTTCACCAGCTCCGCGAAGTCGCTCTTCTTGATTGGAGCGCATGGG

GACGTGCTTGGCAATCACGCGCACCCCCCGGCCGTTTTAGCGGCTAAAAAAGTCAT

GGCTCTGCCCTCGGGCGGACCACGCCCATCATGACCTTGCCAAGCTCGTCCTGCTTC

TCTTCGATCTTCGCCAGCAGGGCGAGGATCGTGGCATCACCGAACCGCGCCGTGCG

CGGGTCGTCGGTGAGCCAGAGTTTCAGCAGGCCGCCCAGGCGGCCCAGGTCGCCAT

TGATGCGGGCCAGCTCGCGGACGTGCTCATAGTCCACGACGCCCGTGATTTTGTAGC

CCTGGCCGACGGCCAGCAGGTAGGCCGACAGGCTCATGCCGGCCGCCGCCGCCTTT

TCCTCAATCGCTCTTCGTTCGTCTGGAAGGCAGTACACCTTGATAGGTGGGCTGCCC

TTCCTGGTTGGCTTGGTTTCATCAGCCATCCGCTTGCCCTCATCTGTTACGCCGGCGG

TAGCCGGCCAGCCTCGCAGAGCAGGATTCCCGTTGAGCACCGCCAGGTGCGAATAA

GGGACAGTGAAGAAGGAACACCCGCTCGCGGGTGGGCCTACTTCACCTATCCTGCC

CGGCTGACGCCGTTGGATACACCAAGGAAAGTCTACACGAACCCTTTGGCAAAATC

CTGTATATCGTGCGAAAAAGGATGGATATACCGAAAAAATCGCTATAATGACCCCG

AAGCAGGGTTATGCAGCGGAAAAGATCCGTCGGATCT
```

The term "functional part" designates any fragment or variants of the above sequence which retain the capacity to cause conjugative transfer. Such fragments typically comprise at least 80%, preferably at least 85% or 90% of the above sequence. Variants may include one or several mutations, substitutions, deletions or additions of one or several bases.

In an other particular variant, the target polynucleotide construct comprises a genetic element allowing integration of the vector (or of the polynucleotide contained therein) into the genome of the selected host cell.

A donor DNA is permanently or stably maintained and expressed in a selected recipient cell if it is integrated into the recipient cell's genome or if it contains elements that allow autonomous replication in said cell. In a most preferred embodiment, the vector is modified to allow transfer and integration of the polynucleotide into the host cell genome.

Integration is a preferred way of ensuring stable expression. Integration can be obtained by physical recombination. Recombination can be homologous, e.g., between two homologous DNA sequences, or illegitimate, where recombination occurs between two non-homologous DNAs. As a particular example, integration of donor DNA into the chromosome of the recipient can be mediated by host recombination repair system or by site-specific recombination. Another well-studied process that can transfer and integrate genes is transduction by bacterial viruses, such as λ and φC31. In a phage-infected bacterial cell, fragments of the host DNA are occasionally packaged into phage particles and can then be transferred to a recipient cell. Integration into the recipient cell's genome is caused by an integrase.

In a specific embodiment, the target polynucleotide construct comprises a nucleic acid encoding an integrase functional in the selected host cell. More preferably, the integrase is selected from λ and φC31 integrases. In a specific embodiment, the polynucleotide construct comprises a nucleic acid encoding an integrase having or comprising all or a functional part of the following sequence of the φC31 integrase (SEQ ID NO: 6):

```
AGATCTCCCGTACTGACGGACACACCGAAGCCCCGGCGGCAACCCTCAGCGGATGC

CCCGGGGCTTCACGTTTTCCCAGGTCAGAAGCGGTTTTCGGGAGTAGTGCCCCAACT

GGGGTAACCTTTGAGTTCTCTCAGTTGGGGGCGTAGGGTCGCCGACATGACACAAG

GGGTTGTGACCGGGGTGGACACGTACGCGGGTGCTTACGACCGTCAGTCGCGCGAG

CGCGAGAATTCGAGCGCAGCAAGCCCAGCGACACAGCGTAGCGCCAACGAAGACA

AGGCGGCCGACCTTCAGCGCGAAGTCGAGCGCGACGGGGGCCGGTTCAGGTTCGTC

GGGCATTTCAGCGAAGCGCCGGGCACGTCGGCGTTCGGGACGGCGGAGCGCCCGGA

GTTCGAACGCATCCTGAACGAATGCCGCGCCGGGCGGCTCAACATGATCATTGTCT

ATGACGTGTCGCGCTTCTCGCGCCTGAAGGTCATGGACGCGATTCCGATTGTCTCGG

AATTGCTCGCCCTGGGCGTGACGATTGTTTCCACTCAGGAAGGCGTCTTCCGGCAGG

GAAACGTCATGGACCTGATTCACCTGATTATGCGGCTCGACGCGTCGCACAAAGAA

TCTTCGCTGAAGTCGGCGAAGATTCTCGACACGAAGAACCTTCAGCGCGAATTGGG

CGGGTACGTCGGCGGGAAGGCGCCTTACGGCTTCGAGCTTGTTTCGGAGACGAAGG
```

-continued
```
AGATCACGCGCAACGGCCGAATGGTCAATGTCGTCATCAACAAGCTTGCGCACTCG

ACCACTCCCCTTACCGGACCCTTCGAGTTCGAGCCCGACGTAATCCGGTGGTGGTGG

CGTGAGATCAAGACGCACAAACACCTTCCCTTCAAGCCGGGCAGTCAAGCCGCCAT

TCACCCGGGCAGCATCACGGGGCTTTGTAAGCGCATGGACGCTGACGCCGTGCCGA

CCCGGGGCGAGACGATTGGGAAGAAGACCGCTTCAAGCGCCTGGGACCCGGCAACC

GTTATGCGAATCCTTCGGGACCCGCGTATTGCGGGCTTCGCCGCTGAGGTGATCTAC

AAGAAGAAGCCGGACGGCACGCCGACCACGAAGATTGAGGGTTACCGCATTCAGCG

CGACCCGATCACGCTCCGGCCGGTCGAGCTTGATTGCGGACCGATCATCGAGCCCG

CTGAGTGGTATGAGCTTCAGGCGTGGTTGGACGGCAGGGGCGCGGCAAGGGGCTT

TCCCGGGGGCAAGCCATTCTGTCCGCCATGGACAAGCTGTACTGCGAGTGTGGCGC

CGTCATGACTTCGAAGCGCGGGGAAGAATCGATCAAGGACTCTTACCGCTGCCGTC

GCCGGAAGGTGGTCGACCCGTCCGCACCTGGGCAGCACGAAGGCACGTGCAACGTC

AGCATGGCGGCACTCGACAAGTTCGTTGCGGAACGCATCTTCAACAAGATCAGGCA

CGCCGAAGGCGACGAAGAGACGTTGGCGCTTCTGTGGGAAGCCGCCCGACGCTTCG

GCAAGCTCACTGAGGCGCCTGAGAAGAGCGGCGAACGGGCGAACCTTGTTGCGGAG

CGCGCCGACGCCCTGAACGCCCTTGAAGAGCTGTACGAAGACCGCGCGGCAGGCGC

GTACGACGGACCCGTTGGCAGGAAGCACTTCCGGAAGCAACAGGCAGCGCTGACGC

TCCGGCAGCAAGGGGCGGAAGAGCGGCTTGCCGAACTTGAAGCCGCCGAAGCCCCG

AAGCTTCCCCTTGACCAATGGTTCCCCGAAGACGCCGACGCTGACCCGACCGGCCCT

AAGTCGTGGTGGGGGCGCGCGTCAGTAGACGACAAGCGCGTGTTCGTCGGGCTCTT

CGTAGACAAGATCGTTGTCACGAAGTCGACTACGGGCAGGGGGCAGGGAACGCCCA

TCGAGAAGCGCGCTTCGATCACGTGGGCGAAGCCGCCGACCGACGACGACGAAGAC

GACGCCCAGGACGGCACGGAAGACGTAGCGGCGTAGCGAGACACCCG
```

The term "functional part" designates any fragment or variants of the above sequence which retain the capacity to cause integration. Such fragments typically comprise at least 80%, preferably at least 85% or 90% of the above sequence. Variants may include one or several mutations, substitutions, deletions or additions of one or several bases.

In a more preferred variant, the target polynucleotide construct comprises genetic elements allowing transfer of the cloning vector into the selected host cell and integration of the cloning vector or a portion thereof into the genome of the selected host cell. Most preferred polynucleotide constructs comprises an oriT and a nucleic acid encoding an integrase.

In an other variant, the target polynucleotide construct comprises an origin of replication specific for or functional in the selected host cell. The origin of replication may be selected (or derived), for instance, from pAMβ1, pSa, 2 μm circle, pSam2, pSG1, pIJ101, SCP2, pA387 and artificial chromosomes.

In an other variant, the target polynucleotide construct comprises a transcriptional promoter functional in the selected host cell. As indicated above, in a particular variant, the invention allows to modify the cloning vector to enable expression or over-expression of the cloned polynucleotides in the selected host. The expression of genes is driven mainly by transcriptional promoters, which initiate gene transcription. The type of promoter to be used in the present invention can be selected by the skilled person, depending on the selected host cell and type of expression needed. Promoters may be ubiquitous or cell-specific, regulated or constitutive, weak or strong. They may be of various origins, including promoters isolated from viruses, phages, plant cells, bacterial genes, mammalian genes, etc., or they may be artificial or chimeric. Typical examples of promoters include T7, T4, LacZ, trp, ara, SV40, tac, λPL, GAL, AOX, hsp-70, etc.

The target polynucleotide construct is typically a DNA molecule, although RNAs may also be used as starting material. It is typically a double-stranded DNA. The target polynucleotide construct may be produced by conventional recombinant DNA techniques, including DNA synthesis, cloning, ligation, restriction digestion, etc. and a combination thereof.

The target polynucleotide construct is preferably engineered so as to be inserted in a region of the vector distinct from the polynucleotide. Indeed, it is important that the integrity of the polynucleotides is preserved. Directed insertion may be accomplished in a variety of ways, including site-specific insertion using particular enzymatic systems (Cre/Lox, FLP, etc.), homologous recombination with particular target sequences present in the vector, or by the use of transposons or transposable elements and appropriate selection means.

In a particular, preferred embodiment, the target polynucleotide construct is contained in or comprises a transposable nucleic acid construct. Indeed, in a preferred variant, the methods of the present invention use transposable elements to alter the properties of the cloning vectors, and allow their transfer, maintenance, expression or over-expression in a selected host cell.

Transposable nucleic acid constructs are derived from transposons, which are genetic elements capable of moving from one genetic loci to another. Two main classes of transposons have been identified in bacteria. The most simple transposons comprise an insertion sequence that carries only elements of transposition. These elements are two inverted DNA repeats and a gene that codes for a protein called transposase. The transposase catalyses the excision and integration of the transposon. It has been shown that the excision and integration reaction can be catalysed in trans by a transposase, which can be provided in vivo or in vitro in purified form or expressed from a different construct. More complex transposons carry more insertion sequences and additional genes that are not involved in transposition.

Transposable nucleic acid constructs of this invention thus typically comprise, flanked by two inverted repeats, the target polynucleotide construct and, more preferably, a marker gene. In the presence of a transposase, these transposable nucleic acid constructs can integrate into a cloning vector in vivo or in vitro, thereby providing for targeted polynucleotide insertion. Alternatively, such nucleic acid constructs can be used for targeted integration, in the absence of a transposase, in particular strains such as hypermutator strains. Such transposable nucleic acid constructs also represent a particular object of the present application. In this regard, in a more preferred embodiment, the invention also relates to a transposable nucleic acid construct, wherein said construct comprises an origin of transfer flanked by two inverted repeats. Specific examples of such construct are transposons pPL1 and pPAOI6, as disclosed in the experimental section. The transposable nucleic acid construct may further comprise an integrase gene and/or a marker gene.

The inverted repeat nucleic acid sequences may be derived from the sequence of various transposons, or artificially created. In particular, transposable elements can be generated using inverted repeats obtained from transposons or transposable elements such as Tn5, Tn21, miniTn5, T7, T10, Tn917, miniTn400, etc. Preferably, the sequences derive from transposon Tn5. In a specific embodiment, they comprise all or a functional part of the following sequences:

```
left arm of pPAOI6 transposon (SEQ ID NO: 7)
CTGTCTCTTATACACATCTCAACCATCATCGATGAATTTTCTCGGGTGTTCTCGCATA

TTGGCTCGAATTCGAGCTCGGTACCC right arm of transposon pPAOI6 (SEQ ID NO: 8)
GATCCTCTAGAGTCGACCTGCAGGCATGCAAGCTTGCCAACGACTACGCACTAGCC

AACAAGAGCTTCAGGGTTGAGATGTGTATAAGAGACAG
```

The marker gene may be any nucleic acid encoding a molecule whose presence in a cell can be detected or visualized. Typical marker genes encode proteins conferring resistance to antibiotics, such as apramycine, chloramphenicol, ampiciline, kanamycine, spectinomycine, thiostrepton, etc.

Other types of markers confer auxotrophy or produce a label (e.g., galactosidase, GFP, luciferase, etc).

In a specific embodiment, the cloning vector in the library comprises a first marker gene and the modification step ii) comprises:

contacting in vitro, in the presence of a transposase, the selected cloning vectors with a transposon comprising, flanked by two inverted repeats, the target polynucleotide construct and a second marker gene distinct from the first marker gene, and selecting the cloning vectors which have acquired the second marker gene and which have lost the first marker gene.

The double selection ensures that the target polynucleotide construct has been inserted at a site within the marker gene present in the cloning vector, i.e., outside of the polynucleotide insert.

It should be understood that the modification may be accomplished in various other ways, particularly by incorporating a sequence coding for the transposase directly into the transposable element or into another expression unit. The presence and expression of the transposase can be regulated by inductive promoter or termosensitive replicative units. Also, transposition can be carried out by in vitro process.

Analysis of the Polynucleotides

In step (iii) of the process, the polynucleotides may be analysed by various methods, including by genetic, biochemical, chemical or phenotypical approaches, which are well known per se in the art. Analysis occurs upon transfer and, optionally, expression of the polynucleotides into the selected host cell.

In this regard, the modified cloning vectors can be transferred into the selected host cell by a variety of techniques known in the art, including by transformation, electroporation, transfection, protoplast fusion, conjugative transfer, etc. In a preferred embodiment, the target polynucleotide construct comprises an oriT and the modified vectors are transferred into the selected host cells by conjugative transfer. In this embodiment, the cloning vector and the selected host cells are co-cultivated and the recombinant host cells are selected and isolated.

The selected host cell may be any type of cell or microorganism, including, without limitation, Steptomyces, E. coli, Salmonella, Bacillus, Yeast, fungi, etc.

One of the objectives of the invention is to be able to analyse environmental DNAs of unknown cellular origin into different host expression systems. In order to analyse the potentiality of the DNAs at the transcription and/or translation levels and to have much more probabilities to have a DNA expression, it is important to have the possibility to test different host expression systems.

Insertion of foreign DNA into host expression systems like *Streptomyces* can produce, for instance, an increase in doubling time, morphological modifications, pigments production, etc., which can be related either directly to the expression of foreign DNA or by combinatorial biology of the foreign DNA and the biology of the expression host systems. The new phenotypes can be analysed by all techniques known in the art such genetic, biochemical, chemical, phenotypic approaches etc.

In a preferred, specific embodiment, the invention relates to a method for the identification or cloning of polynucleotides encoding a selected phenotype, the method comprising (i) cloning environmental DNA fragments into *E. coli* cloning vectors to produce a metagenomic library, (ii) identifying or selecting cloning vectors in said library which contain DNA fragments having a particular characteristic of interest, (iii) modifying the identified or selected cloning vectors into shuttle or expression vectors for transfer and integration in a selected host cell, (iv) transferring the modified cloning vectors into said selected host cell and (v) identifying or cloning the DNA fragments contained in said modified cloning vectors which encode said selected phenotype in said selected host cell.

By applying the above method, new polynucleotide sequences have been identified, cloned and characterized, which produce new phenotypes in bacteria. These polynucleotides contain the sequence of PKS genes and other genes that encode polypeptides involved in biosynthetic pathways. The sequence of these polynucleotides is provided in SEQ ID NO:1 and SEQ ID NO:2.

The complete annotated DNA sequences of fosmid clones FS3-124 and FS3-135 are provided in SEQ ID NOs: 1 and 2, respectively, and as further described in the following CDS information.

Specifically, the following CDS information are related to SEQ ID NO:1.

| CDS | 76..1134 |
| --- | --- |
| | /note="ABC_transportr" |
| | /gene="TAP2 PROTEIN" |
| | /blastp_match="*Oryzias latipes*" |
| | /blast_score= 0.002 |
| CDS | complement(1096..2430) |
| | /note="none" |
| | /blastp_match="*Anabaena* sp" |
| | /gene="ALR1117 PROTEIN" |
| | /blast_score=2e-18 |
| CDS | 1178..1624 |
| | /note="Gram_pos_anchor" |
| | /gene="CELL WALL SURFACE ANCHOR" |
| | /blast_score=1e-04 |
| | /blastp_match="*Streptococcus pneumoniae*" |
| CDS | complement(2506..3567) |
| | /note="CONSERVED" |
| | /gene="HYPOTHETICAL PROTEIN" |
| | /blast_score=0.019 |
| | /blastp_match="*Deinococcus radiodurans*" |
| CDS | complement(2906..4222) |
| | /note="glycosyl transferase" |
| | /gene="lipopolysaccharide" |
| | /blast_score=2e-23 |
| CDS | complement(4092..5321) |
| | /note="glycosyl transferase" |
| | /gene="glycosyl transferase" |
| | /blast_score=1e-15 |
| CDS | complement(6337..8502) |
| | /note="PUTATIVE" |
| | /gene="GLUTAMINE AMIDOTRANSFERASE" |
| | /blastp_match=" *Bordetella bronchiseptica*" |
| | /blast_score=1e-16 |
| CDS | complement(8181..9530) |
| | /note="none" |
| | /gene="MEMBRANE PROTEIN" |
| | /blast_score=0.035 |
| CDS | complement(9531..10721) |
| | /note="NOEC Transmembrane" |
| | /gene="NODULATION PROTEIN" |
| | /blastp_match="*Azorhizobium caulinodans*" |
| | /blast_score=3e-07 |
| CDS | complement(10504..11274) |
| | /note="PUTATIVE" |
| | /gene="HYDROLASE" |
| | /blastp_match="*Streptomyces coelicolor*" |
| | /blast_score=4e-14 |
| CDS | 12874..13689 |
| | /note="HYPOTHETICAL Meth-transf" |
| | /gene="PROTEIN PA1088" |
| | /blast_score=2e-06 |
| | /blastp_match=" *Pseudomonas aeruginosa*" |
| CDS | 14195..15976 |
| | /note="PUTATIVE, Glyco_transf" |
| | /note=" " |
| | /gene="LIPOPOLYSACCHARIDE BIOSYNTHESIS" |
| | /blast_score=2e-06 |
| | /blastp_match="*Vibrio cholerae*" |
| CDS | 15427..16512 |
| | /note="PATHWAY: INNER CORE LIPOPOLYSACCHARIDE BIOSYNTHESIS" |
| | /gene="PHOSPHOHEPTOSE ISOMERASE " |
| | /blast_score=3e-17 |
| | /blastp_match="*Helicobacter pylori*" |
| CDS | 15579..16253 |
| | /note="none" |
| | /gene="PHOSPHOHEPTOSE ISOMERASE" |
| | /blast_score=2e-22 |
| | /blastp_match="*Neisseria meningitidis*" |
| CDS | complement(16505..17656) |
| | /note="BIOSYNTHESIS PUTATIVE" |
| | /gene="LIPOPOLYSACCHARIDE" |
| | /blast_score=2e-17 |
| | /blastp_match="*Thermotoga maritima*" |
| | /pfam_match="Glycos_transf_1" |
| CDS | complement(17657..18697) |
| | /note="none" |
| | /gene="ALR3073 PROTEIN" |
| | /blast_score=6e-27 |
| | /blastp_match="*Anabaena* sp" |
| CDS | complement(18615..19304) |
| | /note="none" |
| | /gene="ALR4487 PROTEIN" |
| | /blast_score=8e-07 |
| | /blastp_match="*Anabaena* sp" |
| CDS | complement(19301..20596) |
| | /note="ATP_GTP_A" |
| | /gene="ABC TRANSPORTER" |
| | /blast_score=3e-61 |
| | /blastp_match="*Synechocystis* sp" |
| CDS | complement(20535..21476) |
| | /note="PERMEASE COMPONENT" |
| | /gene="POLYSACCHARIDE ABC TRANSPORTER" |
| | /blast_score=6e-41 |
| | /blastp_match="*Clostridium acetobutylicum*" |
| CDS | complement(22025..22951) |
| | /note="involved in the synthesis of a polysaccharide capsule ?" |
| | /gene="32.3 KDA PROTEIN" |
| | /blast_score=3e-17 |
| | /blastp_match="*Sphingomonas* sp" |
| CDS | 23155..26523 |
| | /note="peptide syntase" |
| | /gene="mcyA, mcyB and mcyC" |
| | /blastp_match="*Microcystis aeruginosa*" |
| | /blast_score=0.0 |
| CDS | 26409..34433 |
| | /note="polyketide syntase et peptide syntase" |
| | /gene="mcyD, mcyE, mcyF and mcyG" |
| | /blastp_match="*Microcystis aeruginosa*" |

```
CDS     34418..37500
        /note="CYSTATIN"
        /gene="PEPTIDE SYNTHETASE"
        /blast_score=0.0
        /blastp_match="Anabaena sp"
CDS     35359..37500
        /note="gene cluster"
        /gene="nostopeptolide biosynthetic"
        /blast_score=2e-41
        /blastp_match="Nostoc sp"
Sequence 37500 BP; 6199 A; 12698 C; 12769 G; 5834 T; 0 other;
```

The following CDS information are related to SEQ ID NO:2.

```
CDS     complement(3..914)
        /blast_score=2e-66
        /blastp_match="AE004644.PA2177 Pseudomonas aeruginosa"
        /gene="regulator hybrid"
        /note="probable similarity to prokaryote sensory
        transduction proteins"
        /product="sensor/response regulator hybrid"
CDS     924..2168
        /note="none"
        /gene="ligase"
        /blastp_match="AP003013.MLR8297 Mesorhizobium loti"
        /blast_score=e-152
        /product="2-amino-3-ketobutyrate CoA ligase"
CDS     2207..3190
        /blast_score=e-151
        /blastp_match="AE008872.TDH Salmonella typhimurium"
        /note="none"
        /gene="dehydrogenase"
        /product="threonine 3-dehydrogenase"
        /pfam_match="PF00107; adh_zinc; 1"
CDS     3373..4455
        /note="putative"
        /gene="methyltransferase"
        /blastp_match="AE001866.DR0026 Deinococcus radiodurans"
        /blast_score=1e-08
CDS     4546..4959
        /blast_score=2e-11
        /blastp_match="AP002997.MLL1617 Mesorhizobium loti"
        /gene="unknown"
        /note="pfam00263, GSPII_III, Bacterial type II and III
        secretion system protein, Expect = 7.8"
CDS     5176..6192
        /blast_score=5e-98
        /blastp_match="AF064070.PE20 Burkholderia pseudomallei"
        /gene="glucose epimerase"
        /note="putative "
        /product="UDP-glucose 4-epimerase"
        /pfam_match="PF01370; Epimerase; 1"
CDS     6331..14043
        /note="substrat AT, malonyl ; zinc depend dehydrogenase ;
        zinc dependent adenosine deaminase putative"
        /gene="PKS I"
        /blastp_match="AF285636.WCBR 2547 Burkholderia mallei"
        /blast_score=0.0
        /pfam_match="ketoacyl-synt"
        /pfam_match="ketoacyl-synt_C"
        /pfam_match="Acyl_transf"
        /pfam_match="SAM binding"
        /pfam_match="adh_zinc"
        /pfam_match="pp-binding"
CDS     14275..15408
        /blast_score=e-104
        /blastp_match="AF285636.WCBT Burkholderia mallei"
        /gene="acyl-CoA transferase WcbT"
        /note="putative"
        /pfam_match="PF00155; aminotran_1_2; 1"
CDS     15436..16245
        /blast_score=5e-11
        /blastp_match="TTDEFFMT.FMT T. thermophilus"
        /gene="formyltransferase"
        /note="evidence experimental"
        /product="methionyl-tRNA formyltransferase"
        /pfam_match="PF00551; formyl_transf; 1"
        /pfam_match="PF02911; formyl_transf_C; 1"
CDS     16287..17384
        /note="putative"
        /gene="glycotransferase"
        /blastp_match="AF285636.WCBD Burkholderia mallei"
        /blast_score=e-99
CDS     17427..18158
        /blast_score=2e-82
        /blastp_match="AF285636.WZM Burkholderia mallei"
        /gene="ABC-2 transporter Wzm"
        /note="putative"
        /pfam_match="PF01061; ABC2_membrane; 1"
CDS     18248..18847
        /blast_score=7e-61
        /blastp_match="AF285636.WZT Burkholderia mallei"
        /gene="ABC-2 transporter Wzt"
        /note="putative "
        /pfam_match="PF00005; ABC_tran; 1"
CDS     18952..20346
        /note="putative"
        /gene="glycosyltranferase"
        /blast_score=e-101
        /blastp_match="AF285636.WCBE Burkholderia mallei"
        /pfam_match="Glycos_transf_1"
CDS     20442..21167
        /note="putative"
        /gene="unknow"
        /blast_score=1e-26
        /blastp_match="AE009248.ATU3189 Agrobacterium tumefaciens"
CDS     complement(21164..24301)
        /note="tranporter domain"
        /gene="unknow"
        /blast_score=5e-29
        /blastp_match="AE009122.ATU1658 Agrobacterium tumefaciens"
        /prosite_match="PS00402; BPD_TRANSP_INN_MEMBR;
        UNKNOWN 1"
CDS     complement(24351..27023)
        /note="none"
        /gene="unknow"
        /blast_score=5e-29
        /blastp_match="AP003581.ALR0267 Nostoc sp"
CDS     complement(27806..29686)
        /note="none"
        /gene="cell surface protein"
        /blast_score=2e-34
        /blastp_match="AE010748.MA0851 2567
        Methanosarcina acetivorans"
        /product="cell surface protein"
CDS     complement(29535..30872)
        /note="none"
        /gene="cell surface protein"
        /blast_score=2e-36
        /blastp_match="AE010748.MA0851 Methanosarcina acetivorans"
CDS     complement(30848..32647)
        /note="fragment"
        /gene="O-antigen"
        /blast_score=1e-72
        /blastp_match="AF105060.RFBC Riftia pachyptila"
        /product="O-antigen biosynthesis protein"
        /pfam_match="PF00535; Glycos_transf_2"
CDS     complement(32574..35555)
        /note="putative"
        /gene="glycosyltransferase"
        /blast_score=7e-46
        /blastp_match="AE013462.MM2213 Methanosarcina mazei "
CDS     complement(35533..36598)
        /blast_score=7e-37
        /blastp_match="AE013462.MM2213 Methanosarcina mazei"
        /gene="glycosyltransferase"
        /note="putative"
CDS     complement(36516..37400)
        /blast_score=8e-22
        /blastp_match="AP003581.ALR0267 Nostoc sp"
        /gene="ALR0267"
        /note="putative ATP/GTP-binding protein, esterase fush 9e-14"
Sequence 37507 BP; 5531 A; 13507 C; 13011 G; 5458 T; 0 other;
```

The invention also relates to any polynucleotide sequence comprising all or part of these sequences (i.e., SEQ ID NOs: 1 or 2), their complementary strand, or a functional variant thereof. A part of the above sequences includes, preferably, at least 20 consecutive bases, more preferably at least 50 consecutive bases thereof, even more preferably a coding sequence (e.g., an CDS). In this respect, SEQ ID NOs: 1 and 2 comprise several novel open reading frames encoding novel polypeptides involved in biosynthetic pathways. These coding sequences are identified above.

In a specific embodiment, the invention relates to a polynucleotide sequence comprising a sequence selected from nucleotides (CDS) 76-1134; 1096-2430; 1178-1624; 2506-3567; 2906-4222; 4092-5321; 6337-8502; 8181-9530; 9531-10721; 10504-11274; 12874-13689; 14195-15976; 15427-16512; 15579-16253; 16505-17656; 17657-18697; 18615-19304; 19301-20596; 20535-21476; 22025-22951; 23155-26523; 26409-34433; 34418-37500 and 35359-37500 of SEQ ID NO: 1 or a complementary strand thereof.

In an other specific embodiment, the invention relates to a polynucleotide sequence comprising a sequence selected from nucleotides 3-914, 924-2168; 2207-3190; 3373-4455; 4546-4959; 5176-6192; 6331-14043; 14275-15408; 15436-16245; 16287-17384; 17427-18158; 18248-18847; 18952-20346; 20442-21167; 21164-24301; 24351-27023; 27806-29686; 29535-30872; 30848-32647; 32574-35555; 35533-36598 and 36516-37400 of SEQ ID NO: 2 or a complementary strand thereof.

Variants of these sequences include any naturally-occurring variant comprising or or several nucleotide substitutions; sequences variants resulting from the degeneracy of the genetic code, as well as synthetic variants coding for functional polypeptides. Variants include any sequence that hybridise under high stringent conditions, as disclosed for instance in Sambrook et al., to any of the above sequences, and encode a functional polypeptide. The invention also include any nucleic acid molecule encoding a polypeptide comprising all or a fragment of an amino acid sequence encoded by a polynucleotide as disclosed above. Preferably, the fragment comprises at least 10 consecutive amino acid residues, more preferably at least 20, even more preferably at least 30.

The invention also relates to any vector comprising these polynucleotide sequences. These sequences may be DNA or RNA, preferably DNA, even more preferably double-stranded DNA. The invention also relates to a polypeptide encoded by a polynucleotide sequence as defined above. The invention also relates to a method of producing such polypeptides by recombinant techniques, comprising expressing a polynucleotide as defined above in any suitable host cell and recovering the encoded polypeptide. The invention also relates to a recombinant host cell comprising a polynucleotide or a vector as defined above.

An other object of this invention resides in a library of polynucleotides, wherein said library comprises a plurality of environmental DNA fragments cloned into cloning vectors, wherein said environmental DNA fragments contain a common molecular characteristic and wherein said cloning vectors are E. coli cloning vectors comprising a target polynucleotide construct allowing transfer and integration of the environmental DNA into the genome of a selected host cell distinct from E. coli.

The sub-DNA-libraries should have either desired genetic characteristics based on high or low GC content, DNA encoded for a desired enzymatic activity, part or full biosynthetic pathways for metabolites etc., or specific origin such as soil fractions, animal organs, sub fraction of a microorganism community etc. The invention also allows to produce conjugative vector with desired characteristics in accordance with the characteristics of the pre-identified sub-DNA-libraries and functional analysis of mutants in heterologous hosts. It can also be used, without limitation, for the production of mutants by mutagenesis, for DNA sequencing, genes or biosynthetic pathways knock-out by insertion or to confer transfer capabilities for expression, co-expression, over-expression or modification of biosynthetic pathways.

Further aspects and advantages of the invention will be disclosed in the following examples, which should be regarded as illustrative and not limiting the scope of this application.

EXPERIMENTAL SECTION

A—From *E. coli* to *Streptomyces*

In this work, we constructed a fosmid library in *E. coli* from total DNA prepared directly from soil. The library has been screened for presence of biosynthetic pathways. We developed genetic tools for functional genomics that allow gene identification, inactivation and horizontal gene transfer from *E. coli* to *Streptomyces*.

The cloning vectors in the library contain ColE1 replicon for propagation in *E. coli*. Transposable elements based on Tn 5 transposon were produced and used for in vitro modification of selected cloning vectors. Integrated transposable elements contain gene for resistance to apramicyne. Conjugative derivatives were constructed by incorporating origin of transfer from plasmid RP4. A conjugative and site specific integrative transposon was also constructed comprising the integrase gene from φC31 phage, including attP attachement site. Conjugal transfer was demonstrated from an appropriate *E. coli* donor cell to another *E. coli* or *Streptomyces lividans* recipient cell. Constructed transposon was tested for inactivation of the genes cloned into fosmids. Obtained mutants can be used for direct sequencing by adequate primers and transferred by conjugation into *Streptomyces lividans*. Transposable elements thus represent very useful tools for functional analysis of a large DNA libraries cloned into BAC, PAC fosmids or other cloning vectors in which cloned inserts must be transferred into heterologous host.

Materials and Methods

Bacterial strains, plasmids and growth conditions.

*E. coli* DH10B (F— mcrA delta(mrr-hsdRMS-mcrBC) phi80dlacZ deltaM15 delta lacX74 deoR recA1 endA1 araD139 delta (ara, leu)7697 galU galK lambda-rpsL nupG), strain (Epicentre) was used for fosmid and plasmid transformation and DNA amplification. Unless specifically described, all DNA manipulations were performed according to Sambrook, J., et al, (1989).

Soil DNA Extraction and DNA Libraries Construction.

Total bacterial community DNA was extracted and large DNA libraries have been constructed into fosmids according to the method described in WO 01/81357.

Fosmid DNA Extraction and Purification

Fosmids DNA containing soil library were extracted from pools of 96 clones. Culture of recombinant clones were performed in Deep-Well 96 and 48, respectively in 1 ml and 2 ml of LB media containing 12.5 μg ml$^{-1}$ of chloramphenicol. Cultures were grown at 37° C. with shaking at 250 RPM during 22 hours. DNA extraction was done by using the Nucleobond PC100 extraction kit (Macherey Nagel).

PCR Screening for the Detection of PKS Genes

Primers Design

Degenerate PCR primers sets were designed to specifically amplify PKS nucleic acids sequences. Multiple sequence alignment of PKS domains revealed highly conserved motives, in particular in the β-keto acyl synthase domain. Primers Lib1F and Lib2R were designed in conserved motives of the β-keto acyl synthase gene. Lib1F (sense primer, 5'-GGSCCSKCSSTSDCSRTSGAYACSGC-3') and Lib2R (antisense primer, 5'-GCBBSSRYYTCDATSG-GRTCSCC-3') were deduced from β-keto acyl synthase peptide sequences GP(AS)(LV)(AST)(IV) DTAC and GDPIE (TVA)(RAQ)A, respectively. The specific fragment amplified with Lib1F/Lib2R was approximately about 465 bp (corresponding to 155 amino acids). Specificity and efficiency of the PCR systems were validated by testing on positive DNA controls (i.e. genomic DNA from type I PKS producing strain such as *Bacillus subtilis*, *Streptomyces lividans*, *Streptomyces ambofaciens* and *Ralstonia solanocearum*) and negative DNA controls (genomic DNA from strains which are known to do not contain PKS genes). Furthermore, DNA extracted from soil samples were tested to calibrate PCR techniques.

PCR Conditions

PCR conditions were optimised, in particular for concentrations of DMSO, MgCl$_2$, Primers and DNA template quantities. For PCR using microorganism genomic DNA and soil DNA as template (50 to 200 ng), the PCR mix (50 µl) contained 250 µM of dNTP, 5 mM MgCl$_2$ final, 2.5% DMSO, 1×PCR buffer, 0.75 µM of each primer and 2.5 U of Taq DNA polymerase (Sigma) and sterile distilled water. For PCR using fosmid pooled DNA as template (100 to 500 ng), the PCR mix (50 µl) contained 250 µM of dNTP, 5 mM MgCl$_2$ final, 5% DMSO, 1×PCR buffer, 0.75 µM of each primer and 2.5 U of Taq DNA polymerase (Sigma) and sterile distilled water. For identification of positives clones in 96 microtiter plates, 25 µA of each bacteria culture were used as template and PCR conditions were the same as above. Thermocycling program was: a denaturation step at 96° C. for 5 minutes; then 1 minute at 96° C., 65° C. for 1 minute, 72° C. for 1 minute. The first 7 cycles, the annealing temperature was lowered 1° C. per cycle until 58° C. was reached. A subsequent 40 cycles were carried out with the annealing temperature at 58° C. A final extension step was at 72° C. for 7 minutes. For identification of positives clones in 96 microtiter plates, the first denaturation step of 96° C. was during 8 minutes. The other steps were the same as described above. PCR reactions were performed with a PTC 200 thermocycler (MJ Research).

PCR Products Analysis

PCR products of about 465 bp were purified on agarose gel with gel extraction Kit (Qiagen) according to the manufacturer recommendations. First approach consisted in subcloning PCR products using the Topo PCR II kit (Invitrogen). Recombinant Plasmids were extracted using QIAprep plasmid extraction Kit (Qiagen) and sequenced with Forward and Reverse M13 primers with CEQ 2000 automated sequencer (Beckman Coulter). Second approach consisted in direct sequencing of PCR products. Sequencing data were compared with nucleic and proteic genbank database using BLAST program.

Sequencing of the Identified Fosmid Insert DNA and Sequence Analysis

Fosmids inserts were sequenced using either a transposon-mediated and by shotgun subcloning approach. Transposition was realized by using (Transposition Kit) commercialized by Epicentre according to the manufacturer. For shotgun subcloning, transformants were grown for 16 hours at 37° C. Fosmid extraction was done by using the Nucleobond PC100 extraction kit (Macherey Nagel). DNA was partially restricted with Sau3A and sized on standard gel elecrtphoresis for fragments ranging from 1 to 3 Kbs and cloned into Bluescript vector according to Sambrook et al. (1989). Sequence analysis was performed with the identification of ORFs by using Frameplot of the GC3. Each identified ORF was compared to gene databases by using BLAST program. PKS domains were determined by aligning obtained sequence versus already described PKS domains from domain databases.

Sequencing

Sequencing reactions were performed with 1 µg of DNA and 3.6 µmol of primer, using CEQ 2000 Dye Terminator Cycle Sequencing kit (Beckman Coulter) under conditions proposed by supplier. Ten µL of reaction products were precipitated using 4 µL of solution containing 1.5 M NaOAc, 50 mM EDTA and 60 µL cold 95% ethanol/dH$_2$O from −20° C. The pellet was washed 2 times with 200 µL 70% ethanol/dH$_2$O, vacuum dried and dissolved in 40 µL sample loading solution (supplied in kit). Sequencing reactions were run on an CEQ 2000 sequencer (Beckman Coulter).

Plasmids Construction and Validation

Plasmid pP1 was constructed as follows. A 941 bp DNA fragment containing native promoter region and AA(3)IV gene was amplified by polymerase chain reaction (PCR) using primers AmF (d-CCCTAAGATCTGGTTCATGTG-CAGCTCCATC, SEQ ID NO: 9) and AmR (d-TAGTAC-CCGGGGATCCAACGTCATCTCGTTCTCC, SEQ ID NO: 10). One hundred microliter reaction were performed containing 0.1 µM each of primers, 1× Vent DNA polymerase buffer (NEB), 0.2 µM of each deoxyribonucleoside triphosphate (dNTP), 50 ng of the DNA template and 2 U of Vent DNA polymerase (NEB). PCR mixture was heated for 4 min at 94° C. in a PTC-200 thermocycler (Peltier) and cycled 25× at 94° C. for 60 sec, 59° C. for 30 sec and at 72° C. for 70 sec. The final extension was performed at 72° C. for 7 min.

PCR product was purified using GFX DNA purification kit (Amersham), then digested by Bgl II and Sma I restriction enzymes. A 941 bp BglII/SmaI fragment was inserted into the Bam HI, Sma I sites of pMOD plasmid (EPICENTRE). DH10B *E. coli* was transformed with pP1 and subjected to apramicyne selection on LB agar plates. Six colonies surviving on apramicyne selection were grown in liquid LB media and final pPL1 candidates were thoroughly checked via PCR and restriction mapping.

To construct conjugative plasmid pPL1, 750 bp oriT DNA region from plasmid RP4 were amplified via PCR using primers oriTF (d-GCGGTAGATCTGTGATGTACTTCAC-CAGCTCC, SEQ ID NO: 11) and oriTR (TAGTACCCGGG-GATCCGACGGATCTTTTCCGCTGCAT, SEQ ID NO: 12). PCR conditions were as above. Amplified DNA was digested using Bgl II and Smal restriction enzymes. BglII/SmaI DNA fragment was subjected to purification after gel electophoresis on 0.7% agarose. Purified fragment was ligated into pP1 plasmid digested by Bam HI and Sma I restriction enzymes.

φC31 integrase gene and attachment site (attP) was amplified via PCR using primers Fint (d-AACAAAGATCTCCCG-TACTGACGGACACACCG, SEQ ID NO: 13) and PJ (d-CGGGTGTCTCGCATCGCCGCT, SEQ ID NO: 14). Amplified DNA fragment was purified by GFX kit (Amersham) and phosphorilated using T4 polynucleotide kinase (NEB) under conditions recommended by the enzyme manufacturer. Phosphorilated DNA fragment was cloned in to pPL1 vector opened with SmaI restriction enzyme (NEB) and dephosphorilated by calf alkaline phosphatase (NEB). DH10B *E coli* was transformed with ligation mixture using Bio Rad Pulsing apparatus and protocols provided by Bio-Rad. Twelve transformants were analyzed by PCR for the presence of integrase gene. Orientation of integrase gene was verified by restriction analysis using Bgl II and EcoRI restriction enzymes. Resulting plasmid was named pPAOI6. To construct pPAOI6-A plasmid, pPAOI6 plasmid was digested with EcoRI and BgiII restriction enzymes followed by digestion by Bean mung nuclease (NEB). Linearised plasmid was self ligated and transformed in to DH10B cells.

Plasmid Preparation of Fosmid DNA

Fosmid and BAC DNA for sequencing was prepared by using the Nucleobond AX kit (Macherey-Nagel), following protocol for BACs, Cosmid as specified by manufacturer.

Mutagenesis

Transposon Tn-pPAOI6 was prepared by digestion of pPAOI6 plasmid using PvuII restriction enzymes, followed separation on agarose gel and purification of fragment containing transposon from gel using Qiagen kit. The same molar ratio of transposon and corresponding fosmid was used for mutagenesis in vitro using Tn5 transposase (Epicentre) and conditions specified by manufacturer. We transformed aliquot of the transposed mixture by electroporation into competent DH10B E. coli strain.

Conjugation E. coli-Streptomyces lividans TK24

Conjugation experiments were done using $6 \times 10^6$ E coli S17.1 cells containing conjugative plasmids or fosmids. The E coli cells were grown in LB media with adequate antibiotic. The cells were collected by centrifugation, washed two times using same volume of LB media and concentrated to $10^8$ cells/ml and overlaid on LB plates containing $2 \times 10^6$ pregeminated Streptomyces lividans TK24 spores. The cells mixture were grown over night at 30° C. and E. coli cells were washed three times using 2 ml of LB media. The plates were overlayed using top agar containing NAL (nalidixic acid) and the appropriated antibiotic. Plates were incubated for 4 days at 30° C. and transformant streptomyces colonies were isolated on HT medium (Pridham et al. 1957) containing NAL and the same appropriated antibiotic.

Results

Construction of a Transposon Tn <Apra>.

E. coli aminoglycoside-(3)-acetyl transferase IV gene (aa (3)IV) was amplified by PCR and cloned in pMOD vector (Epicentre). Advantage of this selective marker allow positive selection in E. coli and in Streptomyces lividans. Transposon can be used for insertional inactivation in vitro using purified transposase Tn5 (Epicentre). The structure of the pP1 constructed vector and transposon was shown on FIG. 1a,1b.

Construction of a Conjugative Plasmid-Transposon.

Conjugative vector, transposon was constructed by cloning origin of transfer from plasmid RP4 into pP1 vector producing pPL1 vector (FIGS. 2a, 2b). The origin of transfer was cloned in such orientation that the selective aa(3)IV gene is the last transferred during conjugation. PPL1 vector was introduced in to specific E. coli S17.1 strain that carry RP4 plasmid integrated in to chromosome. In conjugation experiment between donor strain S17.1 carrying pPL1 plasmid and DH10 E coli receptor we obtained DH10B strain carrying pPL1 plasmid. This data shows that cloned oriT fragment is functional in the pPL1 plasmid. Plasmid pPL 1 can be used for DNA cloning, gene inactivation by homologous recombination. Cloned genes or part of the gene cloned could be then transferred by conjugation in to another host. Another advantage of this vector is conjugative transposon that can be excised from vector and inserted randomly in vivo in to another DNA molecule by purified Tn 5 transposase.

Construction of a Conjugative, Site Specific Integrative Plasmid-Transposon for Horizontal Gene Transfer Between E. coli and Streptomyces Strains.

PPL1 plasmid was used to clone an integrase gene from phage φC31, resulting a plasmid pPAOI6 (FIG. 3a, 3b). We tested several clones for horizontal transfer between E. coli S17.1 strain and Streptomyces lividans TK24 strain. The best transfer was obtained for plasmid pPAOI6 were orientation of integrase gene is in opposite orientation to the gene for resistance to apramycine. Conjugative transfer of pPAOI6 gene in to S. lividans strain is confirmed by resistance to apramycine or G418. Additional confirmation of transfer was obtained using PCR method. We were able to amplify 2 kb insert using specific primers for the φC31 integrase gene, and no PCR amplification was obtained for control S. lividans TK24 strain.

pPAOI6 transposon was cloned into the EcoRV site of plasmid pGPS3 (New England Biolabs). This construction allows transposition not only by transposase Tn5 but also using Transposase ABC (New England Biolabs). Resulting plasmid pTn5-7AOI is shown on FIG. 9.

The goal of these constructions was to produce transposons that is further used in functional analysis of the metagenomic DNA library from the soil that were constructed in a laboratory (FIGS. 4a, 4b, 4c).

Functional Analysis of the Metagenomic DNA Library from Soil

The fosmids library consists of 120 512 clones, containing ~40 kb inserts of soil DNA. The library contains approximately 4.8 Gbps of the DNA cloned from soil. Ten percents of the library was screened by using a PCR approach for the presence of the genes involved in production of secondary metabolites (PKS). Using gene-module specific set of primers we were able to identified positive clones organized in microtiter plates (96 wells). Sequences (based on PCR products) obtained from fifteen randomly positive clones indicate that the DNA library contains very little sequence redundancy limited to one and that the sequences were found to be new and very diverse in comparison to gene databases (data not schown).

Two fosmids DNA was prepared from two positive clones (FS3-124 and FS3-135) and analyzed by sequencing. DNA analysis in silico shows high G+C contents of 72% and 69% respectively of the cloned inserts and presence of cluster genes that could be involved in biosynthesis of secondary metabolites. No specific phenotype was observed for the two clones in E coli. We employed pPAOI6 transposon mutagenesis to produce conjugative mutants. Transposon mutants FS3-124::pPAOI6 and FS3-135::pPAOI6 were isolated using apramycine as selective antibiotic. Obtained mutants were then tested on LB pates containing chloramphenicol. About 1% of the tested clones are chloramphenicol sensitive. These clones contain transposon inserted into locus encoding chloramphenicol resistance gene and not into cloned DNA insert. ApraR and ChloS transposon mutants are then used for horizontal gene transfer into Streptomyces lividans TK24 strain. Fosmid DNA was prepared from mutants and transformed into E. coli S17.1 strain. Horizontal gene transfer between E. coli S17.1 and Streptomyces lividans was done due to inserted pPAOI6 transposon. Transconjugants of the Streptomyces lividans were tested by PCR to confirm gene transfer and integration of the conjugative fosmid in to S. lividans chromosome. Both transconjugants showed an increase in doubling time, morphological modifications and pigments production in comparison to the control (FIG. 5).

B—From E. coli to Bacillus subtilis

Plasmid pPSB was constructed as follows: A part of amyE gene from B subtilis was amplified by PCR using primers amyE-BamHI: atcgcaggatcctgaggactctcgaacccg (SEQ ID NO: 15) and amyE-EcoRI: cgactgaattcagatctagcgtgtaaat-tccgtctgc (SEQ ID NO: 16). DNA fragment was digested by EcoRI and BamHI restriction enzymes and ligated into EcoRI, BglII site of pPAOI6 plasmid. Transposable element contains Tn<amyE-int φC31-oriT-apra> is shown on FIG. 6 with plasmid pPSB.

Plasmid pPSBery (FIG. 7) was constructed by cloning erm AM gene into pPSB plasmid. A 1140 bp Sau3A DNA fragment containing ery AM gene with his own promoter was cloned from plasmid pMUTIN (Wagner et al. 1998) into the Bam HI site of plasmid pPSB. Orientation of ery gene was confirmed by sequencing. Transposable element contains Tn <amyE-int φC31-ery-oriT-apra> (FIG. 7).

Plasmid pPSBery-AI was obtained after Sma I digestion and self-ligation of core plasmid (FIG. 8). In this construction, φC31 integrase gene was deleted from transposable element. New transposon is Tn<amyE-ery-oriT-apra> (FIG. 8). All transposons could be released as linear DNA by PvuII digestion from plasmids mentioned above and transposed by transposase Tn 5 (Epicentre) in vitro.

The selection of transposed elements was done using 100 μg/ml erythromycine or 40 μg/ml apramycine in *E coli* or 0.3 μg/ml erythromycine in B subtilis. DNA was transformed by electro-transformation into electrocompetent *E coli* strains or by competence into *B. subtilis*. Integration of imported DNA into amy E locus of *B. subtilis* chromosome was confirmed using pPSBery-AI plasmid. Integration was confirmed by PCR using plasmid-specific and amyE locus-specific primers. Fifteen eryR *B. subtilis* clones were tested by PCR. All transformants showed integration at amyE locus of B subtilis chromosome, confirming the functionality of the method and constructs.

REFERENCES

Brau, B., Pliz, U., and Pipersberg, W. 1984. Genes for gentamicin-(3)-N-acetyltransferases III and IV: I. Nucleotide sequence of the AAC(3)-IV gene and possible involvement of an IS 140 element in its expression. Mol Gen Genet. 193 (1), 179-187.

Guiney, D. G., Yakobson, E., (1983). Location and nucleotide sequence of the transfer origin of the broad host range plasmid RK2. Proc Natl Acad Sci USA, 80: 3595-8.

T. Kaeberlein, K. Lewis, Epstein S. S. 2002. Isolating "Uncultivable" Microorganisms in Pure Culture in a Simulated Natural Environment. Science 296, 1127-1129.

Mazodier, P., Thompson, C., 1989. Intergeneric conjugation between *E. coli* and *Streptomyces* species. J. Bacteriol. 171, 3583-3585. Pace, N. R. (1997). A molecular view of microbial diversity and the biosphere. Science 276: 734-740.

Pridham, T. G., Anderson P., Foley, C., Lindenfelser, L. A., Hesseltine, C. W., and Benetdict R. C. (1957). A selection of media for maintenance and taxonomic study of *streptomyces*. Antibiotics Annual 1956-1957, 947-953.

Voeykova T, Emelyanova L, Tabakov V, Mkrtumyan N. 1998. Transfer of plasmid pTO1 from *Escherichia coli* to various representatives of the order Actinomycetales by intergeneric conjugation. FEMS Microbiol Lett. 162(1):47-52.

Sambrook, J., Fritsch E. F. and Maniatis T. 1989. Molecular cloning: a laboratory manual, $2^{nd}$ edition. Cold Spring Harbor Laboratory, Cold Spring Harbor N.Y.

Torsvik, V., Goksoyr, J. Daae, F. L. 1990. High diversity in DNA of soil bacteria. Appl. Environ Microbiol. 56, 782-787.

Torsvik, V., Sorheim, R. and Goksoyr, J. Total bacterial diversity in soil and sediment communities a review. J. Industr. Microbiol. 17, 170-178.

Torsvik, V., Daae, F. L, Sandaa, R. A., Overas, L. 1998. Novel techniques for analysing microbial diversity in natural and perturbed environments. J. Biotechnol. 64. 53-62.

Wagner, V., Dervyn, E. and Ehrlich S. D. 1998. A vector for systematic gene inactivationin *Bacillus subtilis*. Microbiology. 144, 3097-3104.

Zaehner, H. and Fiedler, F. P. 1995. Fifty years of antimicrobials: past perspectives and future trends. In The need for New antibiotics: Possible Ways Forward. Fifty-Third Symposium of the Society for General Microbiology, Bath. England, UK, (Hunter, P. A., Darby, G. K. & Russell, N. J., eds), pp. 67-84.

Zechner, E. L., de la Cruz, F., Eisenbrandt, R., Grahn, A. M., Koraimann, G., Lanka, E., Muth, G., Pansegrau, W., Thomas, C. M., Wilkins, B. M. and Zatyka, M. (2000) Conjugative-DNA transfer process. In Thomas, C. M. (ed.) The horizontal gene pool. Harwood Academic Publishers.

The invention claimed is:

1. A method for the identification or cloning of polynucleotides encoding a selected phenotype, the method comprising (i) cloning environmental DNA fragments into E. coli cloning vectors and propagating said vectors in E. coli to produce a metagenomic library in E. coli cells, (ii) identifying or selecting cloning vectors in said library which contain DNA fragments having a particular characteristic of interest, (iii) inserting a target polynucleotide construct into said identified or selected cloning vectors in a region of said identified or selected cloning vectors distinct from the DNA fragments having a particular characteristic of interest to form modified cloning vectors, wherein said target polynucleotide construct comprises a nucleic acid encoding an origin of transfer functional in E. coli and a nucleic acid encoding an integrase functional in a selected recipient host cell having a genome distinct from E. coli, thereby conferring to the modified cloning vectors the ability to be transferred into said selected recipient host cell, (iv) transferring the modified cloning vectors into said selected recipient host cell and integrating said modified cloning vectors and/or the DNA fragments having a particular characteristic of interest which they contain into the genome of said selected recipient host cell and (v) identifying or cloning the DNA fragments contained in said modified cloning vectors which encode said selected phenotype in said selected recipient host cell, wherein said selected recipient host cell is a microorganism or host cell other than E. coli.

2. The method of claim 1, wherein the cloning vectors are selected from the group consisting of a cosmid, a fosmid, P1 and BAC vectors.

3. The method of claim 1, wherein the library comprises a plurality of unknown polynucleotides.

4. The method of claim 1, wherein the library comprises a plurality of environmental DNA fragments.

5. The method of claim 1, wherein said modified cloning vectors are integrated into the genome of the selected recipient host cell by site-specific integration.

6. The method of claim 1, wherein the origin of transfer is an origin of transfer contained in a plasmid selected from the group consisting of RP4, pTiC58, F, RSF1010 and R6K(α).

7. The method of claim 1, wherein the integrase is ΦC31 integrase.

8. The method of claim 1, wherein the target polynucleotide construct comprises a transcriptional promoter functional in the recipient selected host cell.

9. The method of claim 1, wherein the target polynucleotide construct is contained in a transposable nucleic acid construct.

10. The method of claim 9, wherein the transposable nucleic acid comprises two inverted repeats, the target polynucleotide construct and a marker gene, said inverted repeats flanking the target polynucleotide construct and the marker gene.

11. The method of claim 1, wherein the cloning vectors comprise a first marker gene and wherein, in step ii), the selected cloning vectors are modified by:

contacting in vitro, in the presence of a transposase, the selected cloning vectors with a transposon comprising two inverted repeats, the target polynucleotide construct and a second marker gene distinct from the first marker gene, with inverted repeats flanking the target polynucleotide construct and the second marker gene, and selecting the cloning vectors which have acquired the second marker gene and which have lost the first marker gene.

12. The method of claim 1, wherein, in step (i), the cloning vectors which contain a polynucleotide having a particular characteristic are selected by molecular screening.

13. The method of claim 1, wherein, in step (iii), the modified cloning vectors are transferred into the selected recipient host cell by conjugative transfer.

14. The method of claim 1, wherein said particular characteristic is a nucleic acid sequence or motif characteristic of a particular activity or gene.

15. The method of claim 1, wherein said environmental DNA fragment is at least 10 kilobases in length.

16. The method of claim 1, wherein said environmental DNA fragment is between about 40 kilobases and 80 kilobases in length.

17. The method of claim 5, wherein said site specific integration into the genome of the recipient host cell is stable.

18. A method for the identification or cloning of polynucleotides encoding a selected phenotype, the method comprising:
(i) cloning environmental DNA fragments into *E. coli* cloning vectors and propagating said cloned environmental DNA fragments in *E. coli* to produce a metagenomic library;
(ii) identifying or selecting cloning vectors in said library which contain DNA fragments having a particular characteristic of interest or encoding a selected phenotype;
(iii) inserting a target polynucleotide construct into said identified or selected cloning vectors in a region of said identified or selected cloning vectors distinct from the DNA fragments having a particular characteristic of interest to form modified cloning vectors, wherein said target polynucleotide construct comprises a nucleic acid encoding an origin of transfer functional in *E. coli* and a nucleic acid encoding an integrase functional in a selected recipient host cell having a genome distinct from *E. coli*, thereby conferring to the modified cloning vectors the ability to be transferred into said selected recipient host cell;
(iv) transferring the modified cloning vectors into said selected recipient host cell and integrating said modified cloning vectors and/or the DNA fragments having a particular characteristic of interest which they contain into the genome of said selected recipient host cell; and
(v) identifying or cloning the DNA fragments contained in said modified cloning vectors which encode said particular characteristic of interest in said selected recipient host cell, wherein said selected recipient host cell is a microorganism or host cell other than *E. coli*.

19. The method according to claim 18, wherein said identifying or selecting a particular characteristic of interest comprises sequencing said DNA fragments after cloning to identify a consensus sequence or a motif associated with said particular characteristic of interest.

20. The method according to claim 18, wherein said identifying or selecting a particular characteristic of interest comprises hybridizing said DNA fragments after cloning with probes that identify a consensus sequence or a motif associated with said particular characteristic of interest.

21. The method according to claim 18, wherein said identifying or selecting a particular characteristic of interest comprises amplifying said DNA fragments after cloning with primers that identify a consensus sequence or a motif associated with said particular characteristic of interest.

* * * * *

UNITED STATES PATENT AND TRADEMARK OFFICE
CERTIFICATE OF CORRECTION

PATENT NO.         : 7,910,522 B2
APPLICATION NO.    : 10/522037
DATED              : March 22, 2011
INVENTOR(S)        : Renaud Nalin et al.

It is certified that error appears in the above-identified patent and that said Letters Patent is hereby corrected as shown below:

Column 3,
Line 40, "An other" should read --Another--.

Column 5,
Line 46, "meteorits" should read --meteorites--.

Column 8,
Line 25, "By "specific" is meant" should read --By "specific" it is meant--.
Line 27, "By "targeted" is meant" should read --By "targeted" it is meant--.

Column 9,
Line 31, "An other" should read --Another--.

Column 11,
Line 53, "In an other" should read --In another--.
Line 54, "for or functional in" should read --for, or functional in,--.
Line 60, "In an other" should read --In another--.

Column 19,
Line 20, "In an other" should read --In another--.
Line 30, "comprising or or several" should read --comprising several--.
Line 36, "also include" should read --also includes--.
Line 53, "An other" should read --Another--.

Column 22,
Line 25, "reaction were" should read --reaction was--.

Signed and Sealed this
Twenty-seventh Day of September, 2011

David J. Kappos
*Director of the United States Patent and Trademark Office*

Column 23,
Lines 12-13, "followed separation" should read --followed by separation--.

Column 24,
Line 28, "identified" should read --identify--.
Line 34, "schown" should read --shown--.
Line 35, "was prepared" should read --were prepared--.
Line 45, "LB pates" should read --LB plates--.

Column 25,
Line 12, "pPSBery-AI" should read --pPSBery-ΔI--.
Line 25, "pPSBery-AI" should read --pPSBery-ΔI--.